(12) United States Patent
Differding et al.

(10) Patent No.: US 8,034,958 B2
(45) Date of Patent: *Oct. 11, 2011

(54) 2-OXO-1-PYRROLIDINE DERIVATIVES, PROCESSES FOR PREPARING THEM AND THEIR USES

(75) Inventors: Edmond Differding, Louvain-la-Neuve (BE); Benoît Kenda, Emines (BE); Bénédicte Lallemand, Waimes (BE); Alain Matagne, Gerpinnes (BE); Philippe Michel, Beersel (BE); Patrick Pasau, Chastre (BE); Patrice Talaga, Watermael-Boitsfort (BE)

(73) Assignee: UOB Pharma, S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/656,808

(22) Filed: Feb. 17, 2010

(65) Prior Publication Data

US 2010/0222576 A1  Sep. 2, 2010

Related U.S. Application Data

(60) Division of application No. 12/000,512, filed on Dec. 13, 2007, now Pat. No. 7,692,028, which is a continuation of application No. 11/043,176, filed on Jan. 27, 2005, now Pat. No. 7,358,276, which is a division of application No. 10/693,917, filed on Oct. 28, 2003, now Pat. No. 6,911,461, which is a division of application No. 10/204,266, filed as application No. PCT/EP01/01992 on Feb. 21, 2001, now Pat. No. 6,784,197.

(30) Foreign Application Priority Data

Feb. 23, 2000 (GB) .................... 0004297.8

(51) Int. Cl.
*C07D 207/00* (2006.01)
(52) U.S. Cl. .................................................. 548/400
(58) Field of Classification Search .................... 548/400
See application file for complete search history.

(56) References Cited

U.S. PATENT DOCUMENTS

| | | | |
|---|---|---|---|
| 2,836,599 | A | 5/1958 | Frankel et al. |
| 4,943,639 | A | 7/1990 | Gobert et al. |
| 6,784,197 | B2 | 8/2004 | Differding et al. |
| 6,911,461 | B2 | 6/2005 | Differding et al. |
| 7,692,028 | B2 * | 4/2010 | Differding et al. ........... 548/400 |

FOREIGN PATENT DOCUMENTS

GB  1309692  3/1973
WO  99/13911  3/1999

OTHER PUBLICATIONS

Prous: Drugs of the Future, ES, Barcelona, vol. 19, No. 2, pp. 111-113 (1994).
Fischer et al.: Pharmazie, vol. 46, pp. 359-360 (1991).
Chemical Abstracts, vol. 95, No. 3, p. 661, Abstract No. 24693r (1981).
Glozman et al.: Khim.-Farm. ZH., vol. 14, No. 11, pp. 43-48 (1980).
Banfi et al.: Farmaco, Ec. Sci., vol. 39, No. 1, pp. 16-22 (1984).
Pellegata et al.: Farmaco, Ec. Sci., vol. 36, No. 10, pp. 845-5 (1981).
Pinza et al.: Farmaco, Ed. Sci., vol. 33, No. 2, pp. 130-141 (1978).
Pifferi et al.: Farmaco, Ed. Sci., vol. 32, No. 8, pp. 602-613 (1977).
Sugawara et al.: Arzneimittel Forschung. Drug. Research, Editio Cantor. Aulendorf, DE, vol. 44, No. 1, pp. 211-213 (1994).
Vettinger et al.: Liebigs Ann. Chem., vol. 2, pp. 195-201 (1990).
Elliott et al.: Journal of Medicinal Chemistry, vol. 37, No. 11, pp. 1562-1568 (1994).
Lehmann et al.: Heterocycles, vol. 51, No. 6, pp. 1389-1400 (1999).
Almeida et al.: Tetrahedron: Asymmetry, vol. 3, No. 11, pp. 1431-1440 (1992).
Chemical Abstracts, vol. 52, No. 10, Abstract No. 2007i (1958).
Koelsch et al., J. Org. Chem., vol. 21, pp. 1211-1213 (1956).
Sugasawa: Chem. Zentralbl., vol. 98, No. II, p. 932 (1927).
Thorsett et al., Journal of Medicinal Chemistry, vol. 29, No. 2, pp. 251-260 (1986).
Keusenkothen et al.: J. Chem. Soc. Perkin Trans1, vol. 17, pp. 2485-2492 (1994).
Thaisrivongs et al., Journal of Medicinal Chemistry, vol. 31, No. 7, pp. 1369-1376 (1988).
Glozman et al., 1981, CAS:95:24693.
Kometani et al., 1991, CAS:115:126869.
Rodriquez et al., 1986, CAS: 105: 108709.

* cited by examiner

*Primary Examiner* — Rei-tsang Shiao
(74) *Attorney, Agent, or Firm* — Wenderoth, Lind & Ponack, L.L.P.

(57) ABSTRACT

The invention concerns 2-oxo-1-pyrrolidine derivatives of formula I,

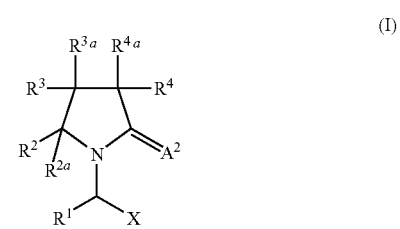

wherein the substituents are as defined in the specification, as well as their use as pharmaceuticals.
The compounds of the invention are particularly suited for treating neurological disorders such as epilepsy.

7 Claims, No Drawings

2-OXO-1-PYRROLIDINE DERIVATIVES, PROCESSES FOR PREPARING THEM AND THEIR USES

This is a divisional of Ser. No. 12/000,512 filed Dec. 13, 2007, now U.S. Pat. No. 7,692,028 which is a continuation of Ser. No. 11/043,176 filed Jan. 27, 2005, now U.S. Pat. No. 7,358,276 which is a divisional of Ser. No. 10/693,917 filed Oct. 28, 2003, now issued as U.S. Pat. No. 6,911,461, which is a divisional of Ser. No. 10/204,266 filed Aug. 20, 2002, now issued as U.S. Pat. No. 6,784,197, which is a 371 of PCT/EP01/01992 filed Feb. 21, 2001.

The present invention concerns 2-oxo-1-pyrrolidine derivatives, processes for preparing them, pharmaceutical compositions containing them and their use as pharmaceuticals.

European Patent No. 0 162 036 B1 discloses the compound (S)-α-ethyl-2-oxo-1-pyrrolidine acetamide, which is known under the International Nonproprietary Name of levetiracetam.

Levetiracetam, a laevorotary compound, is disclosed as a protective agent for the treatment and prevention of hypoxic and ischemic type aggressions of the central nervous system. This compound is also effective in the treatment of epilepsy, a therapeutic indication for which it has been demonstrated that its dextrorotatory enantiomer (R)-α-ethyl-2-oxo-1-pyrrolidine acetamide, also known from European Patent No. 0 165 919 B1, completely lacks activity (A. J. GOWER et al., Eur. J. Pharmacol., 222, (1992), 193-203).

Racemic α-ethyl-2-oxo-1-pyrrolidine acetamide and analogs thereof are known from British Patent No. 1 309 692. U.S. Pat. No. 3,459,738 discloses derivatives of 2-oxo-1-pyrrolidine acetamide. European Patent No. 0 645 139 B1 discloses the anxiolytic activity of levetiracetam. PCT Application No. PCT/EP00/11808 discloses the use of levetiracetam for the curative and/or prophylactic treatment of bipolar disorders, migraine, chronic or neuropathic pain as well as combinations of levetiracetam with at least one compound inducing neural inhibition mediated by $GABA_A$ receptors.

It has now surprisingly been found that certain analogs of levetiracetam, particularly those bearing further substitution in the pyrrolidone ring, demonstrate markedly improved therapeutic properties.

In one aspect, the invention therefore provides a compound having the formula I or a pharmaceutically acceptable salt thereof,

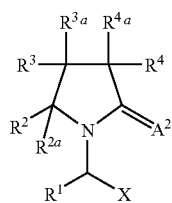

(I)

wherein

X is $—CA^1NR^5R^6$ or $—CA^1OR^7$ or $—CA^1-R^8$ or CN;

$A^1$ and $A^2$ are independently oxygen, sulfur or $—NR^9$;

$R^1$ is hydrogen, alkyl, aryl or $—CH_2—R^{1a}$ wherein $R^{1a}$ is aryl, heterocycle, halogen, hydroxy, amino, nitro or cyano;

$R^2$, $R^3$ and $R^4$ are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative;

$R^{2a}$, $R^{3a}$ and $R^{4a}$ are the same or different and each is independently hydrogen, halogen, alkyl, alkenyl, alkynyl or aryl;

$R^5$, $R^6$, $R^7$ and $R^9$ are the same or different and each is independently hydrogen, hydroxy, alkyl, aryl, heterocycle or an oxy derivative; and $R^8$ is hydrogen, hydroxy, thiol, halogen, alkyl, aryl, heterocycle or a thio derivative;

with the provisos that at least one of as $R^2$, $R^3$, $R^4$, $R^{2a}$, $R^{3a}$ and $R^{4a}$ is other than hydrogen; and that when the compound is a mixture of all possible isomers, X is $—CONR^5R^6$, $A^2$ is oxygen and $R^1$ is hydrogen, methyl, ethyl or propyl then substitution on the pyrolidine ring is other than mono-, di-, or tri-methyl or mono-ethyl; and that when $R^1$, $R^2$, $R^4$, $R^{2a}$, $R^{3a}$ and $R^{4a}$ are each hydrogen, $A^2$ is oxygen and X is $CONR^5R^6$ then $R^3$ is different from carboxy, ester, amido, substituted oxo-pyrrolidine, hydroxy, oxy derivative, amino, amino derivatives, methyl, naphthyl, phenyl optionally substituted by oxy derivatives or in the para position by an halogen atom.

In the definitions set forth below, unless otherwise stated, $R^{11}$ and $R^{12}$ are the same or different and each is independently amido, alkyl, alkenyl, alkynyl, acyl, ester, ether, aryl, aralkyl, heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein is defined as including $—O—R^{11}$ groups wherein $R^{11}$ is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative" as used herein, is defined as including $—S—R^{11}$ groups wherein $R^{11}$ is as defined above except for "thio derivative". Non-limiting examples are alkylthio, alkenylthio, alkynylthio and arylthio The term "amino derivative" as used herein, is defined as including $—NHR^{11}$ or $—NR^{11}R^{12}$ groups wherein $R^{11}$ and $R^{12}$ are as defined above. Non-limiting examples are mono- or di-alkyl-, alkenyl-, alkynyl- and arylamino or mixed amino.

The term "acyl derivative" as used herein, represents a radical derived from carboxylic acid and thus is defined as including groups of the formula $R^{11}—CO—$, wherein $R^{11}$ is as defined above and may also be hydrogen. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative" as used herein, is defined as including a group of the formula $—SO_2—R^{11}$, wherein $R^{11}$ is as defined above except for "sulfonyl derivative". Non-limiting examples are alkylsulfonyl, alkenylsulfonyl, alkynylsulfonyl and arylsulfonyl.

The term "sulfinyl derivative" as used herein, is defined as including a group of the formula $—SO—R^{11}$, wherein $R^{11}$ is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and containing 1-20 carbon atoms, preferably 1-6 carbon atoms for non-cyclic alkyl and 3-6 carbon atoms for cycloalkyl (in these two preferred cases, unless otherwise specified, "lower alkyl"). Alkyl moieties may optionally be substituted by 1 to 5 substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, oxyester, oxyamido, heterocycle, vinyl, C1-5-alkoxy, C6-10-aryloxy and C6-10-aryl.

Preferred alkyl groups are methyl, ethyl, propyl, isopropyl, butyl, iso or ter-butyl, and 2,2,2-trimethylethyl each optionally substituted by at least one substituent selected from the group consisting of halogen, hydroxy, thiol, amino, nitro and cyano, such as trifluoromethyl, trichloromethyl, 2,2,2-trichloroethyl, 1,1-dimethyl-2,2-dibromoethyl, 1,1-dimethyl-2,2,2-trichloroethyl.

The term "alkenyl" as used herein, is defined as including both branched and unbranched, unsaturated hydrocarbon radicals having at least one double bond such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like and being optionally substituted by at least one substituent selected from the group consisting of halogen, hydroxy, thiol, amino, nitro, cyano, aryl and heterocycle such as mono- and di-halo vinyl where halo is fluoro, chloro or bromo.

The term "alkynyl" as used herein, is defined as including a monovalent branched or unbranched hydrocarbon radical containing at least one carbon-carbon triple bond, for example ethynyl, 2-propynyl (=propargyl), and the like and being optionally substituted by at least one substituent selected from the group consisting of halogen, hydroxy, thiol, amino, nitro, cyano, aryl and heterocycle, such as haloethynyl.

When present as bridging groups, alkyl, alkenyl and alkynyl represent straight- or branched chains, C1-12, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl" as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, alkylthio, oxyester, oxyamido, aryl, C1-6-alkoxy, C6-10-aryloxy, C1-6-alkyl, C1-6-haloalkyl. Aryl radicals are preferably monocyclic containing 6-10 carbon atoms. Preferred aryl groups are phenyl and naphthyl each optionally substituted by 1 to 5 substituents independently selected from halogen, nitro, amino, azido, C1-6-alkoxy, C1-6-alkylthio, C1-6-alkyl, C1-6-haloalkyl and phenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "nitrooxy", as used herein, represents a group of the formula —$ONO_2$.

The term "amino", as used herein, represents a group of the formula —$NH_2$.

The term "azido", as used herein, represents a group of the formula —$N_3$

The term "carboxy", as used herein, represents a group of the formula —COOH.

The term "sulfonic acid", as used herein, represents a group of the formula —$SO_3H$.

The term "sulfonamide", as used herein, represents a group of the formula —$SO_2NH_2$.

The term "ester" as used herein is defined as including a group of formula —COO—$R^{11}$ wherein $R^{11}$ is as defined above except oxy derivative, thio derivative or amino derivative.

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —$CONH_2$ or —$CONHR^{11}$ or —$CONR^{11}R^{12}$ wherein $R^{11}$ and $R^{12}$ are as defined above.

The term "heterocycle", as used herein is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl. Non-limiting examples of aromatic heterocycles are pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno(2,3-b) furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, sugar moieties (i.e. glucose, pentose, hexose, ribose, fructose, which may also be substituted) or the same which can optionally be substituted with any suitable group, including but not limited to one or more moieties selected from lower alkyl, or other groups as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1) heptanyl, 7-oxabicyclo(2.2.1)heptanyl, 8-azabicyclo(3.2.1) octanyl.

In the above definitions it is to be understood that when a substituent such as $R^2$, $R^3$, $R^4$, $R^{2a}$, $R^{3a}$, $R^{4a}$, $R^5$, $R^6$, $R^7$, $R^8$ is attached to the rest of the molecule via a heteroatom or a carbonyl, a straight- or branched chain, C1-12-, preferably C1-4-alkylene or C2-12, preferably C2-4-alkenylene or -alkynylene bridge may optionally be interposed between the heteroatom or the carbonyl and the point of attachment to the rest of the molecule.

Preferred examples of X are —COOR$^7$ or —CONR$^5$R$^6$, wherein $R^5$, $R^6$ and $R^7$ are preferably hydrogen, C1-4-alkyl, phenyl or alkylphenyl.

Preferably X is carboxy or —CONR$^5$R$^6$, wherein $R^5$ and $R^6$ are preferably hydrogen, C1-4-alkyl, phenyl or alkylphenyl, especially —CONH$_2$.

Preferably $A^1$ and $A^2$ are each oxygen.

Preferably $R^1$ is hydrogen, alkyl, especially C1-12 alkyl, particularly lower alkyl or aryl especially phenyl.

Examples of preferred $R^1$ groups are methyl, ethyl, propyl, isopropyl, butyl, iso- or ter-butyl, 2,2,2-trimethylethyl each optionally attached via a methylene bridge or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

$R^1$ as ethyl is especially preferred.

Preferably $R^2$ and $R^{2a}$ are independently hydrogen, halogen or alkyl, especially lower alkyl.

Examples of preferred $R^2$ and $R^{2a}$ groups are independently hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

Especially at least one and most preferably both of $R^2$ and $R^{2a}$ are hydrogen.

Preferably $R^{3a}$, $R^4$ and $R^{4a}$ are independently hydrogen, alkyl, especially methyl or ethyl or aryl especially phenyl or aralkyl, especially benzyl.

Examples of preferred $R^{3a}$, $R^4$ and $R^{4a}$ groups are independently hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

Especially at least one and most preferably both of $R^4$ and $R^{4a}$ are hydrogen.

$R^{3a}$ is particularly hydrogen or alkyl, especially lower alkyl and is most preferably hydrogen.

Preferably $R^3$ is hydrogen, C1-12-alkyl, especially C1-6-alkyl, each optionally substituted by one or more substituents selected from hydroxy, halogen, cyano, thiocyanato or alkoxy and attached to the ring either directly or via a thio, sulfinyl, sulfonyl, carbonyl or oxycarbonyl group and optionally, a C1-4-alkylene bridge, particularly methylene; C2-6-alkenyl or -alkynyl, especially C2-3-alkenyl or -alkynyl each optionally substituted by one or more halogens; azido; cyano; amido; carboxy; triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl or piperazinyl each optionally substituted by one or more substituents selected from halogen, C1-6-alkyl and phenyl and attached to the ring either directly or via a carbonyl group or a C1-4-alkylene bridge, particularly methylene; naphthyl; or phenyl, phenylalkyl or phenylalkenyl each optionally substituted by one or more substituents selected from halogen, C1-6-alkyl, C1-6 haloalkyl, C1-6-alkoxy, C1-6-alkylthio, amino, azido, phenyl and nitro and each attached to the ring either directly or via an oxy, sulfonyl, sulfonyloxy, carbonyl or carbonyloxy group and optionally additionally a C1-4-alkylene bridge, particularly methylene.

Also, preferably, $R^3$ is C1-6-alkyl optionally substituted by one or more substituents selected from halogen, thiocyanato, azido, alkoxy, alkylthio, phenylsulfonyl; nitrooxy; C2-3-alkenyl or -alkynyl each optionally substituted by one or more halogens or by acetyl; tetrazolyl, pyridyl, furyl, pyrrolyl, thiazolyl or thienyl; or phenyl or phenylalkyl each optionally substituted by one or more substituents selected from halogen, C1-6-alkyl, C1-6 haloalkyl, C1-6-alkoxy, amino, azido, phenyl and nitro and each attached to the ring either directly or via a sulfonyloxy and optionally additionally a C1-4-alkylene bridge, particularly methylene.

Other examples of preferred $R^3$ groups are hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

$R^3$ is especially C1-4-alkyl optionally substituted by one or more substituents selected from halogen, thiocyanato or azido; C2-5-alkenyl or -alkynyl, each optionally substituted by one or more halogens; thienyl; or phenyl optionally substituted by one or more substituents selected from halogen, C1-6-alkyl, C1-6 haloalkyl or azido.

Further examples of preferred $R^3$ groups are C1-6 alkyl and C2-6 haloalkenyl.

Preferably $R^5$ and $R^6$ are independently hydrogen, methyl, ethyl, propyl, isopropyl, butyl, iso or ter-butyl, 2,2,2-trimethylethyl, especially hydrogen or methyl.

Especially at least one and most preferably both of $R^5$ and $R^6$ are hydrogen.

Preferably $R^7$ is hydrogen, methyl, ethyl, propyl, isopropyl, butyl, iso or tert-butyl, 2,2,2-trimethylethyl, methoxy, ethoxy, phenyl, benzyl or the same substituted by at least one halogen atom such as trifluoromethyl, chlorophenyl.

Preferably $R^7$ is hydrogen, methyl or ethyl especially hydrogen.

Preferably $R^8$ is hydrogen, methyl, ethyl, propyl, isopropyl, butyl, iso or ter-butyl, 2,2,2-trimethylethyl, phenyl, benzyl or the same substituted by at least one halogen atom such as trifluoromethyl, chlorobenzyl.

Preferably $R^8$ is hydrogen or methyl.

Combinations of one or more of these preferred compound groups are especially preferred.

A particular group of compounds of formula I (Compounds 1A) comprises those wherein, A2 is oxygen;

X is —CONR$^5$R$^6$ or —COOR$^7$ or —CO—R$^8$ or CN;

$R^1$ is hydrogen or alkyl, aryl, halogen, hydroxy, amino, nitro, cyano;

$R^2$, $R^3$, $R^4$, are the same or different and each is independently hydrogen or halogen, hydroxy, amino, nitro, cyano, acyl, acyloxy, a sulfonyl derivative, a sulfinyl derivative, an amino derivative, carboxy, ester, ether, amido, sulfonic acid, sulfonamide, alkoxycarbonyl, a thio derivative, alkyl, alkoxy, oxyester, oxyamido, aryl, an oxy derivative, heterocycle, vinyl and $R^3$ may additionally represent C2-5 alkenyl, C2-5 alkynyl or azido each optionally substituted by one or more halogen, cyano, thiocyano, azido, cyclopropyl, acyl and/or phenyl; or phenylsulfonyloxy whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

$R^{2a}$, $R^{3a}$ and $R^{4a}$ are hydrogen $R^5$, $R^6$, $R^7$ are the same or different and each is independently hydrogen, hydroxy, alkyl, aryl, heterocycle or oxy derivative; and $R^8$ is hydrogen, hydroxy, thiol, halogen, alkyl, aryl, heterocycle, alkylthio or thio derivative.

Within these Compounds 1A, $R^1$ is preferably methyl, ethyl, propyl, isopropyl, butyl, or isobutyl; most preferably methyl, ethyl or n-propyl.

$R^2$ and $R^4$ are preferably independently hydrogen or halogen or methyl, ethyl, propyl, isopropyl, butyl, isobutyl; and, most preferably, are each hydrogen.

$R^3$ is preferably C1-5 alkyl, C2-5 alkenyl, C2-C5 alkynyl, cyclopropyl, azido, each optionally substituted by one or more halogen, cyano, thiocyano, azido, alkylthio, cyclopropyl, acyl and/or phenyl; phenyl; phenylsulfonyl; phenylsulfonyloxy, tetrazole, thiazole, thienyl, furyl, pyrrole, pyridine, whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

X is preferably —COOH or —COOMe or —COOEt or —CONH$_2$; most preferably —CONH$_2$.

A further particular group of compounds of formula I (Compounds 1B) comprises those wherein, X is —CA$^1$NH$_2$, —CA$^1$NHCH$_3$ or —CA$^1$N(CH$_3$)$_2$;

$R^1$ is alkyl or phenyl;

$R^3$ is alkyl, alkenyl, alkynyl, cyano, isothiocyanato, ether, carboxyl, amido, aryl, heterocycle; or $R^3$ is CH$_2$R$^{10}$ wherein $R^{10}$ is hydrogen, cycloalkyl, oxyester, oxyalkylsulfonyl, oxyarylsulfonyl, aminoalkylsulfonyl, aminoarylsulfonyl, nitrooxy, cyano, isothiocyanato, azido, alkylthio, arylthio, alkylsulfinyl, alkylsulfonyl, heterocycle, aryloxy, alkoxy or trifluoroethyl;

$R^{3a}$ is hydrogen, alkyl or aryl (especially with the proviso that when $R^{3a}$ is hydrogen, $R^3$ other than methyl);

or $R^3R^{3a}$ form a cycloalkyl;

and $R^2$, $R^{2a}$, $R^4$ and $R^{4a}$ are each hydrogen.

Within the compounds of formula I, $R^1$ is preferably alkyl especially C1-12- more particularly C1-6-alkyl and is most preferably ethyl;

$R^2$, $R^{2a}$, $R^{3a}$, and $R^{4a}$ are preferably hydrogen;

$R^3$ is preferably selected from hydrogen; C1-12-alkyl, especially C1-6-alkyl, each optionally substituted by one or more substituents selected from hydroxy, halogen, cyano, thiocyanato or alkoxy and attached to the ring either directly or via a thio, sulfinyl, sulfonyl, carbonyl or oxycarbonyl group and optionally additionally a C1-4-alkylene bridge, particularly methylene; C2-6-alkenyl or -alkynyl, especially C2-3-alkenyl or -alkynyl, each optionally substituted by one or more halogens; azido; cyano; amido; carboxy; triazolyl; tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl or piperazinyl each optionally substituted by one or more substituents selected from halogen, C1-6-alkyl and phenyl and attached to the ring either directly or via a carbonyl group or a C1-4-alkylene bridge, particularly methylene; naphthyl; or phenyl, phenylalkyl or phenylalkenyl each optionally substituted by one or more substituents selected from halogen, C1-6-alkyl, C1-6 haloalkyl, C1-6-alkoxy, C1-6-alkylthio, amino, azido, phenyl and nitro and each attached to the ring either directly or via an oxy, sulfonyl, sulfonyloxy, carbonyl or carbonyloxy group and optionally additionally a C1-4-alkylene bridge, particularly methylene;

$R^{3a}$ is preferably hydrogen or C1-4-alkyl;

$R^4$ and $R^{4a}$ are preferably, independently hydrogen, C1-4-alkyl, phenyl or benzyl.

A further group of compounds of formula I (Compounds 1C) comprises those in racemic form wherein, when X is —CONR$^5$R$^6$ and $R^1$ is hydrogen, methyl, ethyl or propyl, then substitution on the pyrrolidine ring is other than mono-, di-, or tri-methyl or mono-ethyl.

A further group of compound of formula I (Compounds 1D) comprises those in racemic form wherein, when X is —CONR$^5$R$^6$ and $R^1$ is hydrogen or C1-6-alkyl, C2-6-alkenyl or -alkynyl or cycloalkyl, each unsubstituted, then substitution in the ring is other than by alkyl, alkenyl or alkynyl, each unsubstituted.

A further particular group of compounds of formula I (Compounds 1E) comprises those wherein, X is —CA$^1$NH$_2$;

$R^1$ is H;

$R^3$ is azidomethyl, iodomethyl, ethyl optionally substituted by 1 to 5 halogen atoms, n-propyl optionally substituted by 1 to 5 halogen atoms, vinyl optionally substituted by one or two methyl, and/or 1 to 3 halogen atoms, acetylene optionally substituted by C1-4-alkyl, phenyl or halogen;

$R^{3a}$ is hydrogen or halogen, preferably fluorine;

and $R^2$, $R^{2a}$, $R^4$ and $R^{4a}$ are each hydrogen; as their racemates or in enantiomerically enriched form, preferably the pure enantiomers.

A further particular group of compounds of formula I (Compounds 1F) comprises those wherein, X is —CA$^1$NH$_2$;

$R^1$ is H;

$R^3$ is C1-6-alkyl, C2-6-alkenyl or C2-6-alkynyl optionally substituted by azido, oxynitro, 1 to 6 halogen atoms;

$R^{3a}$ is hydrogen or halogen, preferably fluorine;

and $R^2$, $R^{2a}$, $R^4$ and $R^{4a}$ are each hydrogen; as their racemates or in enantiomerically enriched form, preferably the pure enantiomers.

In all the above mentioned scopes when the carbon atom to which $R^1$ is attached is asymmetric it is preferably in the "S"-configuration.

The "pharmaceutically acceptable salts" according to the invention include therapeutically active, non-toxic base and acid salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

Furthermore certain compounds of formula I which contain alkenyl groups may exist as Z (zusammen) or E (entgegen) isomers. In each instance, the invention includes both mixture and separate individual isomers.

Multiple substituents on the pyrrolidone ring can also stand in either cis or trans relationship to each other with respect to the plane of the pyrrolidone ring.

Some of the compounds of formula I may also exist in tautomeric forms. Such forms although not explicitly indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

The invention also includes within its scope pro-drug forms of the compounds of formula I and its various sub-scopes and sub-groups.

The term "prodrug" as used herein includes compound forms which are rapidly transformed in vivo to the parent compound according to the invention, for example, by hydrolysis in blood. Prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

The compounds of formula I according to their invention can be prepared analogously to conventional methods as understood by the person skilled in the art of synthetic organic chemistry.

The following process description sets forth certain synthesis routes in an illustrative manner. Other alternative and/or analogous methods will be readily apparent to those skilled in this art. As used herein in connection with substituent meanings, "=" means "is" and "≠" means "is other than".

A. Cyclisation of an Aminoester.

When, in formula I, $A^2$=O, an aminoester of formula AA-II is cyclised wherein $Q^1$, together with the oxygen to which it is attached, is a leaving group, especially $Q^1$ is an alkyl group, in particular a linear or branched alkyl group having 1 to 4 carbon atoms.

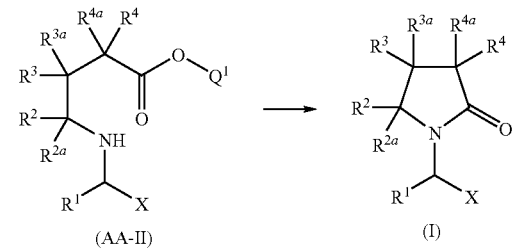

$Q^1$=methyl or ethyl. The reaction is known per se and is generally carried out between room temperature and 150° C., in the presence or not of a catalyst such as acetic acid, hydroxybenzotriazole or 2-hydroxypyridine.

$Q^1$≠methyl or ethyl. Ester of formula AA-II is hydrolysed under acidic or basic conditions then cyclised under conventional peptide synthesis conditions, by using coupling agents, for example dicyclohexylcarbodiimide (Bodanszky, M., Bodanszky, A., in "The Practice of Peptide Synthesis", Springer Verlag, 1984).

A.1 Synthesis of AA-II by Addition on an Itaconate Derivative.

Compounds of formula AA-II wherein $R^{2a}$=$R^{3a}$=H and $R^3$=COO$Q^2$, wherein $Q^2$ represents a linear or branched alkyl group optionally optically active, are obtained by reaction of a compound of formula AA-III with an itaconate derivative of formula AA-IV according to the equation:

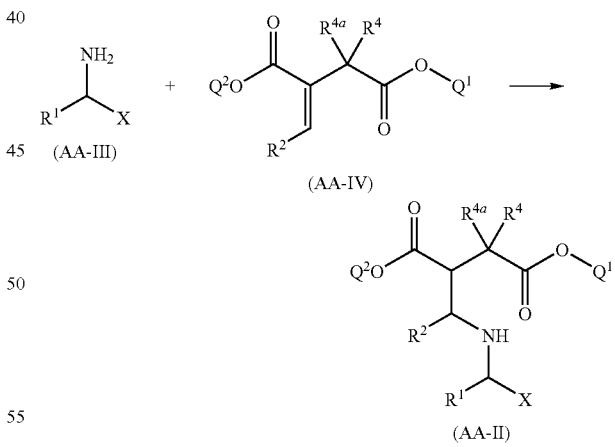

This reaction may be performed according to the procedure described in: Street, L. J., Baker, R., Book, T., Kneen, C. O., ManLeod, A. M., Merchant, K. J., Showell, G. A., Saunders, J., Herbert, R. H., Freedman, S. B., Harley, E. A., J. Med. Chem. (1990), 33, 2690-2697.

A.2 Synthesis of AA-II by Reductive Amination.

A compound of formula AA-II may be prepared by reductive amination of a compound of formula AA-V with a compound of formula AA-III according to the equation:

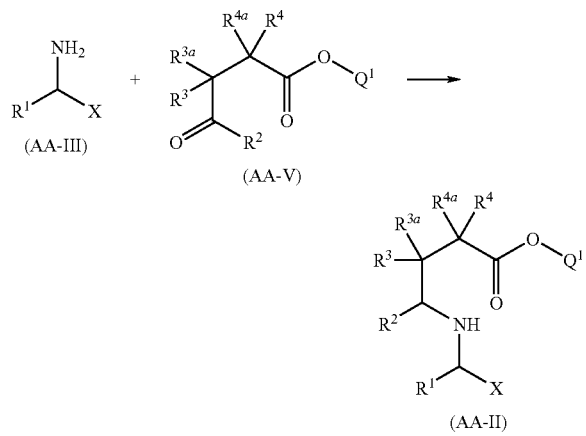

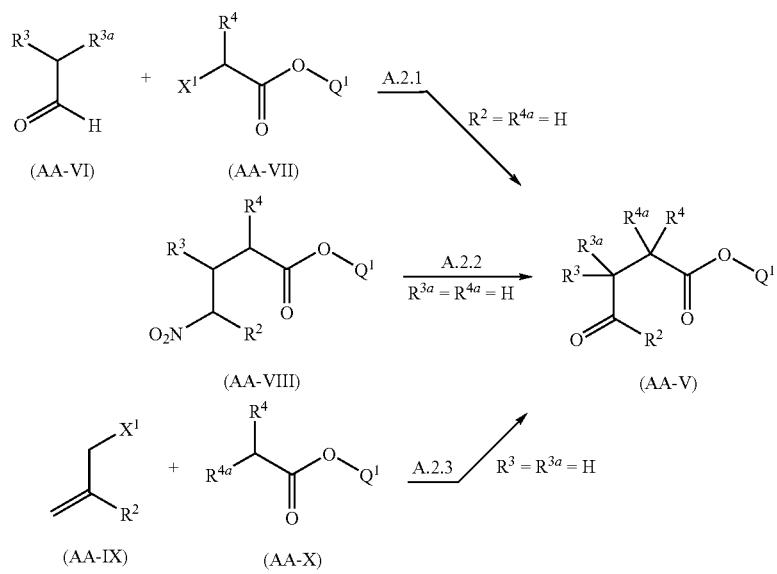

This reaction may be carried out using the conditions described in Abdel-Magid, A. F., Harris, B. D., Maryanoff, C. A., Synlett (1994), 81-83. Alternatively, when X represents $CONR^5R^6$, the amine AA-III may be linked via the amide moiety onto a solid support (for example a Rink resin).

Compounds of formula AA-V may be prepared by one of the following processes:

A.2.1. An aldehyde of formula AA-VI is alkylated with an alkyl halogenoacetate of formula AA-VII, wherein $X^1$ represents a halogen atom, using intermediate enamines as described in Whitessell, J. K., Whitessell, M. A., Synthesis, (1983), 517-536 or using hydrazones as described in Corey, E. J., Enders, D., Tetrahedron Lett. (1976), 11-14 followed by ozonolysis.

A2.2. A nitroester of formula AA-VIII may be transformed into the compound AA-V by treatment of its conjugate base with sulfuric acid in methanol and hydrolysis of the intermediate dimethylacetal (Nef reaction as in Urpi, F., Vilarrasa, J., Tetrahedron Lett. (1990), 31, 7499-7500). The nitroester of formula AA-VIII may be prepared as described in Horni, A., Hubacek, I., Hesse, M., Helv. Chim. Acta (1994), 77, 579.

A.2.3. An ester AA-X is alkylated by an ally halide AA-IX ($X^1$=halogen atom) in the presence of a strong base (for example lithium diisopropylamide), followed by reductive ozonolysis of the unsaturated ester as described in Amruta Reddy P., Hsiang B. C. H., Latifi T. N., Hill M. W., Woodward K. E., Rothman S. M., Ferrendelli J. A., Covey D. F., J. Med. Chem. (1996), 39, 1898-1906.

A.3. Synthesis of AA-II by Alkylation of a γ-Halogeno Ester.

A compound of formula AA-II wherein X=$CONR^5R^6$, $COOR^7$ or CN may be prepared by alkylation of a γ-halogeno ester AA-XI, wherein $X^2$ represents a halogen atom, with an amine AA-III.

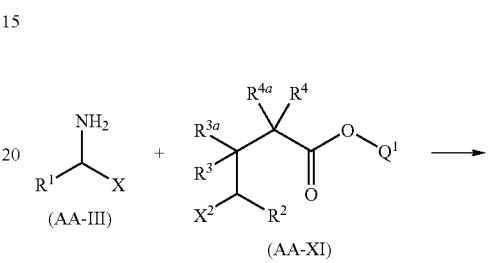

-continued

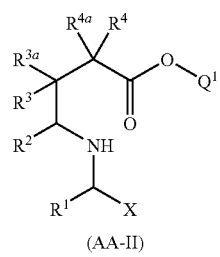

This reaction may be carried out using the conditions described in Patent Application GB 2225322 A. The synthesis of the ester AA-XI is described in part B.

A.4. Synthesis of AA-II by Reductive Amination of 5-Hydroxylactone Derivatives.

A compound of formula AA-II wherein $X=CONR^5R^6$, $COOR^7$ or CN, $Q^1=H$ and $R^{2a}=H$ may be prepared by reductive amination of a 5-hydroxylactone of formula AA-XII with an amine of formula AA-III according to the equation:

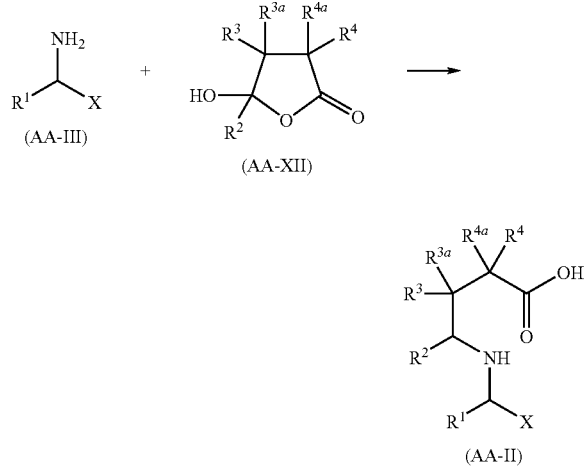

The 5-hydroxylactone of formula AA-XII may be synthesised as described in B.1.

B. Condensation of an Amine with a γ-Halogeno Acid Derivative.

When, in formula I, $A^2=O$, $X=CONR^7R^8$, $COOR^7$ or CN and $R^{2a}=H$, a compound of formula AA-XIII is reacted with an amine of formula AA-III according to the equation:

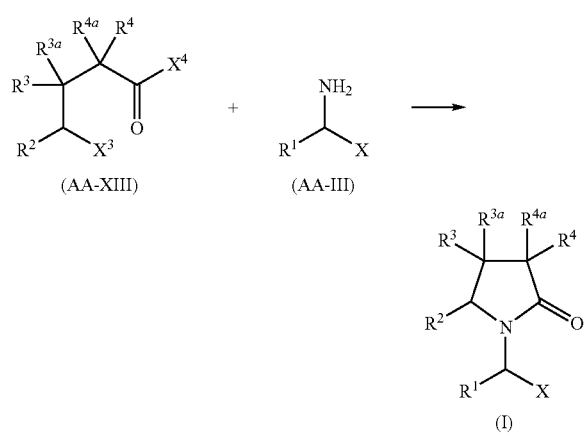

wherein $X^3$ represents a halogen atom, preferably an iodine or a chlorine atom, $X^4$ represents a halogen atom, preferably a chlorine atom. This reaction may be carried out as described in patent application GB 2225322 A.

Compounds formula AA-XIII may be obtained by the opening of a lactone of formula AA-XIV in the presence of an halogenation agent, for example TMSI, $SOCl_2/ZnCl_2$ (followed if necessary by halogenation of the obtained halogeno acid ($X^4=OH$)) according to the equation:

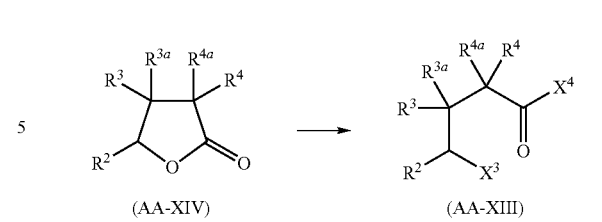

Opening of the lactone AA-XIV can be performed according to the procedure described in: Mazzini, C., Lebreton, J., Alphand, V., Furstoss, R., Tetrahedron Lett. (1998), 38, 1195-1196 and in Olah, G. A., Narang, S. C., Gupta, B. G. B., Malhotra, R., J. Org. Chem. (1979), 44, 1247-1250. Halogenation ($X^4=$halogen) or esterification ($X^4=OQ^1$) of the obtained halogeno acid ($X^4=OH$) may be performed under any conditions known to the person skilled in the art. Lactones of formula AA-XIV may be prepared by one of the following processes:

B.1. Hydrogenation or Conjugated Addition of an Organometallic.

Compound AA-XIV wherein $R^{2a}=R^{4a}=H$ may be obtained hydrogenation of an α,β-unsaturated lactone of formula AA-XV, or by conjugated addition of an organometallic derivative of formula $R^3M$, wherein M represents Li, Na, Mg or Zn, onto compound AA-XV eventually catalysed by Copper (I) salts.

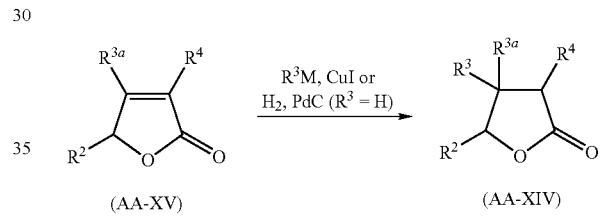

This reaction may be carried out according to the procedures described in: Alexakis, A., Berlan, J., Besace, Y., Tetrahedron Lett. (1986), 27, 1047-1050; Lipshutz, B. H., Ellsworth, E. L., Siahaan, T., J. Amer. Chem. Soc. (1989), 111, 1351-1358, or under any condition known to the person skilled in the art.

B.2 Reduction of a Succinate Derivative.

When, in formula AA-XIV, $R^2=R^{2a}=H$: reduction of the carboxylic acid AA-XVI in the presence of a borohydride reagent, preferably $LiBH_4$ or $Ca(BH_4)_2$, in an alcoholic solvent, according to the equation:

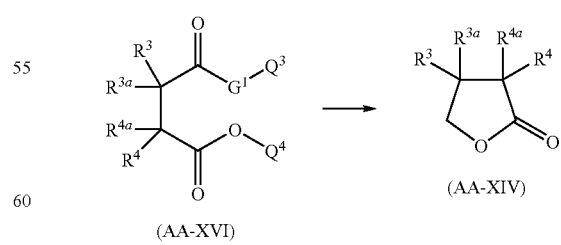

wherein $Q^3$ is a methyl or an ethyl group, $G^1$ represents O or S and $Q^4$ represents an hydrogen atom or a linear or branched alkyl having 1 to 4 atoms of carbon, with the condition that when $G^1=S$, $Q^4=$alkyl and when $G^1=O$, $Q^4=H$.

C. Alkylation of a Lactam Derivative.

When, in formula I, $A^2=O$ and $X=COOR^7$, a compound of formula AA-XVII is reacted with a compound of formula AA-XVIII according to the equation:

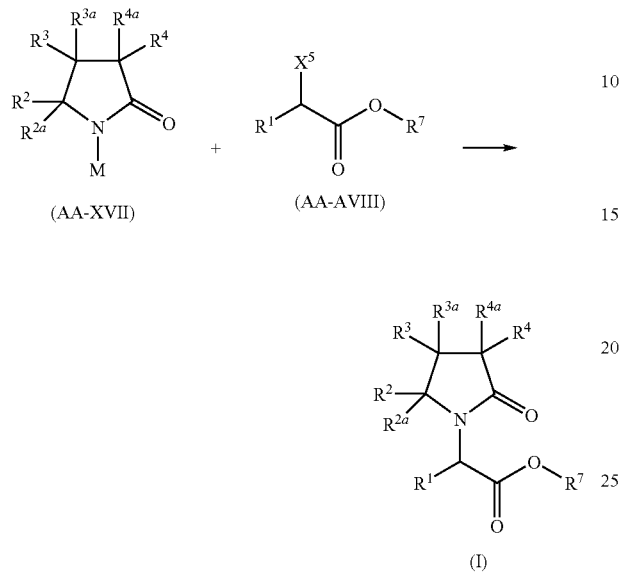

wherein $X^5$ represents a halogen atom and M an alkali metal. This reaction may be carried out following the procedure described in patent application GB (case 15-09).

Compounds of formula AA-XVII may be prepared according to the procedure described in Horni, A., Hubacek, I., Hesse, M., Helv. Chim. Acta (1994), 77, 579.

D. Transformation of an Ester Derivative.

When, in formula I, $A^2=O$ and $X=CONR^5R^6$, none of the groups $R^2$, $R^{2a}$, $R^3$, $R^{3a}$, $R^4$ and $R^{4a}$ being substituted by carboxyl, ester or sulfonic acid, the corresponding ester of formula I

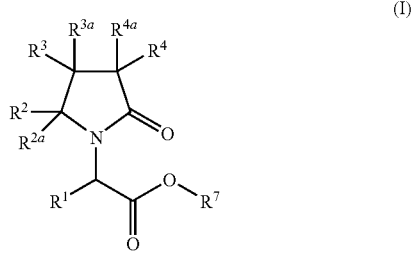

wherein $R^7$ represents a hydrogen atom or a linear or branched alkyl group having 1 to 4 atoms of carbon, is transformed into amine under direct ammonolysis or under conventional peptidic synthesis conditions by using an amine and coupling agents, for example alkyl chloroformate or dicyclohexylcarbodiimide.

E. Reduction of an α,β-Unsaturated Lactam.

When, in formula I, $A^2=O$ and $R^{2a}=R^{3a}=R^{4a}=H$, compounds of formula I may be obtained by reduction of an unsaturated lactam AA-XIX:

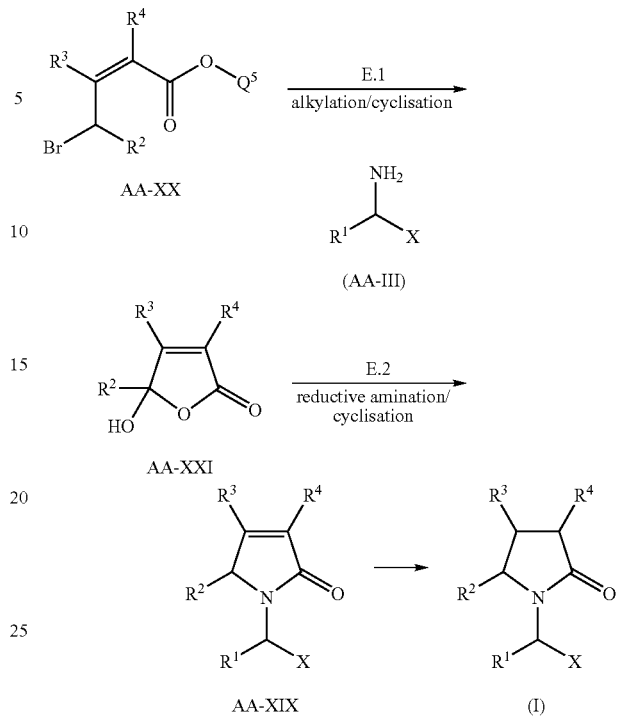

The reduction step may be performed under classical conditions known to the person skilled in the art, for example hydrogen in the presence of Pd/C or optionally in the presence of an optically active catalyst. When $R^2$, $R^3$ or $R^4$ is susceptible to be hydrogenated under low pressure conditions, for example by using Pd/C as catalyst, the double bond of the olefin mixture may be reduced selectively with $NaBH_4$ in the presence of $CoCl_2$.

Compounds AA-XIX may be prepared by one of the following processes:

E.1 By Alkylation

A compound of formula AA-III is alkylated by a compound of formula AA-XX, wherein $Q^5$ represents a linear or branched alkyl group having 1 to 4 atoms of carbon, and cyclised. The alkylation step may be carried out in an inert solvent, for example tetrahydrofuran, dimethylformamide or dichloromethane, between 0 and 50° C., in the presence or not of a tertiary amine. The cyclisation reaction may occur spontaneously or may be carried out according to the method described in part A.

E.2 By Reductive Amination

A compound of formula AA-XXI is reacted with a compound of formula AA-III under reductive amination conditions. The first step of this reaction may be carried out in an inert solvent, for example toluene, between 0 and 50° C., in the presence of a reducing agents such as $NaBH_3CN$ and in the presence of an acid, for example acetic acid. The synthesis of compounds AA-XXI is described in Bourguignon, J. J. et al., J. Med. Chem. (1988), 31, 893-897.

F. Functional Group Transformation of the Side Chain.

F.1 Reduction of Esters into Alcohols.

Compounds of formula I wherein $A^2=O$, $X=CONR^5R^6$ or $COOR^7$, $R^7$ being a tertiary alkyl group, and one of the groups $R^2$, $R^{2a}$, $R^3$, $R^{3a}$, $R^4$ and $R^{4a}$ represents $-G^2-COOQ^6$, $G^2$ being a bond or an alkylene group and $Q^6$ being a linear or branched alkyl group having 1 to 4 atoms of carbon, are key synthesis intermediates for corresponding compounds wherein one of the groups $R^2$, $R^{2a}$, $R^3$, $R^{3a}$, $R^4$ and $R^{4a}$ represents -$G^2$-$CH_2OH$. These transformations may be performed under any conditions known to the person skilled in the art.

F.2 Activation and Oxidation of Alcohols.

Compounds of formula I wherein $A^2$=O and one of the groups $R^2$, $R^{2a}$, $R^3$, $R^{3a}$, $R^4$ and $R^{4a}$ represents -$G^2$-$CH_2OH$, $G^2$ being a bond or an alkylene group, are key synthesis intermediates for corresponding compounds wherein one of the groups $R^2$, $R^{2a}$, $R^3$, $R^{3a}$, $R^4$ and $R^{4a}$ represents -$G^2$-$CH_2X^6$ or -$G^2$-CHO wherein $X^6$ represents a chlorine, a bromine or a iodine atom or a group of formula —O—$SO_2$-$Q^7$ or —O-$Q^8$, $Q^7$ being an alkyl or an aryl group and $Q^8$ being an alkyl group. These transformations may be performed under any conditions known to the person skilled in the art.

F.3 Nucleophilic Substitution of Activated Alcohols.

Compounds of formula I wherein $A^2$=O and one of the groups $R^2$, $R^{2a}$, $R^3$, $R^{3a}$, $R^4$ and $R^{4a}$ represents -$G^2$-$CH_2X^6$, $G^2$ being a bond or an alkylene group and $X^6$ being a chlorine, a bromine or a iodine atom or a group of formula —O—$SO_2$-$Q^7$ as defined in F.2, are key synthesis intermediates for corresponding compounds wherein one of the groups $R^2$, $R^{2a}$, $R^3$, $R^{3a}$, $R^4$ and $R^{4a}$ represents -$G^2$-$CH_2X^7$, wherein $X^7$ represents azido, halogen, nitro, amino, amino derivatives, thio derivatives and heterocycles. These transformations may be performed under any conditions known to the person skilled in the art.

F.4 By Olefination of an Aldehyde.

Compounds of formula I wherein $A^2$=O, X=$CONR^5R^6$, $COOR^7$ or CN, and one of the groups $R^2$, $R^{2a}$, $R^3$, $R^{3a}$, $R^4$ and $R^{4a}$ represents -$G^2$-CHO, $G^2$ being a bond or an alkylene group, are key synthesis intermediates for corresponding compounds wherein one of the groups $R^2$, $R^{2a}$, $R^3$, $R^{3a}$, $R^4$ and $R^{4a}$ represents -$G^2$-$Q^9$ wherein $Q^9$ represents a vinyl group not substituted, mono- or di-substituted by a halogen atom or an alkyl group. These transformations may be performed under any conditions known to the person skilled in the art.

Alternatively, compounds -$G^2$-CN can be obtained from the corresponding aldehyde by reaction of its oxime with $SeO_2$ (as described in Earl, R. A., Vollhardt, K. P. C., J. Org. Chem. (1984), 49, 4786).

F.5 Transformation of an Acid Derivative into Heterocycles.

Compounds of formula I wherein $A^2$=O and one of the groups $R^2$, $R^{2a}$, $R^3$, $R^{3a}$, $R^4$ and $R^{4a}$ represents -$G^2$-CN or -$G^2$-$COQ^{10}$, $G^2$ being a bond or an alkylene group and $Q^{10}$ being an alkoxy, an aryloxy or an amino group, a halogen atom or an amino derivative, with the proviso that —$COQ^{10}$ is different from X, are key synthesis intermediates for corresponding compounds wherein one of the groups $R^2$, $R^{2a}$, $R^3$, $R^{3a}$, $R^4$ and $R^{4a}$ represents -$G^2$-$Q^{11}$ wherein $Q^{11}$ represents either (i) a —CO— aryl/heterocycle by palladium catalysed coupling between an acid chloride -$G^2$-COCl and an aryl/heterocyclic organometallic, for example a trimethylpyridyl-stannane or (ii) an heterocycle, for example a thiazole (in Friedman, B. S., Sparks, M., Adams, R., J. Amer. Chem. Soc. (1933), 55, 2262 or in Iroka, N., Hamada, Y., Shiori, T., Tetrahedron (1992), 48, 7251), an oxazole (in Street, L. J., Baker, R., Castro, J. L., Clamber, R. S., Guiblin, A. R., Hobbs, S. C., Metassa, V. G., Reeve, A. J., Beer, M. S., Middlemis, D. N., Noble, A. J., Stanton, J. A., Scholey, K., Hargreaves, R. J., J. Med. Chem. (1993), 36, 1529), an oxadiazole (Ainsworth, C., J. Amer. Chem. Soc. (1955), 77, 1148), a tetrazole starting from a nitrile (Goerlitzer, K., Kogt, R., Arch. Pharm. (1990), 323, 847) or a thiadiazole (Lamattina, J. L., Mularski, C. J., J. Org. Chem. (1984), 49, 4800).

F.6 Synthesis of Ketone Derivatives.

Compounds of formula I wherein $A^2$=O, and one of the groups $R^2$, $R^{2a}$, $R^3$, $R^{3a}$, $R^4$ and $R^{4a}$ represents -$G^2$-CH=$CQ^{12}Q^{13}$ or -$G^2$-$CQ^{13}$=$CHQ^{12}$, $G^2$ being a bond or an alkylene group, $Q^{12}$ and $Q^{13}$ being a hydrogen atom or an alkyl group, with the proviso that none of the other $R^1$, X, $R^2$, $R^{2a}$, $R^3$, $R^{3a}$, $R^4$ and $R^{4a}$ is bearing a functional group sensible to oxidising conditions, are key synthesis intermediates for corresponding compounds wherein one of the groups $R^2$, $R^{2a}$, $R^3$, $R^{3a}$, $R^4$ and $R^{4a}$ represents respectively -$G^2$-CO—$CHQ^{12}Q^{13}$ or -$G^2$-$CHQ^{13}$-CO-$Q^{12}$.

These transformation may be performed under any appropriate conditions known to the person skilled in the art, for example in presence of $O_2$ and $PdCl_2$, in an inert solvent, for example dimethylformamide or N-methylpyrrolidine, between 0 and 50° C. (Bird, *Transition Metals Intermediate in Organic Synthesis*, Academic Press, NY, (1967), 88-111).

F.7 Derivatisation of Ketones.

Compounds of formula I wherein $A^2$=O, X=$CONR^5R^6$ or $COOR^7$ and one of the groups $R^2$, $R^{2a}$, $R^3$, $R^{3a}$, $R^4$ and $R^{4a}$ represents -$G^2$-CO-$Q^{14}$, wherein $G^2$ is a bond or an alkylene group and $Q^{14}$ represents an alkyl group, are key synthesis intermediates for the synthesis of (i) alcohols -$G^2$-CHOH-$Q^{14}$ by reduction with an hydride reagent ((March, J., *Advanced Organic Chemistry, Third Edition*, John Wiley & Sons, (1985), 809), (ii) fluorinated side chain -$G^2$-$CF_2$-$Q^{14}$ using the conditions described in Lal, G. S., Pez, G. P., Pesaresi, R. J., Prozonic, F. M., Chem. Commun. (1999), 215-216.

F.8 Synthesis of Alkynyl Derivatives.

Compounds of formula I wherein $A^2$=O and one of the groups $R^2$, $R^{2a}$, $R^3$, $R^{3a}$, $R^4$ and $R^{4a}$ represents -$G^2$-C=C$(X^8)_2$, $G^2$ being a bond or an alkylene group and $X^8$ being a halogen atom, with the proviso that none of the other X, $R^1$, $R^2$, $R^{2a}$, $R^3$, $R^{3a}$, $R^4$ and $R^{4a}$ is bearing a functional group sensible sensitive to strong bases, are key synthesis intermediates for corresponding compounds wherein one of the groups $R^2$, $R^{2a}$, $R^3$, $R^{3a}$, $R^4$ and $R^{4a}$ represents -$G^2$-C≡C-$Q^{15}$, wherein $Q^{15}$ is hydrogen, halogen, alkyl or aryl.

These transformation may be performed:
- by base induced β-elimination (for example 1 equivalent of t-BuOK at low temperature as described in Michel, P., Rassat, A., Tetrahedron Lett. (1999), 40, 8579-8581) into an haloacetylenic derivative ($Q^{15}$=halogen) followed by metal catalysed substitution of the halogen by an organometallic species (for example by MeZnCl in the presence of CuCN.LiCl as described in Micouin, L., Knochel, P., Synlett (1997), 327),
- by direct conversion into a metal acetylenide (for example with 2 equiv. of n-butyllithium) and alkylation with an alkylhalide or a carbonyl derivative (as described in Corey, E. J., Fuchs, P. L., Tetrahedron Lett. (1972), 36, 3769-3772).

F.9 Synthesis of Alkanes.

Compounds of formula I wherein $A^2$=O and one of the groups $R^2$, $R^{2a}$, $R^3$, $R^{3a}$, $R^4$ and $R^{4a}$ represents -$G^2$-C=C-$Q^{16}Q^{17}$, $G^2$ being a bond or an alkylene group, $Q^{16}$ and $Q^{17}$ being alkyl or fluoro, are key synthesis intermediates for corresponding compounds wherein one of the groups $R^2$, $R^{2a}$, $R^3$, $R^{3a}$, $R^4$ and $R^{4a}$ represents -$G^2$-CH—CH-$Q^{16}Q^{17}$.

The reduction step may be performed under classical conditions known to the person skilled in the art, for example with hydrogen in the presence of Pd/C (March, J., "Advanced Organic Chemistry, Third Edition", John Wiley & Sons, (1985), 1101-1102).

F.10 Synthesis of (Halo)Azidoaryl Derivatives.

Compounds of formula I wherein $A^2$=O, X=$CONR^5R^6$ or $COOR^7$ or CN and one of the groups $R^2$, $R^3$ or $R^4$ is $G^2$-$Q^{18}$ wherein $Q^{18}$ represents a nitroaryl or triazenoaryl, $G^2$ being a bond or an alkylene group, are key intermediates for the synthesis of corresponding compounds wherein one of the groups $R^2$, $R^3$ or $R^4$ is $G^2$-$Q^{19}$, $Q^{19}$ being an azidoaryl optionally substituted by one or several halogen atoms, preferably Br or F atoms. The transformation proceeds through the reduction of the nitro or triazene moiety into aniline by any means known by persons skilled in the art, optionally introduction of one or several halogen atoms (as in Xing-teng, D., Guo-bin, L., Synth. Commun. (1989), 19, 1261) and conversion of the amine into azide by well known methods.

F.11 Synthesis of Heterocycles from Amines.

Compounds of formula I wherein $A^1$=O, X=CONR$^5$R$^6$, COOR$^7$ or CN, and one of the groups $R^2$, $R^3$ or $R^4$ is $G^2$-$Q^{20}$, wherein $G^2$ being a bond or an alkylene group and $Q^{20}$ is COOH, CONH$_2$ or CN, are key intermediates for the synthesis of corresponding compounds wherein one of the groups $R^2$, $R^3$ or $R^4$ is $G^2$-NH$_2$ or $G^2$-CH$_2$—NH$_2$, which lead to corresponding compounds wherein one of the groups $R^2$, $R^3$ or $R^4$ is $G^2$-Het or $G^2$-CH$_2$-Het, where Het is an heterocycle bound by a nitrogen atom, optionally substituted by one or several halogen atoms.

In the case where X=CONR$^5$R$^6$, CN or COOR$^7$ with $R^7$ different from H, and where $R^2$, $R^3$ or $R^4$ is $G^2$-COOH, the transformation proceeds through Curtius rearrangement (for example by action of diphenylphosphorazidate and triethylamine and quenching in situ by benzyl alcohol as described in: Kim, D., Weinreb, S. M., J. Org. Chem. (1978), 43, 125), deprotection of the amine function by hydrogenolysis or any condition known to the person skilled in the art to give $R^2$, $R^3$ or $R^4$=$G^2$-NH$_2$, followed by ring synthesis to give an heterocycle such as a pyrrole (as in Jefford, C. W., Tang, Q., Zaslona, A., J. Amer. Chem. Soc. (1991), 113, 3513-3518), and optionally introduction of one or several halogen atoms on the ring (as in Gilow, H. M., Burton, D. E., J. Org. Chem. (1981), 46, 2221-2225).

In the case where X=CONR$^5$R$^6$, COOR$^7$ or CN and one of the groups $R^2$, $R^3$ or $R^4$ is $G^2$-CONH$_2$, with X different from CONR$^5$R$^6$, or $G^2$-CN, with X different from CN, the transformation proceeds through selective reduction of the amide or nitrile into the aminomethyl moiety under any condition known to the person skilled in the art, and ring synthesis to give an heterocycle such as a triazole (as in Miles, R. W., Samano, V., Robins, M. J., J. Amer. Chem. Soc. (1995), 117, 5951-5957).

F.12 Synthesis of Triazoles.

Compounds of formula I wherein $A^2$=O and one of the groups $R^2$, $R^{2a}$, $R^3$, $R^{3a}$, $R^4$ and $R^4$ represents -$G^2$-CH$_2$N$_3$, $G^2$ being a bond or an alkylene group, are key synthesis intermediates for corresponding compounds wherein one of the groups $R^2$, $R^{2a}$, $R^3$, $R^{3a}$, $R^4$ and $R^4$ represents -$G^2$-CH$_2$-triazole. These transformations may be performed by prolonged heating in the presence of 1-(triphenylphosphoranylidene)-ketone derivative (as described in Hammerschmidt, F., Polsterer, J. P., Zbiral, E., Synthesis (1995), 415).

F.13 Resolution.

When compounds of formula I present one or several stereogenic centres, and that non-stereoselective methods of synthesis are used, resolution of the mixture of stereoisomers can best be effected in one or several steps, involving generally sequential separation of mixtures of diastereomers into their constituting racemates, using preferably chromatographic separations on achiral or chiral phase in reversed or preferably in direct mode, followed by at least one ultimate step of resolution of each racemate into its enantiomers, using most preferably chromatographic separation on chiral phase in reversed or preferably in direct mode. Alternatively, when partly stereoselective methods of synthesis are used, the ultimate step may be a separation of diastereomers using preferably chromatographic separations on achiral or chiral phase in reversed or preferably in direct mode.

Certain of the intermediate compounds described above particularly those of formula AA-II wherein the various substituents have the meanings set forth above are novel and also form part of the invention. These novel intermediates, wherein the leaving group is pharmaceutically acceptable, possess the same utility as described for the compounds of formula I hereunder.

It has now been found that compounds of formula I and their pharmaceutically acceptable salts are useful in a variety of pharmaceutical indications.

For example, the compounds according to the invention are useful for the treatment of epilepsy, epileptogenesis, seizure disorders and convulsions.

These compounds may also be used for the treatment of other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, essential tremor and other movement disorders, neonatal cerebral haemorrhage, amyotrophic lateral sclerosis, spasticity, Parkinson's disease and other degenerative diseases.

In addition the compounds according to the invention may be used in the treatment of bronchial asthma, asthmatic status and allergic bronchitis, asthmatic syndrome, bronchial hyperreactivity and bronchospastic syndromes as well as allergic and vasomotor rhinitis and rhinoconjunctivitis.

Thus, the present invention, in a further aspect, concerns the use of a compound of formula I or a pharmaceutically acceptable salt thereof for the manufacture of a medicament for the treatment of neurological and other disorders such as mentioned above.

In particular, the present invention concerns the use of a compound of formula I or a pharmaceutically acceptable salt thereof, for the manufacture of a medicament for the treatment of epilepsy, bipolar disorders, chronic pain or neuropathic pain, migraine, bronchial-, asthmatic- or allergic conditions.

The activity and properties of the active compounds, oral availability and stability in vitro or in vivo can vary significantly among the optical isomers of the disclosed compounds.

In a preferred embodiment, the active compound is administered in an enantiomerically enriched form, i.e., substantially in the form of one isomer.

For example, in the case of the compound of formula I wherein $R^1$ is ethyl, X is —CONH$_2$, $A^2$ is oxygen, when $R^3$ is propyl and all remaining substituents are hydrogen, it is the S (butanamide), R (ring) enantiomer which is preferred and when $R^3$ is 2,2-difluorovinyl and all remaining substituents are hydrogen, it is the S (butanamide), S (ring) enantiomer which is preferred.

The present invention also concerns a method for treating epilepsy, migraine, bipolar disorders, chronic pain or neuropathic pain or bronchial-, asthmatic- or allergic conditions, in a mammal in need of such treatment, comprising administering a therapeutic dose of at least one compound of formula I or a pharmaceutically acceptable salt thereof to a patient.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 5 to 1000 mg, preferably 25 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a disorder of brain function characterised by the periodic and unpredictable occurrence of seizures. Seizures can be "nonepileptic" when evoked in a normal brain by treatments such as electroshock or chemical convulsants or "epileptic" when evoked without evident provocation.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society (IHS, 1988) classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV TM), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain The term "neuropathic pain" as used herein refers to pain initiated by a pathological change in a nerve which signals the presence of a noxious stimulus when no such recognisable stimulus exists, giving rise to a false sensation of pain. In other words, it appears that the pain system has been turned on and cannot turn itself off.

The activity of the compounds of formula I, or their pharmaceutically acceptable salts, as anticonvulsants can be determined in the audiogenic seizures model. The objective of this test is to evaluate the anticonvulsant potential of a compound by means of audiogenic seizures induced in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, p. 145-181; Buchhalter J. R., Epilepsia (1993), 34, S31-S41). Results obtained with compounds of formula I are indicative of a strong pharmacological effect.

Another assay indicative of potential anticonvulsant activity is binding to levetiracetam binding site (LBS) as hereinafter described.

The activity of the compounds of formula I, or their pharmaceutically acceptable salts, in chronic neuropathic pain can be determined in animal models. For example, chronic neuropathic pain can be modelled by pharmacologically inducing diabetes in rats. In this model, animals show progressive hyperalgesia to nociceptive stimuli, a symptom generally observed in patients with painful peripheral neuropathy (Courteix C, Eschalier, A. and Lavarenne J., Pain, 53, (1993) 81-88). This model was shown to possess a high pharmacological predictivity. (Courteix C, Bardin M., Chantelauze C., Lavarenne J and Eschalier, A., Pain, 57 (1994) 153-160)

The activity of the compounds of formula I, or their pharmaceutically acceptable salts, in bipolar disorders can be assessed in animal models. For example, bipolar disorders and especially mania can be modelled by pharmacologically inducing hyperactivity in rats and evaluating their behaviour in a Y maze. In such a situation, therapeutic agents effective in man, like Lithium and sodium valproate decrease the hyperactivity, thus validating the predictivity of the model (Cao B. J., and Peng N; A, Eur. J; Pharmacol. 237 (1993) 177-181. Vale A. L. and Ratcliffe F. Psychopharmacology, 91 (1987) 352-355).

Potential anti-asthmatic properties of the compounds of formula I, or their pharmaceutically acceptable salts would be tested for in an animal model of allergic asthma, in which guinea pigs sensitised to ovalbumin are challenged with the antigen and investigated for changes in pulmonary function and airway inflammatory cell content. (Yamada et al. (1992) Development of an animal model of late asthmatic response in guinea pigs and effects anti-asthmatic drugs. Prostaglandins, 43: 507-521).

Activity in any of the abovementioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts, may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof, is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, or parenteral.

Pharmaceutical compositions comprising compounds according to the invention can, for example, be administered orally or parenterally, i.e., intravenously, intramuscularly or subcutaneously, intrathecally.

Pharmaceutical compositions suitable for oral administration can be solids or liquids and can, for example, be in the form of tablets, pills, dragees, gelatin capsules, solutions, syrups, and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenyloin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives.

Of particular interest in accordance with the present invention are combinations of at least one compound of formula I or a pharmaceutically acceptable salt thereof and at least one compound inducing neural inhibition mediated by $GABA_A$ receptors. The compounds of formula I exhibit a potentiating effect on the compounds inducing neural inhibition mediated by $GABA_A$ receptors enabling, in many cases, effective treatment of conditions and disorders under reduced risk of adverse effects.

Examples of compounds inducing neural inhibition mediated by $GABA_A$ receptors include the following: benzodiazepines, barbiturates, steroids, and anticonvulsants such as valproate, viagabatrine, tiagabine or pharmaceutical acceptable salts thereof.

Benzodiazepines include the 1,4 benzodiazepines, such as diazepam and clonazepam, and the 1,5 benzodiazepines, such as clobazam. Preferred compound is clonazepam.

Barbiturates include phenobarbital and pentobarbital. Preferred compound is phenobarbital.

Steroids include adrenocorticotropic hormones such as tetracosactide acetate, etc.

Anticonvulsants include hydantoins (phenyloin, ethotoin, etc), oxazolidines (trimethadione, etc.), succinimides (ethosuximide, etc.), phenacemides (phenacemide, acetylphenetimide, etc.), sulfonamides (sulthiame, acetoazolamide, etc.), aminobutyric acids (e.g. gamma-amino-beta-hydroxybutyric acid, etc.), sodium valproate and derivatives, carbamazepine and so on.

Preferred compounds include valproic acid, valpromide, valproate pivoxil, sodium valproate, semi-sodium valproate, divalproex, clonazepam, phenobarbital, vigabatrine, tiagabine.

For the preferred oral compositions, the daily dosage is in the range 5 to 1000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 5 mg to 1000 mg of compounds of formula I.

The daily dose can fall within a wide range of dosage units of compound of formula I and is generally in the range 5 to 1000 mg. However, it should be understood that the specific doses can be adapted to particular cases depending on the individual requirements, at the physician's discretion.

The amount of the active ingredients (compound I and compound inducing neural inhibition mediated by the $GABA_A$ receptors) in the pharmaceutical composition of the invention will vary depending on the mammal to which the compositions are administered, the disease to be treated, other active ingredients present, etc. Generally, the amount of the compound inducing neural inhibition mediated by the $GABA_A$ receptors and the amount of compound I for a given composition and dosage form can be readily determined employing routine procedures.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or CDCl$_3$) solution at a probe temperature of 313 K and at a concentration of 20 mg/ml. The instrument is locked on the deuterium signal of DMSO-$d_6$ (or CDCl$_3$). Chemical shifts are given in ppm downfield from TMS taken as internal standard.

Mass spectrometric measurements in LC/MS mode are performed as follows:

HPLC Conditions

Analyses are performed using a WATERS Alliance HPLC system mounted with an INERTSIL ODS 3, DP 5 µm, 250× 4.6 mm column.

The gradient ran from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/10 is used just before API source. The chromatography is carried out at 30° C.

MS Conditions

Samples are dissolved in acetonitrile/water, 70/30, v/v at the concentration of about 250 µgr/ml. API spectra (+ or −) are performed using a FINNIGAN (San Jose, Calif., USA) LCQ ion trap mass spectrometer. APCI source operated at 450° C. and the capillary heater at 160° C. ESI source operated at 3.5 kV and the capillary heater at 210 C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Specific rotation is recorded on a Perkin-Elmer MC241 or 341 polarimeter. The angle of rotation is recorded at 25° C. on 1% solutions in MeOH. For some molecules, the solvent is CH$_2$Cl$_2$ or DMSO, due to solubility problems.

Water content is determined using a Metrohm microcoulometric Karl Fischer titrator.

Preparative chromatographic separations are performed on silicagel 60 Merck, particle size 15-40 µm, reference 1.15111.9025, using in-house modified Jobin Yvon-type axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 µm, 100*500 mm column using an in-house build instrument with various mixtures of lower alcohols and C5 to C8 linear, branched or cyclic alkanes at ±350 ml/min. Solvent mixtures as described in individual procedures.

Melting points are determined on a Büchi 535 Totoli-type fusionometre, and are not corrected, or by the onset temperature on a Perkin Elmer DSC 7

Powder X-ray diffraction patterns are acquired at ambient temperature and atmosphere on a computer-controlled Philips PW 1710 equipped with a PW3710 mpd control unit, using a monochromator, Cu Kα radiation (tube operated at 40 kV, 35 mA) and a scintillation counter. The data are collected over an angular range from 4° to 50° 2θ in continuous scan mode using a scan speed of 0.02 2θ/s.

The following abbreviations are used in the examples:

AcOEt Ethyl acetate
AcOH Acetic acid
BuLi n-Butyllithium
n-Bu$_3$P Tri-n-butylphosphine
ClCOOEt or ClCO$_2$Et Ethyl chloroformate
DCE 1,2-Dichloroethane
DIC Diisopropylcarbodiimide
DMSO Dimethyl sulfoxide
DSC Differential Scanning Calorimetry
DMF N,N-Dimethylformamide
Et$_3$N Triethylamine
Et$_2$O Diethyl ether
EtOH Ethanol
FMOC Fluorenylmethyloxycarbonyl
LDA Lithium diisopropylamide
MeCOCl Acetyl chloride
MeCN Acetonitrile
MeOH Methanol
MTBE Methyl terbutyl ether
NMP N-methylpyrrolidinone
PhMe Toluene
PrepLC Preparative Liquid Chromatography
i-Pr$_2$O Diisopropyl ether
i-PrOH Isopropanol
TFA Trifluoroacetic acid
THF Tetrahydrofuran
TMOF Trimethyl orthoformate
TMSCl Chlorotrimethylsilane
TMSI Iodotrimethylsilane Unless specified otherwise in the examples, the compounds are obtained in free (non-salt) form.

EXAMPLE 1

Synthesis of 4-substituted 2-oxo-pyrrolidine butanamides by Reductive Amination of an Aldehyde Ester 1.1. Synthesis of 3-substituted-4-oxo-butanoic acid esters 1.1.1. Route A: by Alkylation of Enamines The synthesis of 5,5-dimethyl-3-formyl-hexanoic acid methyl ester 361 is representative:

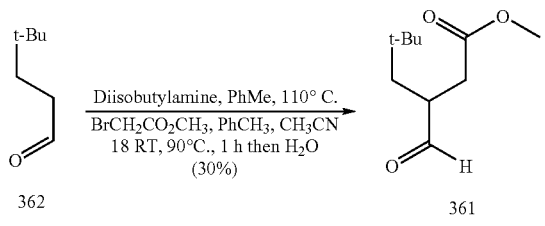
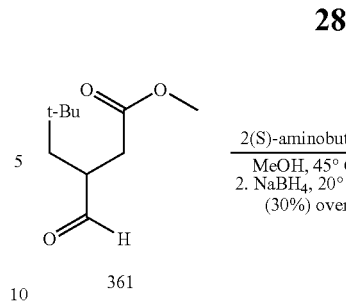

In a three necked flask fitted with a Dean-Stark apparatus under argon, a solution of diisobutylamine (4.62 ml from Acros), 4,4-dimethyl pentanal 362 (2.5 g, 0.021 mol.) in toluene (20 ml) is heated at 130° C. for 2 h and water is extracted. The yellow solution is cooled down to room temperature and methyl bromoacetate (3.7 g, 0.024 mol.) is added in one time. The pink solution is stirred at room temperature overnight and 1 h at 90° C. Water (10 ml) is added at this temperature and after 1 h, the solution is cooled down to room temperature. The organic layer is washed with HCl 1N, saturated aqueous sodium bicarbonate, dried over magnesium sulfate, filtered and evaporated to afford an oil which is distilled under reduced pressure (1 mmHg) to afford 5,5-dimethyl-3-formyl-hexanoic acid methyl ester 361 as a liquid (1.1 g, 0.05 mol, Teb (1 mmHg): 69-71° C.). The aldehyde esters are then used in the reductive amination step.

Alternatively, alkylation with ethyl bromoacetate can be conducted in the presence of toluene-acetonitrile 1/1 (v/v) as solvent. The final aldehyde can also be distilled under reduced pressure.

1.1.2. Other Synthetic Routes

Aldehyde esters may also be obtained by other methods including:

(i) Alkylation of an hydrazone by a bromoacetate derivative. For example, 5-(phenyl)-3-formyl-pentanoic acid 2,2-dimethyl-ethyl ester is obtained by reacting N-(4-phenyl)-propylidene-N,N-dimethyl hydrazone with tert-butyl-bromoacetate and LDA followed by ozonolysis of the alkylated hydrazone.

(ii) Addition of nitromethane to α,β-unsaturated esters. 3-(3-bromo-phenyl)-4-oxo-butanoic acid ethyl ester is obtained by addition of nitromethane to 3-(3-bromo-phenyl)-acrylic ethyl ester in the presence of 1,8-diazabicyclo[5.4.0]undec-7-ene, oxidation of the nitro derivative in the Nef conditions and controlled hydrolysis of the methyl-acetal by HCl.

(iii) Ozonolysis of a 4-pentenoic derivative. 2-benzyl-4-oxo-butanoic acid ethyl ester is obtained by alkylation with lithium diisopropyl amide of 3-phenyl-butanoic acid ethyl ester and allyl bromide followed by ozonolyzis and reduction of the ozonide by PPh$_3$.

1.2. Reductive Amination of 3-substituted-4-oxo-butanoic acid esters and Cyclisation to pyrrolidin-2-one

1.2.1. Reductive Amination

The synthesis of methyl 4-{[((1S)-1-aminocarbonyl)propyl]amino}butanoate 363 is representative.

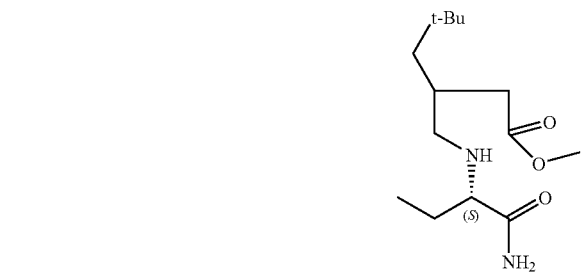

In a three necked flask fitted with a reflux condenser, under argon, a suspension of the aldehyde 361 (1.7 g, 0.09 mol.), (S)-2-amino-butanamide (1.58 g, 0.15 mol.) and molecular sieves (3 Å from Aldrich) in MeOH is heated at 60° C. for 0.5 h. The suspension is cooled down to 0° C. and sodium borohydride (0.55 g) is added by portions. After 1 h at room temperature, the reaction mixture is diluted with ether, washed with water, dried over magnesium sulfate, filtered and evaporated to afford a yellow oil. Methyl 4-{[((1S)-1-aminocarbonyl)propyl]amino}butanoate 363 is used directly in the next step without any further purification.

Alternatively, the reductive amination can be conducted in the same conditions with other reducing agent like NaBH$_3$CN or NaBH(OAc)$_3$ (using 1.4 mol. equivalent respective to the aldehyde ester).

1.2.2. Cyclisation of Butanoic Acid (Methyl or Ethyl) Esters

The synthesis of the two stereoisomers of (2S)-2-(4-neopentyl-2-oxo-1-pyrrolidinyl)butanamide 149 and 148 is representative:

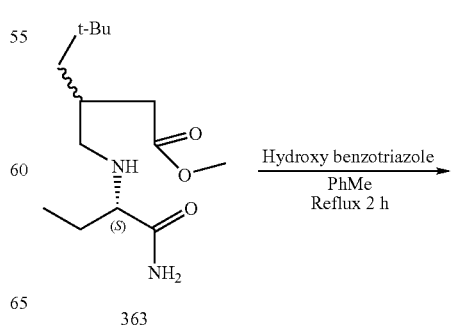

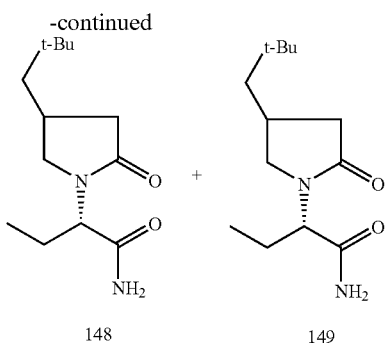

148      149

In a three necked flask fitted with a reflux condenser, under argon, the oily 363 is dissolved in a 1/1 mixture of toluene and 1,2-dichloroethane (25 ml each) in the presence of hydroxy-benzotriazole (2.05 g, available from Aldrich) and the solution is heated at 90° C. for 2 h and cooled to room temperature. The organic phase is washed successively with saturated aqueous sodium bicarbonate, water, dried over magnesium sulfate, filtered and evaporated to afford a brown solid (1.8 g) which is purified by column chromatography on silicagel (Eluent: $CH_2Cl_2$/MeOH 95/05 (v/v)) to afford (2S)-2-(4-neo-pentyl-2-oxo-1-pyrrolidinyl)butanamide (0.89 g, 0.0036 mol.) as a 1/1 mixture of diastereoisomers. Separation of the 2 isomers is realized by chromatography on a chiral stationary phase (EtOH-hexane 1/1 (v/v)) to afford, after recrystalisation in toluene, the two stereoisomers (respectively 0.35 g and 0.37 g). The physico-chemical properties are described in the table. Alternatively, the cyclisation of the aminoester can be conducted with other reagents than hydroxy-benzotriazole like acetic acid (as the solvent) or 2-hydroxy-pyridine (1 equivalent). When acetic acid is used as solvent for the cyclisation, the reaction mixture is evaporated under vacuo to dryness, diluted with dichloromethane and work-up as above.

1.2.3. Other Cyclisation

Alternatively, cyclization can be performed in two steps by (i) acid or basic hydrolysis of the ester and (ii) cyclization of an activated ester in the usual conditions described in peptide synthesis.

1.3. Solid Phase Synthesis of Pyrrolidones

1.3.1. Attachment of the FMOC Protected Amino Acid onto the Rink Amide Resin

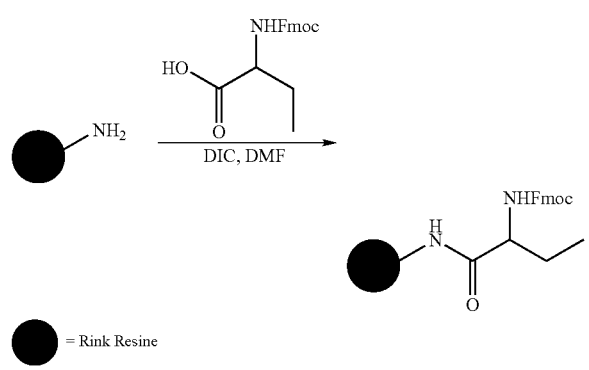

4 g of Rink amide resin (0.51 meq/g, 100-200 mesh) is placed in a glass vessel and stirred in 20% v/v piperidine/DMF (40 ml) for 30 minutes. The resin is drained and the entire deprotection repeated. The resin is filtered, washed (6×DMF) and dried. The resin is suspended in DMF (40 ml) and treated with N-Fmoc-2-aminobutyric acid (3.02 g, 9.28 mmol), followed by a solution of 1,3-dicyclohexyl carbodiimide (1.4 g, 11.13 mmol) in DMF (20 ml). The reaction is stirred for 1 h at room temperature then filtered, washed (DMF) and the coupling process repeated. The resin is filtered, washed (6×DMF, 6×$CH_2Cl_2$), dried and used as it stands in the next steps.

1.3.2. Reductive Amination with Added 5-hydroxy-4-propyl-furan-2-one and Cyclization

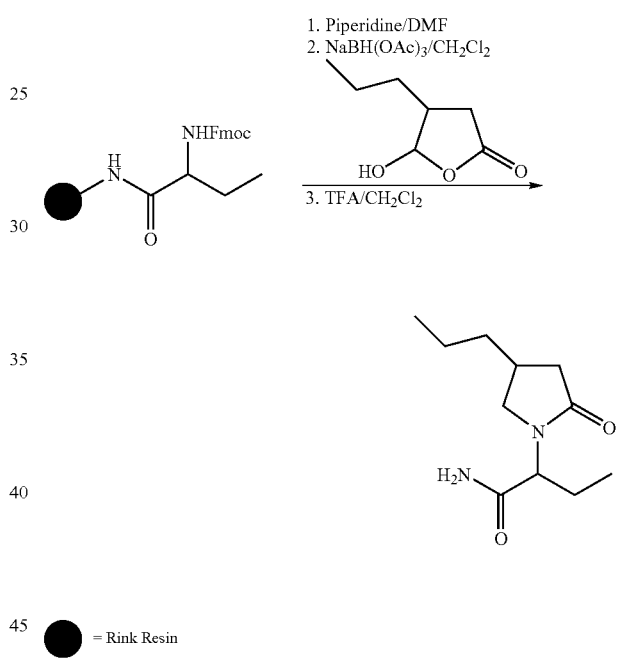

● = Rink Resin 100 mg of the N-Fmoc-2-aminobutyric amide resin (0.051 mmol) is contained within a fritted polypropylene syringe. Removal of the Fmoc group is achieved using 20% piperidine in DMF. To the amino resin is added 5-hydroxy-4-propyl-furan-2-one (from 36.72 mg, 0.25 mmol) in DCE (2 ml). The resin is then treated with acetic acid (15 µl) and sodium triacetoxyborohydride (54 mg, 0.25 mmol). The reaction is stirred for 18 h at room temperature then filtered and washed with the following solvent sequence: $H_2O$/DMF (1:1), DMF, $CH_2Cl_2$, MeOH and dried. The resin is suspended in trifluoroacetic acid/$CH_2Cl_2$ mixture (1/1) for 4 h with vortex agitation, then filtered, washed ($CH_2Cl_2$×2). The filtrate is concentrated, the residue dissolved in $CH_2Cl_2$ (2 ml) and concentrated once more. The desired compounds are purified by LC-MS (Micromass-Gilson, LCZ-Platform, RP-18 column, gradient elution, $CH_3CN$/$H_2O$/TFA1%).

1.3.3. Reductive Amination with Added Aldehydic Esters and Cyclization

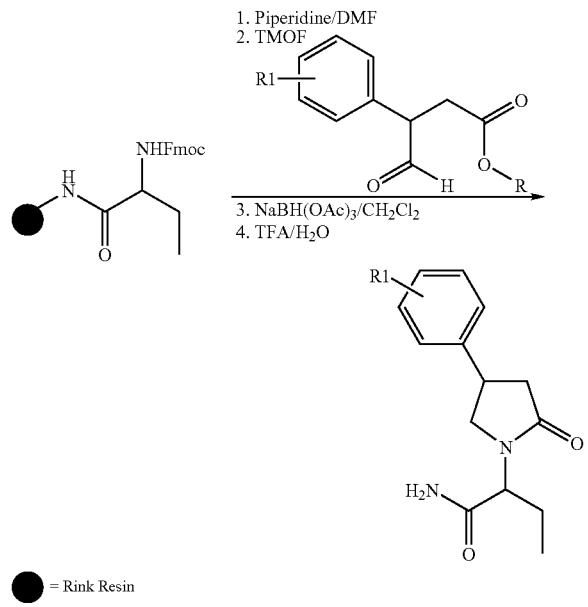

● = Rink Resin 150 mg of the N-Fmoc-2-aminobutyric amide resin (0.087 mmol) is contained within a fritted polypropylene syringe. Removal of the Fmoc group is achieved using 20% piperidine in DMF. To the amino resin is added the aldehyde (0.5 mmol) in TMOF (2 ml). The reaction is stirred for 18 h at room temperature then filtered and washed (CH$_2$Cl$_2$). The resin is swollen with CH$_2$Cl$_2$ and then treated with sodium triacetoxyborohydride (22 mg, 0.104 mmol). The reaction is agitated for an additional 18 h at room temperature. The resin is then washed with the following solvent sequence: H$_2$O×6, MeOH×6, CH$_2$Cl$_2$×6 and dried. The resin is suspended in trifluoroacetic acid/water mixture (95/5) for 1 h with orbital agitation, then filtered, washed (CH$_2$Cl$_2$×2). The filtrate is concentrated, the residue dissolved in CH$_2$Cl$_2$ (2 ml) and concentrated once more. The desired compounds are purified by LC-MS (Micromass-Gilson, LCZ-Platform, RP-18 column, gradient elution, CH$_3$CN/H$_2$O/TFA1%).

EXAMPLE 2

Synthesis of 4-substituted 2-oxo-pyrrolidine butanamides by Ring Opening of 4-substituted γ-lactones

2.1. Synthesis of Lactones

2.1.1. Route A: by Alkylation of 2,3-Furanone

The synthesis of 4-n-butyl-butyrolactone 365 is representative:

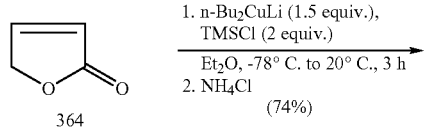

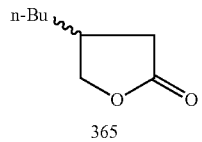

In a three necked flask under argon, n-butyllithium (1.6 M in hexanes, 75 ml, 0.12 mol.) is added to a suspension of CuI (11.42 g, 0.06 mol.) in dry THF (80 ml) cooled at −30° C. After 0.5 h, the solution is cooled down to −78° C., TMSCl (4.75 g, 0.04 mol.) is added dropwise followed by 2,3-furanone 364 (from Aldrich, 3.36 g, 0.04 mol.) dissolved in dry THF. The suspension is allowed to warm to room temperature and hydrolysed with saturated ammonium chloride. The aqueous layer is extracted with AcOEt (3×), washed with water, dried over magnesium sulfate and evaporated to dryness. The crude lactone is purified by distillation (1 mmHg; 73-80° C.) to afford 2.7 g of 4-n-butyl-butyrolactone 365.

Alternatively, the cuprate reagent can be prepared by replacing the organolithium by an organomagnesium, which can be obtained by reaction between and alkyl halogenide and magnesium turnings in the usual conditions for this kind of transformation. THF can be replaced by diethylether (For general information see: Lipshutz, B. H.; Sengupta, S. *Org. Reactions* 1991, 41, 135).

2.1.2. Other Routes

Alternatively, lactones can also be obtained by (i) Reduction of succinate esters. 4-(cyclopropyl)methyl-butyrolactone is obtained by alkylation of monomethylsuccinate by cyclopropylmethyl bromide with lithium diisopropylamide followed by reduction of 2-(cyclopropyl)methyl-succinic acid 1-methyl ester by NaBH$_4$ and CaCl$_2$.

(ii) Reduction of succinic acid 1-alkyl ester 4-alkyl thioester. 4-allyl-butyrolactone is obtained from ethyl 4-pentenoic thioester (synthesized from 4-pentenoic acid and ethanethiol in the presence of dicyclohexyl carbodiimide). Alkylation of ethyl 4-pentenoic thioester by ethylbromoacetate with lithium diisopropylamide afford 2-allyl-succinic acid 1-methyl ester 4-ethyl thioester which is then transformed into 4-allyl-butyrolactone by reacting successively with LiBH$_4$ and sulfuric acid.

2.2. Synthesis of Pyrrolidones

2.2.1. By Acylation/Alkylation of a Butyramide

The synthesis of the two stereoisomers of (2S)-2-(4-allyl-2-oxo-1-pyrrolidinyl)butanamide 228 and 224 is representative:

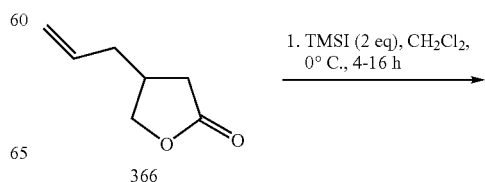

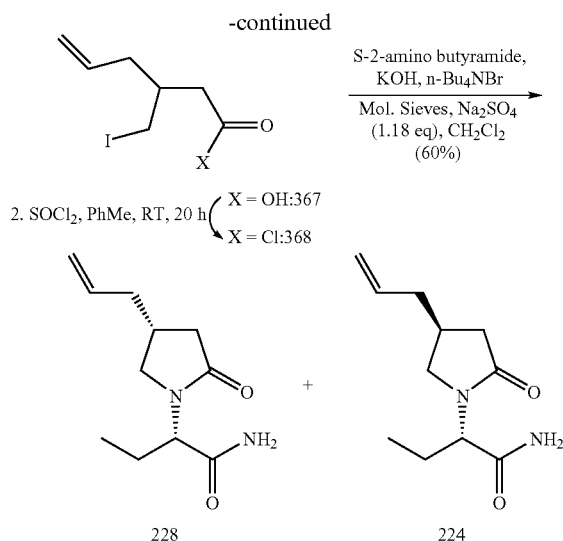

Step 1: Opening of the Lactone

In a three necked flask, under argon, TMSI (51 ml, Aldrich) is added to a solution of the crude 4-allyl-butyrolactone 366 (see procedure §2.1.3., 22.9 g, 0.181 mol.) cooled at 0° C. The solution is stirred for 2 h at room temperature and hydrolysed with 1N HCl (300 ml). The aqueous layer is extracted with $CH_2Cl_2$ and the combined organic phase washed with brine, dried over magnesium sulfate and concentrated in vacuo to afford the crude 3-(iodo)methyl-5-hexenoic acid 367 (44.5 g). $^1$H NMR (250 MHz, $CDCl_3$): 1.80-2.05 (m, 2H), 2.20 (t, 2H), 2.40-2.60 (t, 2H), 5.10-5.20 (m, 2H), 5.15-5.80 (m, 1H).

Step 2: Chlorination of the Iodo Acid

In a three necked flask fitted with a reflux condenser, under argon, a solution of thionyl chloride (25.5 ml) and the crude iodo acid 367 (44.5 g, 0.175 mol.) in benzene (90 ml) is stirred for 24 h at room temperature. The solvents are evaporated under vacuo to afford the crude 3-(iodo)methyl-5-hexenoic acid chloride 368 (47 g) which is used directly in the next step without any further purification. $^1$H NMR (250 MHz, $CDCl_3$): 1.90-2.05 (m, 2H), 2.15 (t, 2H), 2.90-3.10 (m, 2H), 3.25 (dd, 1H), 3.35 (dd, 1H), 5.10-5.20 (m, 2H), 5.15-5.80 (m, 1H).

Step 3: Acylation-Alkylation with S-2-amino-butyramide

In a three necked flask, under argon, the crude acid chloride 368 (47 g, 0.172 mol.) in $CH_2Cl_2$ (300 ml) is added dropwise to a mechanically stirred suspension of molecular sieves (29 g), powdered KOH (22.3 g), anhydrous $Na_2SO_4$ (28.8 g), tetra-n-butyl ammonium bromide (2.8 g, 0.0086 mol.) and S-2-amino butyramide ($[α]^{25}_D$=+19.35°; 26.3 g, 0.26 mol.) in $CH_2Cl_2$ (470 ml) cooled at 0° C. The solution is stirred for 5 h at −5° C., powdered KOH is added (6.2 g) and the stirring is continued for 3 h at −5° C. The reaction mixture is filtered on hyflocel and the solvent is evaporated in vacuo. The crude reaction mixture is purified successively by chromatography on silicagel (AcOEt/i-PrOH: 97/03 (v/v)) and preparative chromatography on a chiral stationary phase (Hexane/EtOH) to afford the two isomers of (2S)-2-(4-allyl-2-oxo-1-pyrrolidinyl)butanamide (respectively 6.0 (228) and 5.48 g (224); 16 and 15%).

Two minor impurities are also isolated following the chiral chromatography, namely two stereoisomers of (2S)-2-[4-(2-iodopropyl)-2-oxo-1-pyrrolidinyl]butanamide 225 (0.22 g) and 226 (0.27 g) as white solids after recrystallisation.

2.2.2. By Alkylation/Acylation of a Butyramide

The synthesis of the two stereoisomers of (2S)-2-(5-nonyl-2-oxo-1-pyrrolidinyl)butanamide is representative:

Step 1: Opening of the Lactone

To a solution of γ-nonalactone (0.32 ml, 2 mmol) in thionyl chloride (164 μl, 2.25 mmol), zinc chloride (12 mg, 0.088 mmol) is added at room temperature and the mixture is stirred for 24 h. Excess methanol is added and the reaction mixture is stirred for 10 min and then concentrated under reduced pressure to give 4-chloro-nonanoic acid methyl ester used as such.

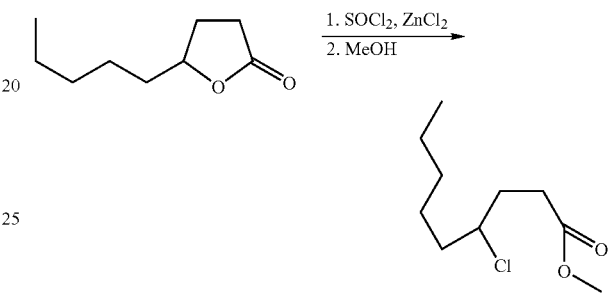

Step 2: Alkylation

To a solution of 4-chloro-nonanoic acid methyl ester (2 mmol) in DMF (2 ml) are successively added 2-amino butyramide (1 g, 10 mmol), 300 mg of sodium iodide (2 mmol) and 276 mg of potassium carbonate (2 mmol). The mixture is stirred overnight at 60° C. The solids are filtered and washed by $CH_2Cl_2$ (2×2 ml). The filtrate is concentrated under reduced pressure to give the ester derivative used as such for the cyclisation.

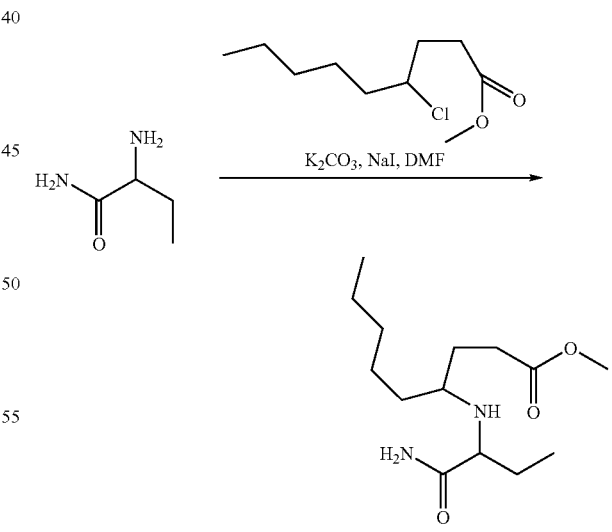

Step 3: Cyclisation: See Conditions of §1.2.2. and §1.2.3.

2.3. Synthesis of keto-pyrrolidin-2-ones

The synthesis of (2S)-2-[2-oxo-4-(2-oxopropyl)-1-pyrrolidinyl]butanamide 230 is representative:

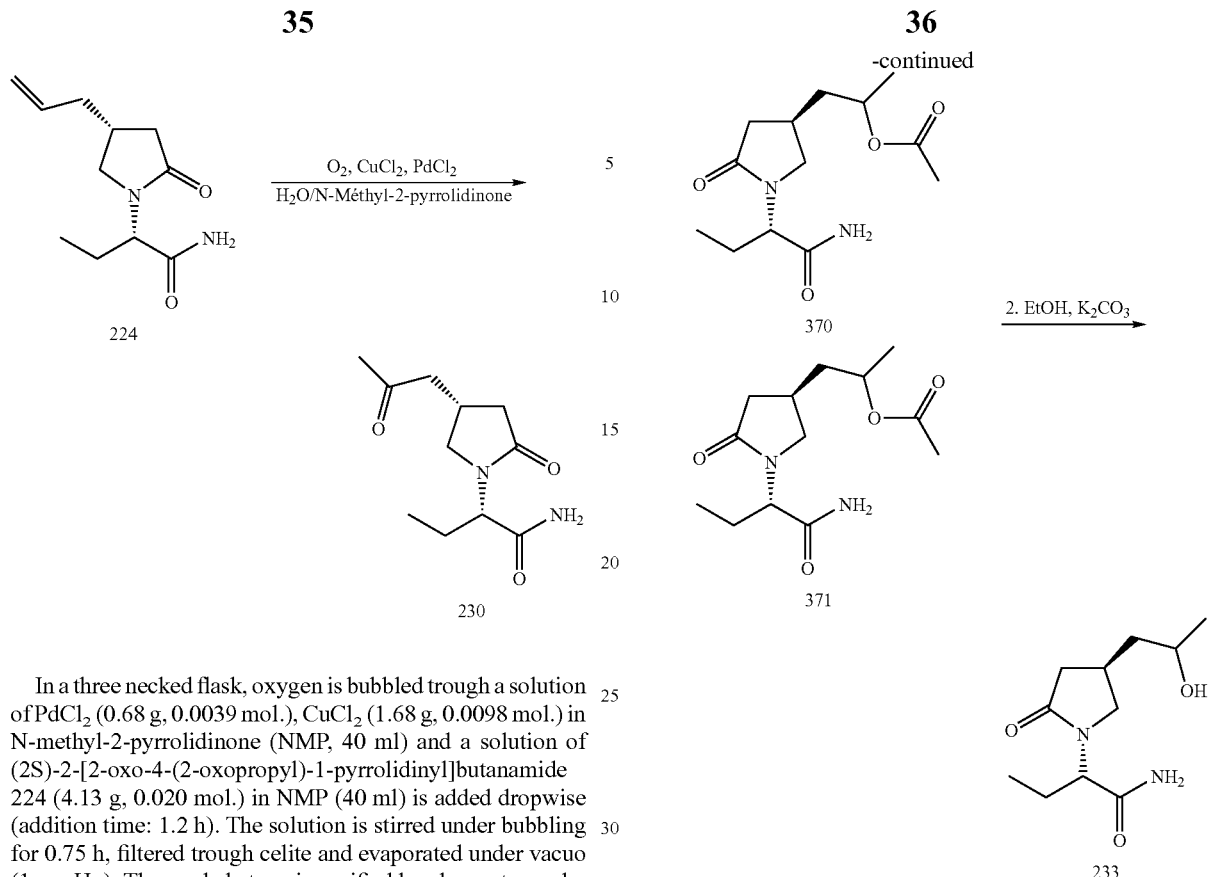

In a three necked flask, oxygen is bubbled trough a solution of PdCl$_2$ (0.68 g, 0.0039 mol.), CuCl$_2$ (1.68 g, 0.0098 mol.) in N-methyl-2-pyrrolidinone (NMP, 40 ml) and a solution of (2S)-2-[2-oxo-4-(2-oxopropyl)-1-pyrrolidinyl]butanamide 224 (4.13 g, 0.020 mol.) in NMP (40 ml) is added dropwise (addition time: 1.2 h). The solution is stirred under bubbling for 0.75 h, filtered trough celite and evaporated under vacuo (1 mmHg). The crude ketone is purified by chromatography on silicagel (CH$_2$Cl$_2$/methyl-t-butyl ether/i-PrOH 9/0.9/0.1 (v/v)) to afford (2S)-2-[2-oxo-4-(2-oxopropyl)-1-pyrrolidinyl]butanamide 230 as a white solid after recrystalisation in AcOEt.

2.4. Derivatisation of Ketone 230

2.4.1. Synthesis of the Alcohols

The synthesis of (2S)-2-[(4S)-4-(2-hydroxypropyl)-2-oxopyrrolidinyl]butanamide 233 is representative:

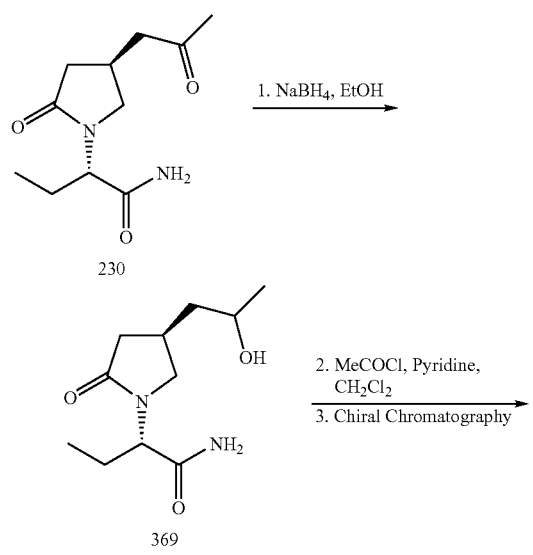

Step 1: Reduction

In a three necked flask, under argon, NaBH$_4$ is added by portions to a solution of 230 (9 g, 0.012 mol.) in EtOH (140 ml) cooled at −5° C. The solution is stirred for 4 h at this temperature, quenched with saturated ammonium chloride and evaporated to dryness. The solid is dissolved in MeOH/CH$_2$Cl$_2$, filtered and concentrated in vacuo. The residue is purified by chromatography on silicagel (MeOH/CH$_2$Cl$_2$: 90/10 (v/v)) to afford the epimeric mixture of alcohols 369 (2.2 g, 79%) as an oil. The crude mixture is directly acetylated in the next step. $^1$H NMR (400 MHz, (CD$_3$)$_2$SO): 0.70 (t, 3H), 1.05 (d, 3H), 1.30-1.45 (m, 1H), 1.70-1.80 (m, 1H), 1.80-2.05 (m, 1H), 2.20-2.40 (m, 2H, partially overlapped with solvent), 3.00-3.20 (m, 1H), 3.30-3.35 (m, 2H, partially overlapped with solvent), 3.50-3.65 (m, 1H), 4.30 (m, 1H), 4.45 (m, 1H), 7.10 (s (broad), 1H), 7.20 (s (broad), 1H).

Step 2: Acetylation

In a three necked flask, under argon, acetyl chloride (0.91 g, 0.011 mol.) is added to a solution of 4-N,N-dimethyl aminopyridine (0.11 g, 0.001 mol.), pyridine (0.86 ml) and the alcohol in CH$_2$Cl$_2$ (90 ml) at room temperature. The solution is stirred for 5 h, quenched with saturated ammonium chloride, and the aqueous layer is extracted with CH$_2$Cl$_2$ (3×) dried over magnesium sulfate and concentrated in vacuo to afford the crude acetate which is purified by column chromatography on chiral phase (hexane/EtOH) to afford the two epimeric acetates 370 and 371 (respectively 1.143 and 1.17 g). For a 1/1 mixture of 370 and 371 before chiral chromatography: $^1$H NMR (400 MHz, CD$_3$SOCD$_3$): 0.90 (t, 3H), 1.21-1.28 (m, 4H), 1.51-1.82 (m, 4H), 1.89-1.98 (m, 1H, 1.80-2.05 (m, 1H), 2.04 (s, 3H), 2.16 (dd, 1H), 2.38 (m, 1H), 2.62 (dd, 1H), 3.11 (dd, 1H); 3.49 (dd, 1H), 4.39-4.49 (m, 1H), 4.89-4.99 (m, 1H), 5.43 (s (broad), 1H), 6.24 (s (broad), 1H).

Step 3: Deacetylation

In a three necked flask, under argon, a suspension of a single enantiomer of the acetate 371 (1.11 g, 0.0042 mol.) and K$_2$CO$_3$ in EtOH is stirred for 20 h at 0° C., evaporated to dryness and the crude alcohol is purified by chromatography on silicagel (MeOH/CH$_2$Cl$_2$: 85/15 (v/v)) to afford (2S)-2-[(4S)-4-(2-hydroxypropyl)-2-oxopyrrolidinyl]butanamide 233 (0.67 g, 72%) as a white solid after recrystallisation in acetonitrile.

2.4.2. Fluorination of 230

Fluorination of the ketone 230 has been used for the synthesis of 2-[(4S)-4-(2,2-difluoropropyl)-2-oxopyrrolidinyl] butanamide 265.

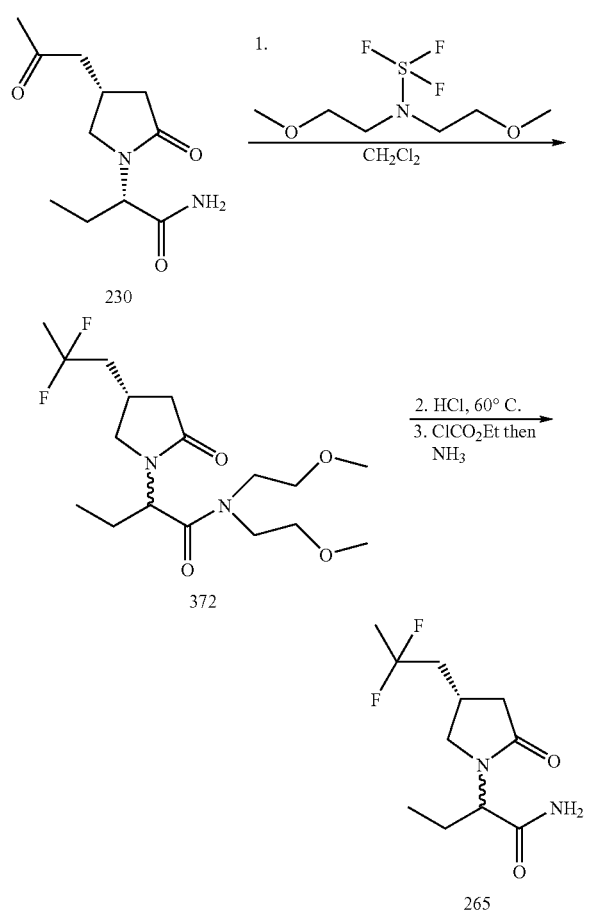

Step 1: Fluorination

In a teflon flask, under argon, (MeOCH$_2$CH$_2$)$_2$NSF$_3$ (1.86 g, 0.009 mol.) is added by portions to a solution of 230 (0.389 g, 0.0017 mol.) in CH$_2$Cl$_2$ and heated 4 h at 80° C. The solution is stirred for 4 h at this temperature, quenched with sodium carbonate, extracted with CH$_2$Cl$_2$, washed with HCl 1N, dried over MgSO4, filtered and concentrated in vacuo to afford the tertiary amide 372 (1.2 g). LC/MS: 365 (MH+). The crude mixture is directly used in the next step.

Step 2: Hydrolysis and Amonolysis.

In a three necked flask under argon, a solution of crude 372 (0.28 g) in HCl 6N is heated for 22 h at 60° C., cooled down to room temperature and the aqueous solution is evaporated to dryness. The solid is triturated in MeCN, filtered and dried under vacuo to afford the acid (1.2 g) as a white solid.

The crude mixture is amidified in the standard conditions described in §6.3.1. (step 2) to afford a mixture of (2S) and (2R)-2-[(4S)-4-(2,2-difluoropropyl)-2-oxopyrrolidinyl]butanamide (respectively 87 and 13%).

2.5. Synthesis of (2S)-2-(2-oxo-4-propyl-1-pyrrolidinyl)butanamide 158 and 159

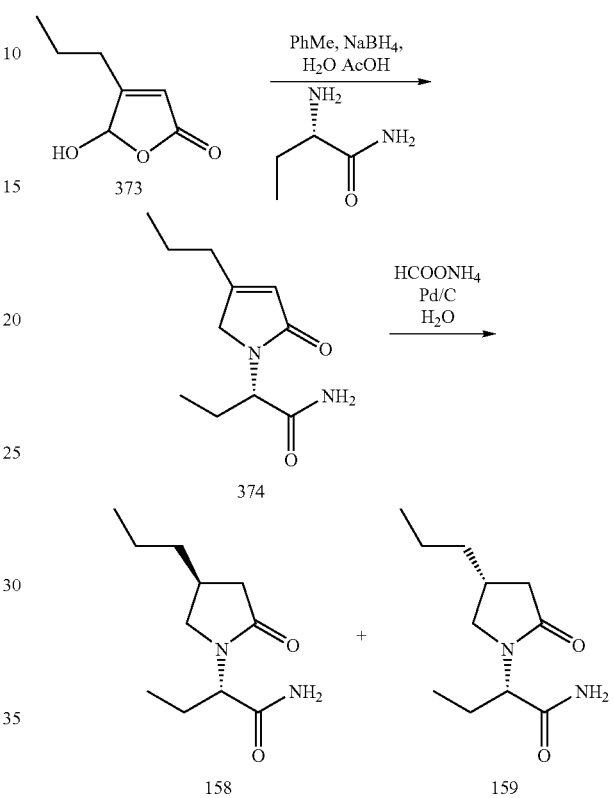

2.5.1. Step 1: Reductive Amination

In a three neck flask, under argon, 4-n-propyl-hydroxy-furanone 373 (35.5 g, 0.25 mol. synthesized from Bourguignon J J et al; *J. Med Chem,* 1988, 31, 893-897) is added a solution of S-2-aminobutyramide (28.1 g, 0.275 mol.) in PhMe (355 ml) at 18° C. The solution is stirred for 0.5 h at this temperature and a precipitate appears. The reaction mixture is stirred for 2 h and NaOH 4N (37.5 ml) is added dropwise to the suspension followed by an aqueous solution of NaBH$_4$ (6.2 g, 0.16 mol.) in water (62 ml). After 1 h, the reaction mixture is carefully quenched with AcOH (30 ml), heated to 50° C. for 3 h and cooled to room temperature overnight. NaOH 50% w/w is added (20 ml) and the aqueous phase is extracted with PhMe (2×). The organic phases are combined, washed with brine and concentrated in vacuo to afford the crude unsaturated pyrrolidone 374 (43.4 g) as an orange oil which is used in the next step without any further purification. It can be recrystallized into a white solid (DSC, onset: Mp=72.9° C.).

2.5.2. Step 2: Hydrogenolysis

In a three necked flask, under argon, an aqueous solution of NH$_4$COOH (8 g, 0.126 mol.) is added by portions to a suspension of the crude 374 (22 g, 0.105 mol.) and 10% Pd/C (1.1 g) in water (220 ml) heated at 50° C. The suspension is stirred for 3 h at 50° C., cooled to room temperature and stirred overnight. After 18 h, the suspension is heated at 50° C. and an aqueous solution of NH₄COOH (8 g, 0.126 mol.) is added by portions. After 1.5 h a third portion of an aqueous solution of NH₄COOH (8 g, 0.126 mol.) is added. The suspension is stirred for 0.5 h at 50° C. and 10% Pd/C (1.1 g) is added. The suspension is stirred for 5 h at this temperature and left overnight without stirring at room temperature. The reaction mixture is filtered over celite, washed with water (30 ml) and the aqueous layer is extracted with AcOEt (3×). The combined organic phases are washed with brine and concentrated in vacuo to afford the crude pyrrolidone as white crystals (18.1 g). The two diastereoisomers are separated by preparative HPLC on chiral phase (EtOH/heptane: 1/1) to afford, after recrystallisation in iPr₂O, the two pyrrolidones 158 (9.5 g) and 159 (7.2 g) as white solids.

Two solid state form of 159 have been observed, namely form A and form B. The form A is typically characterized by diffraction peaks at 8.8, 9.8, 14.9, 15.0, 17.0, 17.1, 21.2, 21.4, 24.8 (2θ°). The form B is typically characterized by diffraction peaks at 6.50, 11.25, 19.22, 23.44, 28.47, 29.94 (2θ°).

2.5.3. Synthesis of 5-hydroxy-4-propyl-furan-2-one

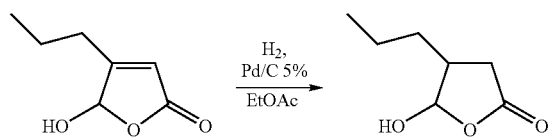

5-hydroxy-4-propyl-5H-furan-2-one 373 (15 g, 0.1 mol), ethyl acetate (260 ml) and Pd/C5% are placed in a Parr apparatus. The mixture is degassed, and hydrogen is introduced at a pressure of 35 psi. This mixture is then stirred vigorously at 25° C. for 2 h. After filtration on celite, the solvent is removed under reduced pressure at 50° C. to give the 5-hydroxy-4-propyl-furan-2-one as a crude product (100% yield). LC/MS: 145 (MH+).

EXAMPLE 3

Synthesis of 4-substituted 2-oxo-pyrrolidine butanamides by Alkylation of a 2-oxo-pyrrolidine with ethyl 2-bromo-butanoate 3.1. Synthesis of 4-substituted 2-oxo-pyrrolidines 3.1.1.a.1. Preparation of ethyl 3-(3-chlorophenyl)-2-propenoate 375

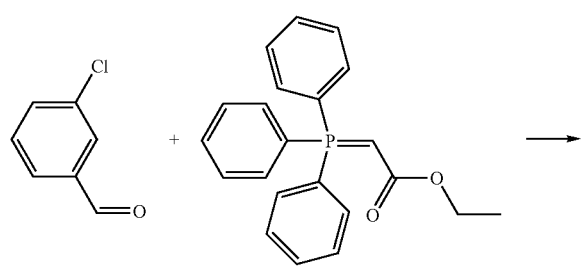

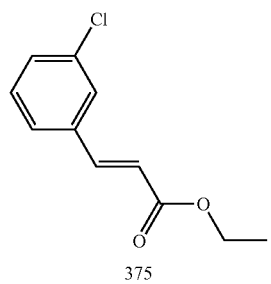

In a 2 l three necked flask fitted with mechanical stirrer and dropping funnel under inert atmosphere, 106.2 g (755 mmoles, 1 eq) of 3-chlorobenzaldehyde are dissolved in 1 l of THF and cooled down to 0° C. 341.9 g (980 mmoles, 1.3 eq) of ethyl (triphenylphosphoranylidene)acetate are then added under efficient stirring, the temperature raising to 10° C. The mixture is kept under stirring one hour at 0° C., and then overnight at room temperature. The mixture is concentrated to dryness, the residue suspended in diethyl ether, the triphenylphosphine oxide is filtered off and the filtrate concentrated to dryness. The residue is purified by PrepLC (1 kg SiO₂, pet. ether/EtOAc, 75:35) to give 191.8 g of pure 375, 92% yield. ¹H NMR (250 MHz, (CD₃)₂SO): 1.30 (t, 3H), 4.25 (q, 2H), 6.70 (d, 1H), 7.40 (m, 2H), 7.50-7.70 (m, 2H), 7.85 (s(broad), 1H).

3.1.1.a.2. Other Methods

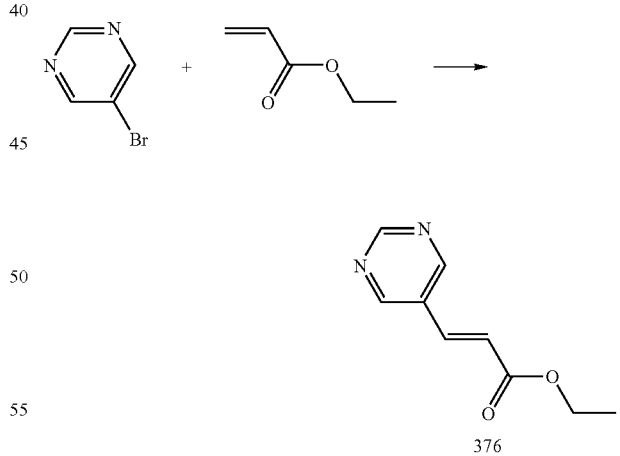

Alternatively, cinnamate derivatives have also been synthesized by Palladium catalyzed carbometalation of an acrylic derivative. For example, ethyl (2E)-3-(5-pyrimidinyl)-2-propenoate 376 is obtained by reaction between ethyl acrylate and 5-bromopyrimidine in the presence of palladium acetate.

3.1.1.b. Preparation of ethyl 3-(3-chlorophenyl)-4-nitrobutanate 377

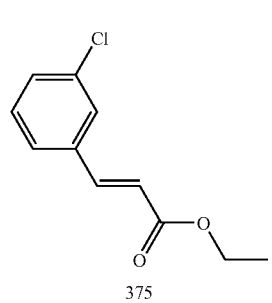
375

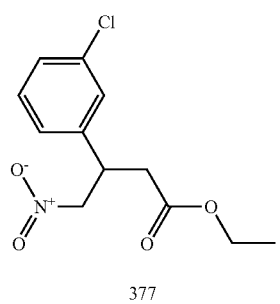
377

In a 500 ml three necked flask fitted with reflux condenser, magnetic stirrer and dropping funnel under inert atmosphere, 100 g (447 mmoles, 1 eq) of ethyl 3-(3-chlorophenyl)-2-propenoate 375 are dissolved in 127 ml (2.37 moles, 5 eq) of nitromethane. 70.9 ml (447 mmoles, 1 eq) of diazabicycloundecene are then added dropwise under efficient stirring, keeping the temperature below 25° C. (ice/water bath). The deep red mixture is stirred overnight at room temperature. The mixture is diluted with diethyl ether, washed with 1N HCl, the aqueous phase reextracted twice with ethyl ether. The combined organic phases are dried over magnesium sulfate, filtered and concentrated to dryness to give 128.5 g of crude 377, 99% yield, used as such in the next step. $^1$H NMR (250 MHz, (CD$_3$)$_2$SO): 1.10 (t, 3H), 2.70 (dd, 1H), 2.75 (dd, 1H), 3.95 (q, 2H), 4.95 (m, 2H), 7.20-7.45 (m, 4H).

3.1.1.c. Preparation of ethyl 4-amino-3-(3-chlorophenyl)butanoate 378

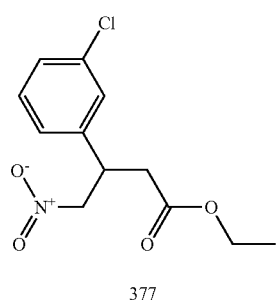
377

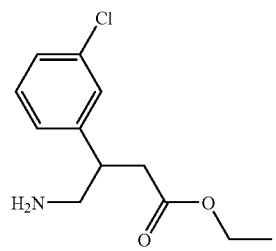
378

In a 2 L pressure jar, under inert atmosphere, 196 g (733 mmoles) of ethyl 3-(3-chlorophenyl)-4-nitrobutanoate 377 are dissolved in 200 ml of ethanol. A suspension of 200 g of predried (3×, ethanol) Raney Nickel in 700 ml of ethanol is added and the mixture hydrogenated on a Parr hydrogenator at a maximum of 20 psi H$_2$ pressure (STRONGLY EXOTHERMIC REACTION, ice/water cooling required). The mixture is degassed, filtered on a Celite/Norite pad, and the filtrate concentrated in vacuo, to give 136.7 g of crude 378, 78% yield, used as such in the next step.

3.1.1.d. Preparation of 4-(3-chlorophenyl)-2-pyrrolidinone 379

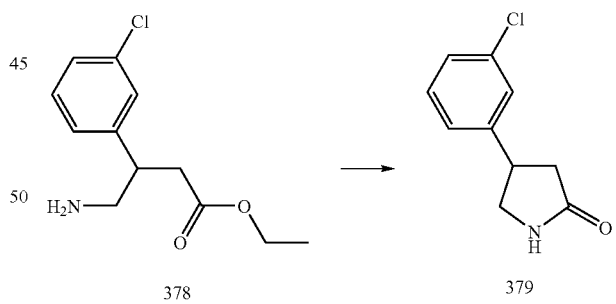

In a 500 ml flask fitted with reflux condenser and magnetic stirrer, 135.7 g (561 mmoles) of ethyl 4-amino-3-(3-chlorophenyl)butanoate 378 are dissolved in 200 ml of toluene, and the mixture is refluxed for 30 min. The solution is concentrated to dryness and the residue purified by PrepLC (1 kg SiO$_2$, CH$_2$Cl$_2$/EtOH, 98:2->95:5) to give 54.4 g of pure 379 (49.2%). GC/MS: 197/197 M+.

3.1.1.f. Preparation of ethyl 2-[4-(3-chlorophenyl)-2-oxo-1-pyrrolidinyl]butanoate 380

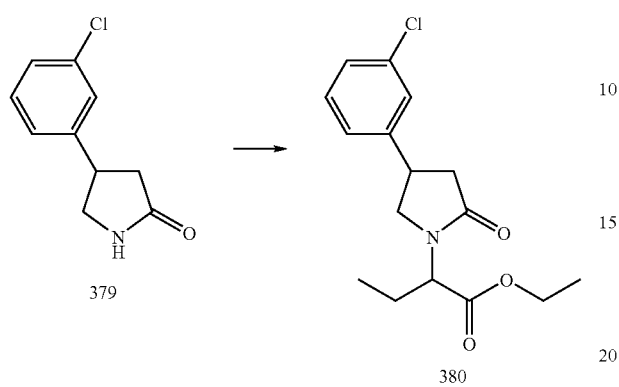

In a 2 l three necked flask fitted with reflux condenser, magnetic stirrer and dropping funnel under inert atmosphere, 54.4 g (278 mmoles, 1 eq) of 4-(3-chlorophenyl)-2-pyrrolidinone 379 are dissolved in 1.4 l acetonitrile. 64 ml (100.7 g, 556 mmoles, 2 eq) of methyl 2-bromobutanoate are added and the temperature raised to 50° C. 22.24 g (556 mmoles, 2 eq) of sodium hydride are added by portions, the temperature raising to 65° C. The mixture is stirred one more hour at 50° C. The mixture is concentrated to dryness, the residue suspended in ethyl acetate, washed with water, the aqueous phase reextracted with ethyl acetate. The combined organic phases are dried over magnesium sulfate, filtered and concentrated to dryness. The residue is purified by PrepLC (1 kg $SiO_2$, pet. ether/EtOAc, 70:30) to give 56.7 g of pure 380, 69%. $^1$H NMR (250 MHz, $(CD_3)_2SO$): 0.80-1.00 (m, 3H), 1.60-1.90 (2H, m), 2.35-2.55 (m, 1H: partially overlapped with solvent), 2.60-2.90 (m, 1H: partially overlapped with solvent), 3.70 (s, 3H), 3.50-3.80 (m, 3H), 4.50 (m, 1H), 7.20-7.50 (m, 4H).

3.1.1.g. Preparation of 2-[4-(3-chlorophenyl)-2-oxo-1-pyrrolidinyl]butanamide 381

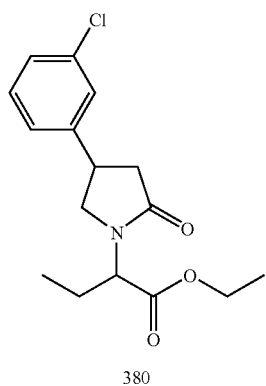

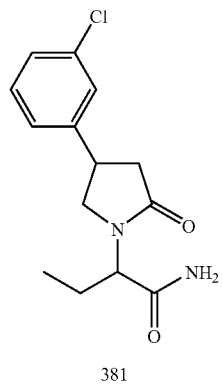

In a 1 l three necked flask fitted with reflux condenser, magnetic stirrer and, 56.7 g (192 mmoles) of ethyl 2-[4-(3-chlorophenyl)-2-oxo-1-pyrrolidinyl]butanoate 380 are dissolved in 600 ml of methanol. Gaseous ammonia is bubbled through the solution, and the saturated solution kept at room temperature for 5 days, while occasionally resaturating with ammonia. After completion of the reaction, the solution is concentrated to dryness. The residue is purified by PrepLC (1 kg $SiO_2$, $CH_2Cl_2$/EtOH, 97:3) to give 50 g of pure 381, 97.8%. 82.2 g of the mixture of diastereomers are separated by Chiral PrepLC (Chiralpak AD, benzine/EtOH, 50:50), and each pair of enantiomers resolved by Chiral PrepLC (Chiralpak AD, benzine/EtOH, 50:50). The four compounds are crystallised from toluene to give 16.79 g, 13.9 g, 15.84 g, and 14.84 g of 202, 203, 204 and 205 respectively, 72% overall.

EXAMPLE 4

Synthesis of 4-substituted 2-oxo-pyrrolidine butanamides by Alkylation/Cyclisation of 4-bromo-3-substituted-but-2-enoic acid Esters with 2-amino-butanamides

4.1. Synthesis of 4-bromo-3-substituted-but-2-enoic acid Ester, Alkylation and Reduction

4.1.1 Bromination of 3-substituted crotonic acid ethyl esters

The synthesis of 4-bromo-3-(2-thiophenyl)-but-2-enoic acid ethyl ester 382 is representative:

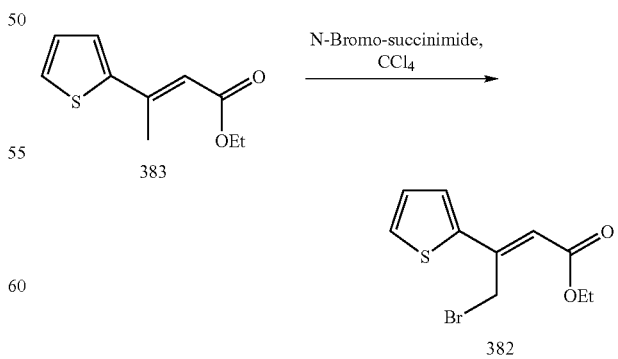

In a 2 L three necked flask under argon with mechanical stirring, a degassed solution of 2-thiophen-3-yl-but-2-enoic-acid ethyl ester 383 (32.88 g, 0.211 mol.), N-bromosuccinimide (37.56 g, 0.211 mol.) and 2,2'-aza-bis-isobutyronitrile (3.46 g, 0.021 mol.) in CCl$_4$ (600 ml) is refluxed for 6 h, cooled to room temperature and stirred for 20 h. The suspension is filtered and concentrated in vacuo to afford the crude bromide which by is purified by chromatography on silicagel (Hexane/CH$_2$Cl$_2$: 65/35 (v/v)) to afford 4-bromo-3-(2-thiophenyl)-but-2-enoic acid ethyl ester 382 (36.72 g, 78%). $^1$H NMR (250 MHz, (CDCl$_3$): 3.80 (s, 3H), 4.95 (s, 2H), 6.25 (s, 1H), 7.10 (dd, 1H), 7.35 (d, 1H), 7.45 (d, 1H).

4.1.2 Alkylation with 2-amino-butanamide

The synthesis of 2-[2-oxo-4-(2-thienyl)-1-pyrrolidinyl]butanamide 71 is representative:

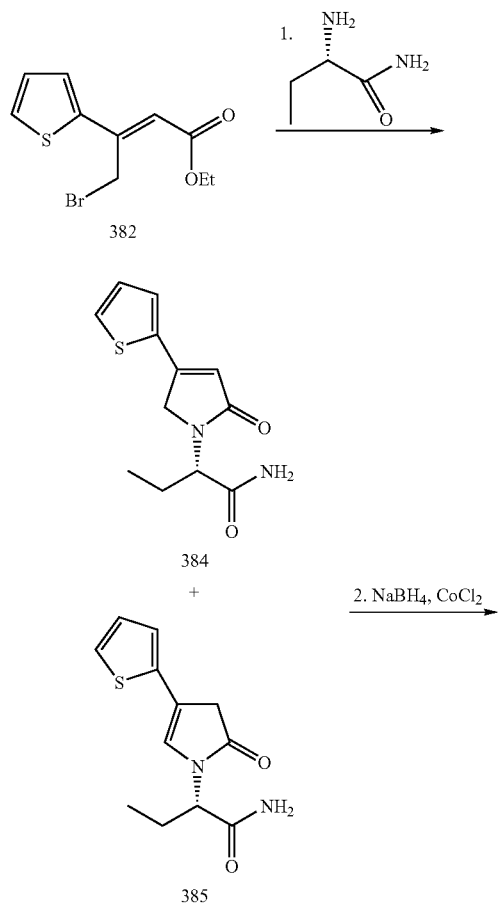

4.1.2.1. Step 1: Alkylation-Cyclisation

In a 1 L three necked flask under argon, a solution of 4-bromo-2-thiophen-3-yl-but-2-enoic-acid methyl ester 382 (36.72 g, 0.134 mol.), (S)-2-amino-butyramide ([α]$^{25}_D$: 19.09°; 31.6 g, 0.270 mol.) in THF (350 ml) is stirred for 20 h at room temperature. The suspension is filtered and concentrated in vacuo to afford the crude unsaturated pyrrolidones 384 and 385 (43.47 g) which are used in the next step without any further purification. The crude pyrrolidone can be isolated and is usually a mixture of double bond isomers (olefin in 3,4 and 4,5, the first one being the major one). $^1$H NMR (250 MHz, (CD$_3$)$_2$SO): 0.80 (t, 3H), 1.30-1.90 (m, 2H), 4.40 (d, 1H), 4.45 (m, 1H), 4.70 (d, 1H), 6.30 (s, 2H), 7.0 (s (broad), 1H), 7.15 (dd, 1H), 7.40 (s (broad), 1H), 7.50 (d, 1H), 7.85 (d, 1H).

4.1.2.2. Step 2: Reduction

In a 0.5 L three necked flask under argon, NaBH$_4$ (1.75 g, 0.044 mol.) is added by portions to a solution of the crude unsaturated pyrrolidone 384/385 (14 g, 0.044 mol.), CoCl$_2$ (0.062 g, 0.0005 mol.) in EtOH (100 ml)-diethylene glycol dimethyl ether (65 ml) cooled at 0° C. After 0.75 h, the reaction mixture is heated to reflux for 48 h and during that time successively three portions of NaBH$_4$ (1.75 g, 0.045 mol.) and CoCl$_2$ (0.062 g, 0.0005 mol.) are added every 10 h until the disappearance of the starting material. The reaction mixture is cooled to room temperature, hydrolyzed with saturated ammonium chloride, extracted with AcOEt, dried over magnesium sulfate, and concentrated in vacuo to afford the crude pyrrolidone which is purified by column chromatography on silicagel (CH$_2$Cl$_2$/MeOH: 97/03 (v/v)) to afford 4.15 g of 2-[2-oxo-4-(2-thienyl)-1-pyrrolidinyl]butanamide (38%). The mixture of stereoisomers is purified by column chromatography on chiral phase (hexane/EtOH) to afford the two diastereoisomers (2S)-2-[2-oxo-4-(2-thienyl)-1-pyrrolidinyl]butanamide 71 (recrystallised in AcOEt) and 72 (recrystallised in AcOEt). In this particular case, two minor impurities, namely the two diastereoisomers of (2R)-2-[2-oxo-4-(2-thienyl)-1-pyrrolidinyl]butanamide 84 (0.25 g, recrystallised in AcOEt) and 85 (0.44 g, recrystallised in AcOEt) are also obtained during the purification.

4.2. Synthesis of Azidophenyl Pyrrolidones

The synthesis of the single enantiomer of (2S)-2-[4-(3-azidophenyl)-2-oxo-1-pyrrolidinyl]butanamide 86 is representative:

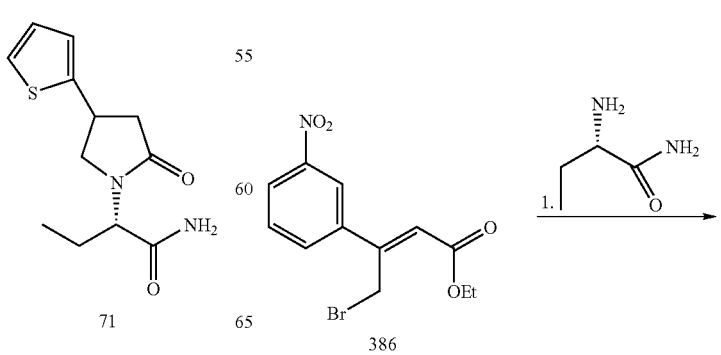

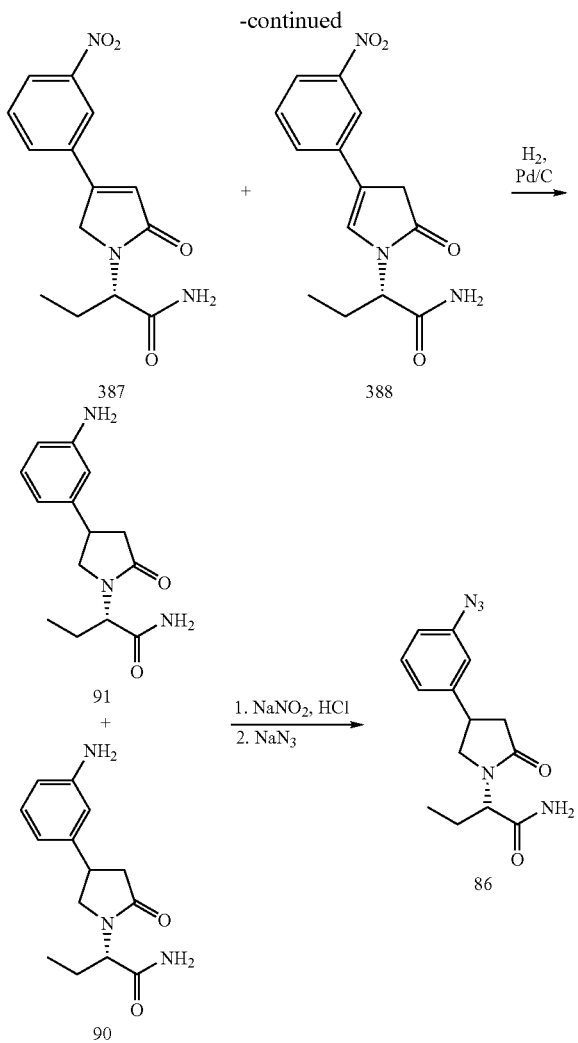

4.2.1. Synthesis of Anilines

4.2.1.1. Step 1: Alkylation of (S)-2-amino-butyramide by 4-bromo-3-(3-nitrophenyl)-but-2-enoic-acid methyl ester 386

The synthesis of 386 is made as described in §4.1.1. $^1$H NMR (250 MHz, (CD$_3$)$_2$SO): 1.30 (t, 3H), 4.20 (q, 2H), 5.15 (s, 2H), 6.45 (s, 1H), 7.75 (dd, 1H), 8.10 (dd, 1H), 8.25 (dd, 1H), 8.45 (d, 1H).

The alkylation is performed following the experimental procedure described in §4.1.2.1. (59%). LC/MS: 290 (MH+).

4.2.1.2. Step 2: Reduction

In a 2.5 L pressure jar, under inert atmosphere, 7.22 g (0.025 mol.) of 387 and Pd on charcoal (10% w/w, 0.2 g) are dissolved in EtOH (1 l) and the mixture hydrogenated on a Parr hydrogenator at a maximum of 20 psi H$_2$ pressure. After 1 h, the mixture is degassed, filtered on a Celite/Norite pad, and the filtrate concentrated in vacuo, to afford the crude pyrrolidone which is purified by column chromatography on silicagel (CH$_2$Cl$_2$/MeOH: 93/07 (v/v)) to afford the mixture of diastereoisomers which are purified by column chromatography on chiral phase (hexane/EtOH) to afford, after reac- tion with HCl in EtOH (for the synthesis of the hydrochloride) the two diastereoisomers of (2S)-2-[4-(3-aminophenyl)-2-oxo-1-pyrrolidinyl]butanamide 90 (0.800 g, recrystallised in EtOH) and 91 (1.21 g, recrystallised in EtOH) as their hydrochloride salts.

4.2.2. Synthesis of the Phenylazido 86.

In a three necked flask, under argon, a solution of NaNO$_2$ (0.232 g, 0.0037 mol.) in water (1.5 ml) is added dropwise to a solution of the free base of (2S)-2-[4-(3-aminophenyl)-2-oxo-1-pyrrolidinyl]butanamide 90 (0.8 g, 0.0031 mol.) in HCl 10 M (6.5 ml) cooled at 0° C. After 0.5 h at room temperature, NaN$_3$ (0.220 g, 0.0037 mol.) in water (2 ml) is added and the resulting solution is stirred for 0.5 h at 0° C. The reaction mixture is quenched with NaOH (33% w/w) and diluted by EtOAc. The aqueous phase is acidified to pH 5-6 and extracted with EtOAc. The combined organic phases are dried over magnesium sulfate and concentrated in vacuo to afford the crude pyrrolidone which is purified by column chromatography on silicagel (CH$_2$Cl$_2$/MeOH: 97/03 (v/v)) to afford, after recrystalllisation in MeCN, 0.42 g of a single enantiomer of (2S)-2-[2-oxo-4-(3-azidophenyl)-1-pyrrolidinyl]butanamide 86 (48%).

4.3. Synthesis of (2S)-2-[4-(3-amino-2,4,6-tribromophenyl)-2-oxo-1 pyrrolidinyl]butanamide 107

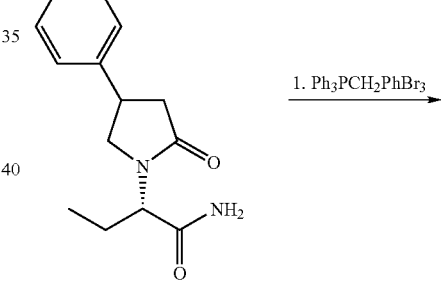

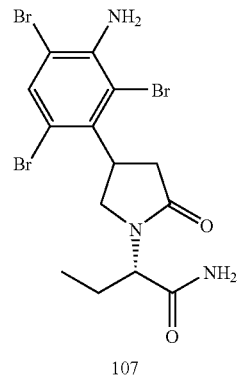

In a three necked flask, under argon, a solution of Ph$_3$PCH$_2$PhBr$_3$ (2.870 g, 0.048 mol.) and 90 (0.420 g, 0.0016 mol.) in CH$_2$Cl$_2$ (10 ml) and MeOH (5 ml) is stirred with NaHCO$_3$ (0.407 g, 0.048 mol.) for 4 h at room temperature (orange solution). The reaction mixture is filtered and concentrated in vacuo to afford the crude aniline which is purified by column chromatography on silicagel (AcOEt/ethanol 98/02 (v/v)) to afford 0.38 g of the expected aniline 107 (47%, recrystallized from Et₂O).

4.4. Synthesis of (2S)-2-[4-methyl-2-oxo-1-pyrrolidinyl]butanamide 35 and 36

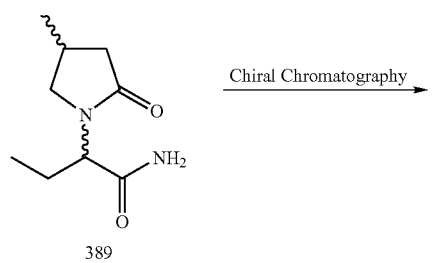

389

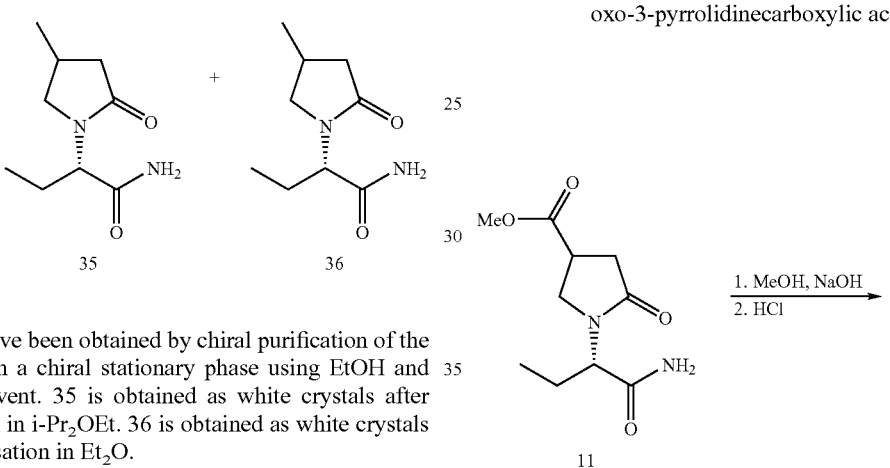

35    36

35 and 36 have been obtained by chiral purification of the racemic 389 on a chiral stationary phase using EtOH and Hexane as solvent. 35 is obtained as white crystals after recrystalisation in i-Pr₂OEt. 36 is obtained as white crystals after recrystalisation in Et₂O.

EXAMPLE 5

Synthesis of 4-substituted 2-oxo-pyrrolidine butanamides by Derivatisation of methyl 1-[1-(aminocarbonyl)propyl]-5-oxo-3-pyrrolidinecarboxylate 11

5.1. Synthesis of methyl 1-[1-(aminocarbonyl)propyl]-5-oxo-3-pyrrolidinecarboxylate 11/12

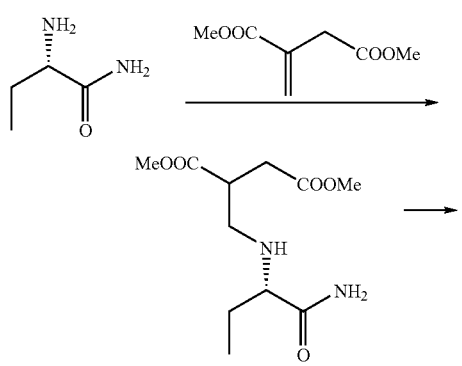

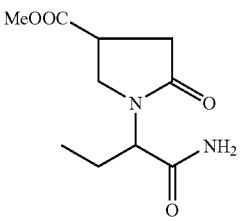

This transformation is described elsewhere §7.0.1 to produce the two esters 11 and 12.

5.2. Synthesis of 1-[2S-1-(aminocarbonyl)propyl]5-oxo-3-pyrrolidinecarboxylic acid 48

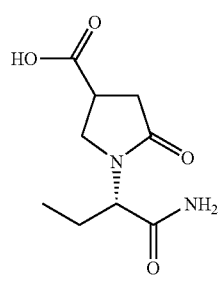

11

1. MeOH, NaOH
2. HCl

48

In a three necked flask, under argon, a solution of 1N NaOH (126 ml) is added to a solution of the enantiomerically pure ester 11 (22.62 g, 0.1 mol.) in MeOH cooled at 0° C. After 1.5 h at this temperature, the reaction is acidified by HCl (1N (109 ml), the solvents evaporated under vacuum. The residue is extracted with i-PrOH, filtered and the filtrate is concentrated in vacuo to afford the crude acid (17.82 g) which is recrystallised from MeCN to produce the enantiomerically pure 1-[2S-(aminocarbonyl)propyl]-5-oxo-3-pyrrolidinecarboxylic acid 48.

5.3. Synthesis of (2S)-2-[4-(1,3,4-oxadiazol-2-yl-2-oxo-1-pyrrolidinyl]butanamide 50

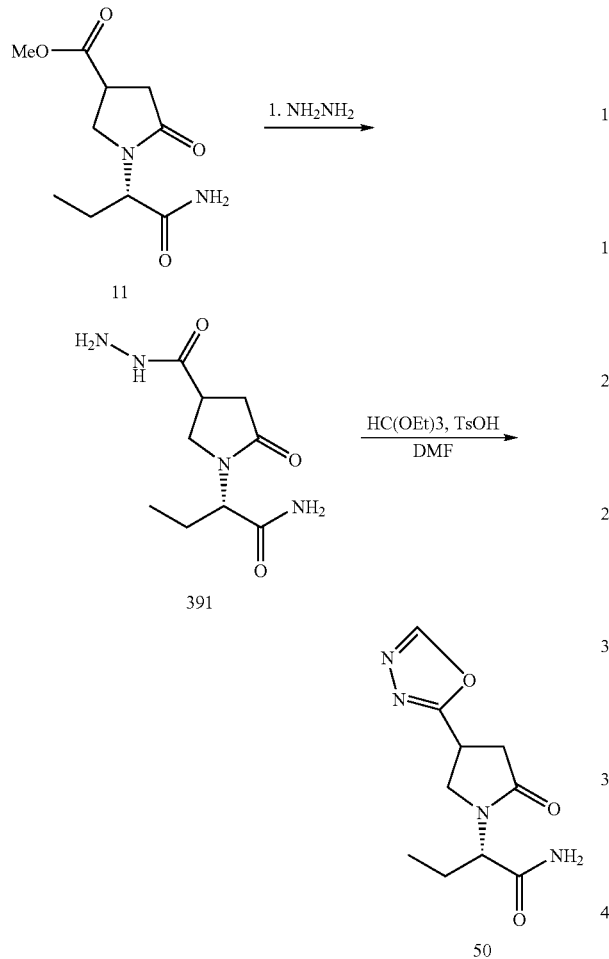

Step 1: Reaction with Hydrazine

In a three necked flask, under argon, a solution of the ester 11 (3 g, 0.013 mol.) and hydrazine hydrate (0.7 ml) is stirred in EtOH (3 ml) for 24 h. The yellow solution is then concentrated to afford the crude hydrazide 391 which crystallise upon standing (2.37 g, 79%). GC/MS: 228 (M+).

Step 2: Synthesis of the Oxadiazole

In a three necked flask, under argon, a solution of the crude hydrazide 391 (this patent, 3 g, 0.013 mol.), triethyl orthoformate (2 ml) and p-toluene sulfonic acid (0.010 g) is heated at 110° C. for 24 h. The reaction mixture is cooled to room temperature, concentrated under vacuo to afford the crude oxadiazole which is purified by chromatography on silicagel (CH$_2$Cl$_2$/MeOH: 95/05 (v/v)) to afford (2S)-2-[4-(1,3,4-oxadiazol-2-yl)-2-oxo-1-pyrrolidinyl]butanamide 50 (0.312 g) as an oil.

5.4. Synthesis of 1,3,4-oxadiazole Derivatives

Alternatively, 1,3,4-oxadiazole derivatives can be obtained from hydrazine 391. For example, 2-[2-oxo-4-(5-sulfanyl-1, 3,4-oxadiazol-2-yl)-1-pyrrolidinyl]butanamide 51 is obtained by reacting hydrazine 391 with CS2 and KOH in EtOH.

5.5. Synthesis of 4-amino-pyrrolidin-2-one 392

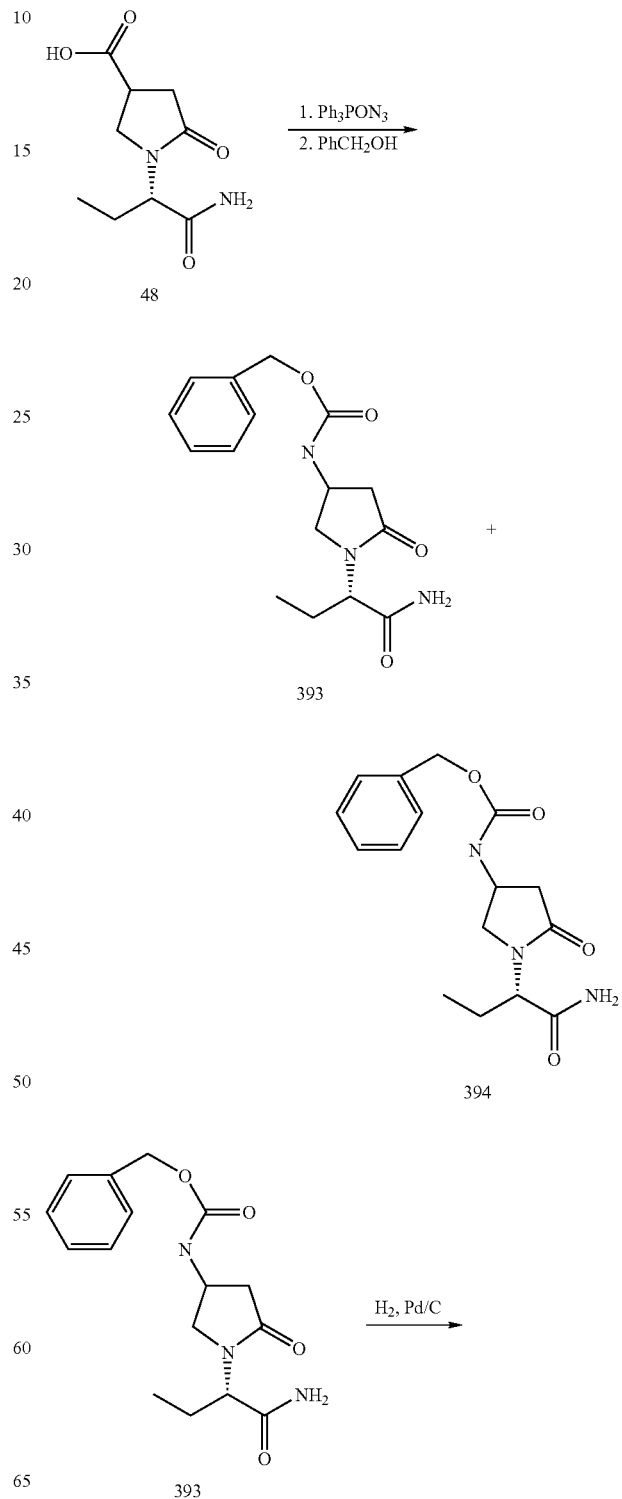

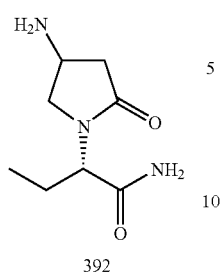

392

5.5.1. Step 1: Synthesis of the Carbamate 393

In a three necked flask, under argon, a solution of the enantiomerically pure 1-[2S-1-(aminocarbonyl)propyl]-5-oxo-3-pyrrolidinecarboxylic acid 48 (19.06 g, 0.089 mol.), diphenylphosphoryl azide (26.9 g, 0.097 mol.) and Et₃N (13.5 ml) in MeCN (225 ml) is heated at 55° C. with formation of N₂. The temperature is kept at 55° C. for 0.5 h at 70° C. for 2 h and cooled down to room temperature. Benzyl alcohol (9.25 ml) is added and the solution is refluxed for 4 h, cooled down to room temperature and concentrated in vacuo. The crude carbamate is purified by chromatography on silicagel (AcOEt/MeOH/NH₄OH: 95/04/01 (v/v/v)) to afford the two diastereoisomeric carbamates 394 (2.64 g, 9.3%) and 393 (11.9 g, 42%). For 393: ¹H NMR (250 MHz, CDCl₃): 0.90 (t, 3H), 1.30-1.90 (m, 2H), 2.35 (dd, 1H), 2.75 (dd, 1H), 3.30 (dd, 1H), 3.75 (m, 1H), 4.30-4.50 (m, 2H), 5.10 (s, 2H), 5.35 (s (broad), 1H), 5.55 (s (broad), 1H), 6.40 (s (broad), 1H), 7.30-7.45 (m, 5H).

5.5.2. Step 2: Synthesis of 4-amino-pyrrolidin-2-one 392

In a 0.25 L pressure jar, under inert atmosphere, 11.9 g (0.037 mmol.) of 393 and Pd on charcoal (10% w/w, 0.2 g) are dissolved in EtOH (300 ml) and the mixture hydrogenated on a Parr hydrogenator at a maximum of 20 psi H₂ pressure. After 20 h, the mixture is degassed, filtered on a Celite/Norite pad, and the filtrate concentrated in vacuo, to give the crude amine which is recrystallised from PhMe to afford 2-[4-amino-2-oxo-1-pyrrolidinyl]butanamide 392 (6.99 g, quantitative).

5.6. Synthesis of 4-pyrol-pyrrolidin-2-one 223

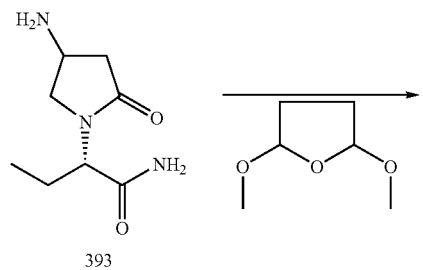

393

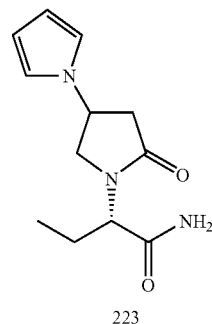

223

In a three necked flask, under argon, a suspension of 2-[4-amino-2-oxo-1-pyrrolidinyl]butanamide 393 (6.99 g, 0.037 mol.), dimethoxytetrahydrofurane (5.53 g, 0.041 mol.), pyridine (50.6 ml) and AcOH (36 ml) is warmed to 70° C. and dissolution occurs. After 2 h at this temperature, the reaction is cooled down to room temperature, concentrated in vacuo and the crude product is purified by chromatography on silicagel (CH₂Cl₂/MeOH: 95/05 (v/v)) to afford 223 as an oil (2.67 g, 30.1%).

5.7. Bromination of 4-pyrrolyl-pyrrolidin-2-one 223

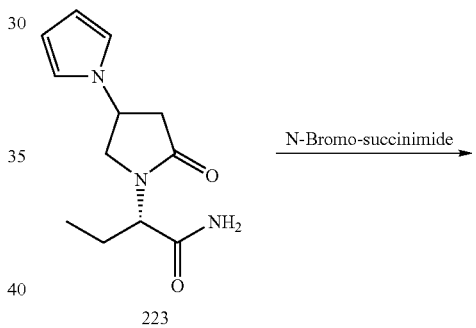

223

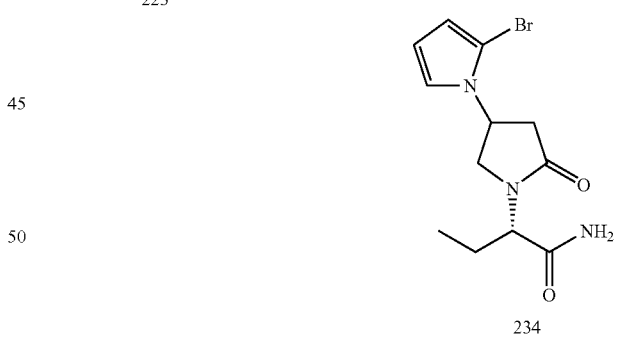

234

In a 0.25 L three necked flask under argon with magnetic stirring, a degassed solution of 2S-4-pyrol-pyrrolidin-2-one 223 as a single enantiomer (1.18 g, 0.0049 mol.) in THF (35 ml) is cooled to −78° C. and N-Bromosuccinimide (0.877 g, 0.005 mol.) is added by portions. The reaction mixture is stirred for 0.5 h, and the Na₂S₂O₃ (0.9 g) is added to quench the NBS. The reaction mixture is warmed to room temperature, concentrated in vacuo and purified by chromatography on silicagel (EtOH/CH₂Cl₂: 05/95 (v/v)) to afford, after recrystallisation in MeCN, (2S)-2-[4-(2-bromo-1H-pyrrol-1-yl)-2-oxo-1-pyrrolidinyl]butanamide 234 (1.05 g, 67%) as a white solid.

Alternatively, using the same experimental procedure and 2 equiv. of N-Bromo-succinimide, dibromopyrrole 237 can be obtained.

5.8. Synthesis of Tetrazolyl Derivatives

Alternatively to §5.6, reaction of 2-[4-amino-2-oxo-1-pyrrolidinyl]butanamide with triethyl orthoformate, NaN₃ and AcOH provided 2-[2-oxo-4-(1H-tetrazol-1-yl)-1-pyrrolidinyl]butanamide 67.

5.9. Synthesis of (4H-1,2,4-triazol-4-yl) Derivatives

Alternatively to §5.6, reaction of 2-[4-amino-2-oxo-1-pyrrolidinyl]butanamides with pyridine and 1,2-bis((dimethylamino)methylene)hydrazine provided 2-[2-oxo-4-(4H-1,2,4-triazol-4-yl)-1-pyrrolidinyl]butanamides 65 and 66.

EXAMPLE 6

Synthesis of 4-substituted 2-oxo-pyrrolidine butanamides by Olefination of 1-[1-(tertbutoxycarbonyl)propyl]-5-oxo-3-pyrrolidinecarboxaldehyde 396

6.1. Synthesis of 1-[1-(tertbutoxycarbonyl)propyl]-5-oxo-3-pyrrolidinecarboxaldehyde 396

Step 1: Condensation of 2-amino butyrate with Methyl Itaconate

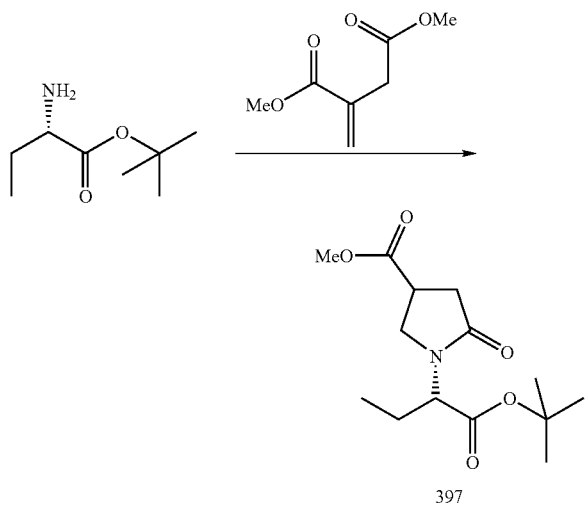

In a one liter three necked flask, under argon, a solution of 2,2-dimethylethyl (S)-2-amino-butanoate (commercially available, 46.6 g, 0.268 mol.) and dimethyl itaconate (83 ml, 0.59 mol.) is refluxed in MeOH (400 ml) for 20 h. The mixture is stirred at room temperature for 20 h, concentrated in vacuo and the residue is purified by chromatography on silicagel (CH₂Cl₂/MeOH: 97/3 (v/v)) to afford methyl 1-[(1S)-1-(tertbutoxycarbonyl)propyl]-5-oxo-3-pyrrolidinecarboxylate 397 (81.6 g, quantitative). Analysis of a 1/1 mixture methyl 1-[(1S)-1-(tertbutoxycarbonyl)propyl]-5-oxo-3-pyrrolidinecarboxylate 397: ¹H NMR (250 MHz, (CD₃)₂SO): 1.05 (t, 3H), 1.44 (s, 9H), 1.60-1.65 (m, 1H), 1.65-1.90 (m, 1H), 2.40-2.65 (m, 2H partially overlapped with solvent signals), 3.30-3.65 (m, 3H), 3.70 (s, 3H), 4.40 (dd, 1H).

Alternatively, the reaction can also be conducted with racemic 2,2-dimethylethyl-2-amino-butanoate to afford the racemic butanamide with a similar yield.

Step 2: Synthesis of the Aldehyde 396

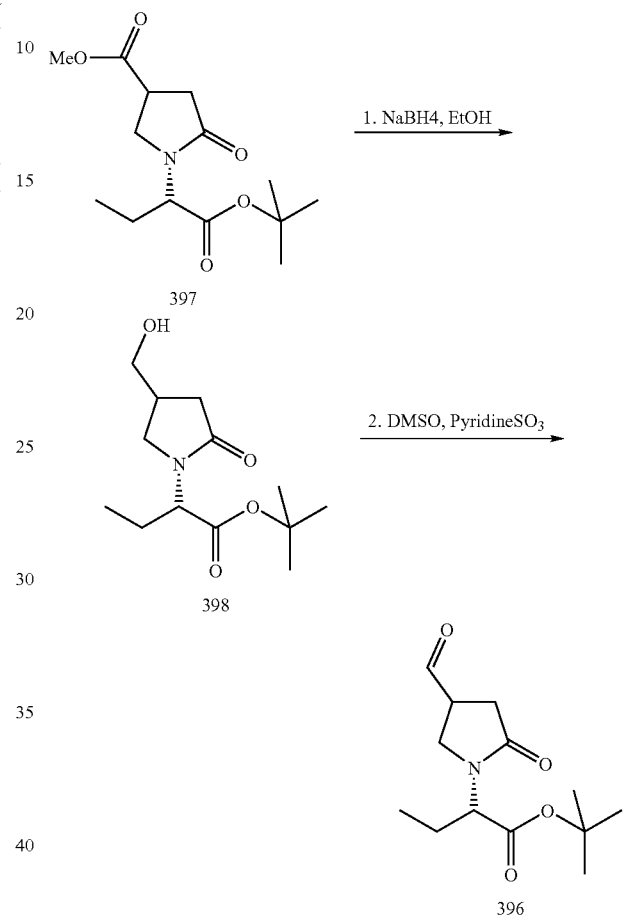

Reduction of the Ester 397 to the Alcohol 398

It is done using the method described in §7.0.2.a using 397 either as a single enantiomer, a mixture of two diastereoisomers or a 1/1/1/1 mixture of 4 stereoisomers. For a 1/1 diastereoisomeric mixture of tert-butyl (2S)-2-[4-(hydroxymethyl)-2-oxo-1-pyrrolidinyl]butanoate 398: GC/MS: 257 M+.

Oxidation to the Aldehyde 396

In a three necked flask, under argon, a solution of tent-butyl (2S)-2-[4-(hydroxymethyl)-2-oxo-1-pyrrolidinyl]butanoate 398 (4.0 g, 0.016 mol.) in CH₂Cl₂ (8 ml) is added to a suspension of CrO₃ (6.2 g, 0.062 mol.) in pyridine (11.3 ml)/CH₂Cl₂ (80 ml) stirred at room temperature. The temperature increases to 30° C. and the suspension is stirred for 0.2 h. The suspension is filtered through celite and the filtrate is washed successively with HCl 1N, brine, dried over magnesium sulfate and concentrated in vacuo to afford the crude aldehyde which is purified by column chromatography on silicagel (hexane/acetone 70/30 (v/v)) to afford 2.03 g of 1-[(1S)-1-(tertbutoxycarbonyl)propyl]-5-oxo-3-pyrrolidinecarboxaldehyde 396 (41%).

Alternatively, the reaction can also be conducted with racemic ester to afford the racemic aldehyde with a similar yield.

Analysis of a 1/1 mixture of 1-[(1S)-1-(tertbutoxycarbonyl) propyl]-5-oxo-3-pyrrolidinecarboxaldehyde 396: $^1$H NMR (250 MHz, (CDCl$_3$): 0.91 (t, 3H), 1.44 (s, 9H), 1.55-1.77 (m, 1H), 1.90-2.15 (m, 1H), 2.63-2.82 (m, 2H), 3.47-3.61 (m, 1H), 3.65-3.79 (m, 1H), 3.83-3.94 (m, 1H of one of the diastereoisomers), 4.48-4.62 (m, 1H), 9.74 (s (broad), 1H).

6.2. Olefination of 1-[(1S)-1-(tertbutoxycarbonyl) propyl]-5-oxo-3-pyrrolidinecarboxaldehyde 396

6.2.1. Synthesis of Ethylenic Derivatives.

Alternatively to §6.2.3., ethylenic derivatives can be obtained by Wittig olefination of the 1-[(1S)-1-(tertbutoxycarbonyl)propyl]-5-oxo-3-pyrrolidinecarboxaldehyde 396 and a phosphonium salt in the presence of a strong base. For example, (2S)-2-(2-oxo-4-vinyl-1-pyrrolidinyl)butanoic acid 2,2-(dimethyl)ethyl ester is obtained by reaction of the aldehyde 396 with Ph$_3$PCH$_3$Br and n-BuLi in THF.

6.2.2. By olefination with Ph$_3$P/CBr$_4$

Alternatively to §6.2.3., halovinyl derivatives can be obtained by Wittig olefination of the 1-[(1S)-1-(tertbutoxycarbonyl)propyl]-5-oxo-3-pyrrolidinecarboxaldehyde 396 in the presence of a phosphine and an halogenomethane. For example, (2S)-2-(2-oxo-4-(2,2-dibromovinyl)-1-pyrrolidinyl)butanoic acid 2,2-(dimethyl)ethyl ester is obtained from aldehyde 396 and CBr$_4$ in the presence of triphenylphosphine.

6.2.3. By Olefination with (Me$_2$N)$_3$P/CF$_2$Br$_2$

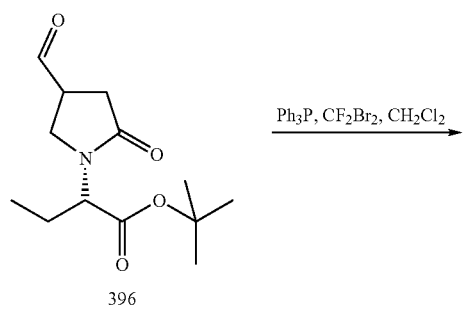

The synthesis of the two diastereoisomers of (2S)-2-(2-oxo-4-(2,2-difluorovinyl)-1-pyrrolidinyl)butanoic acid 2,2-(dimethyl)ethyl ester 399 is representative. In a three necked flask under argon, (Me$_2$N)$_3$P (89.8 g, 0.55 mol.) is added to a solution of CF$_2$Br$_2$ (58 g, 0.25 mol.) in THF (280 ml) at −78° C. (appearance of a white precipitate) and warmed to room temperature. A solution of the aldehyde 396 as a 1/1 mixture of diastereoisomers (35.2 g, 0.138 mol.) in THF is added dropwise to the preformed phosphonium salt. After 1 h, the reaction mixture is filtered through celite and concentrated in vacuo. The reaction mixture is diluted with hexane, washed with brine, dried over magnesium sulfate and concentrated in vacuo to afford the crude olefin which is purified by column chromatography on silicagel (CH$_2$Cl$_2$/MeOH 99/01 (v/v)) to afford 34.6 g of a 1/1 diastereoisomeric mixture of (2S)-2-(2-oxo-4-(2,2-difluorovinyl)-1-pyrrolidinyl)butanoic acid 2.2-(dimethyl)ethyl ester 399 (87%): $^1$H NMR (250 MHz, (CD$_3$)$_2$SO): 0.81-0.91 (m, 3H), 1.44 (s, 9H), 1.50-1.75 (m, 1H), 1.80-1.95 (m, 1H), 2.30-2.40 (m, 2H partially overlapped with solvent), 3.00-3.35 (m, 2H), 3.45-3.55 (m, 1H), 4.20-4.40 (m, 1H), 4.60 (ddd, 1H for one diastereoisomer), 4.75 (ddd, 1H for another diastereoisomer).

6.2.4. By Olefination with (nBu)$_3$P/CCl$_3$F

Alternatively to §6.2.3., halovinyl derivatives can be obtained by Wittig olefination of the 1-[(1S)-1-(tertbutoxycarbonyl)propyl]-5-oxo-3-pyrrolidinecarboxaldehyde 396 in the presence of a phosphine and an halogenomethane. For example of 2-(2-oxo-4-(2-(Z)-fluorovinyl)-1-pyrrolidinyl) butanoic acid 2,2-(dimethyl)ethyl ester is obtained from aldehyde 396 by successive reaction with CFCl$_3$ and n-Bu$_3$P followed by dephosphorylation of the intermediate vinylic phosphonium by NaOH.

6.2.5. Synthesis of the 4-cyano-pyrrolidone

Alternatively, 4-cyano-pyrrolidone derivatives are obtained by reacting 1-[(1S)-1-(tertbutoxycarbonyl)propyl]-5-oxo-3-pyrrolidinecarboxaldehyde 396 with hydroxylamine followed by SeO$_2$.

6.3. Amination of the 2.2-dimethyl-ethyl ester

6.3.1. Deprotection with Trifluoroacetic Acid and Aminolysis

The synthesis of the two diastereoisomers of (2S)-2-(2-oxo-4-(2,2-difluorovinyl)-1-pyrrolidinyl)butanamide 213 and 222 is representative:

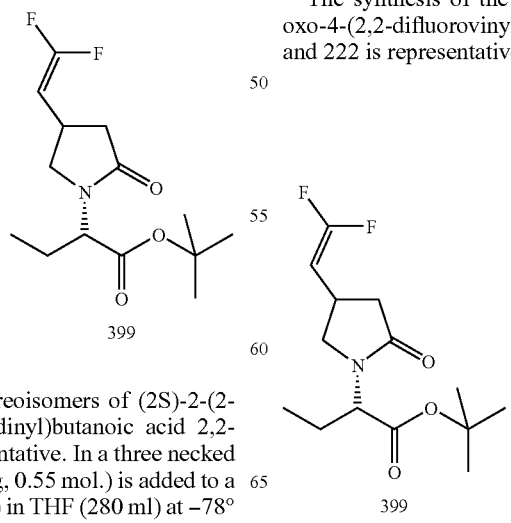

59
-continued

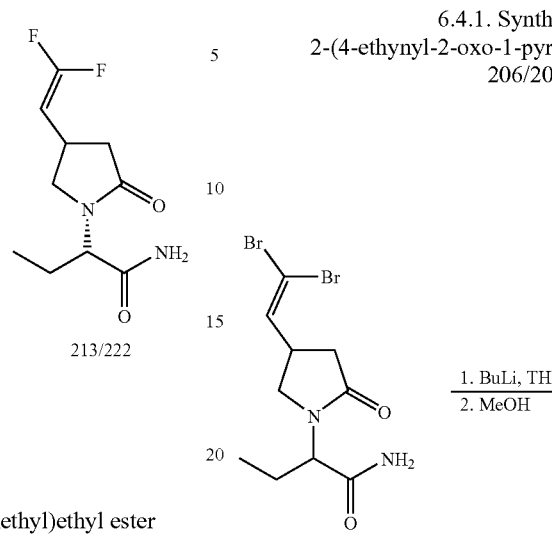

213/222

Step 1: Deprotection of the 2.2-(dimethyl)ethyl ester

In a three necked flask, under argon, a solution of a 1/1 diastereoisomeric mixture of (2S)-2-(2-oxo-4-(2,2-difluorovinyl)-1-pyrrolidinyl)butanoic acid 2.2-(dimethyl)ethyl ester 399 (31.8 g, 0.110 mol.) in trifluoroacetic acid (170 ml) and $CH_2Cl_2$ (500 ml) is stirred for 20 h at room temperature. The reaction mixture is evaporated to dryness. The residue is dissolved in toluene, reevaporated to dryness to eliminate the presence of trifluoroacetic acid to afford 32 g of the crude acids which are used in the next step without any further purification. LC/MS: 234 (MH+)

Step 2: Activation and Ammonolysis

In a three necked flask under argon with mechanical stirring, ClCOOEt (23 ml, 0.24 mol.) is added to a solution of the mixture of acids (25.6 g, 0.11 mol.) in $CH_2Cl_2$ (250 ml) and triethylamine (33.7 ml) cooled at −15° C. The reaction mixture is stirred for 1.5 h at −10° C. then gaseous $NH_3$ is bubbled through the solution while maintaining the temperature below 0° C. The suspension is stirred for 1 h at 0° C., warmed to room temperature, filtered and the filtrate is evaporated under vacuo. The crude amides are purified by column chromatography on silicagel ($CH_2Cl_2$/EtOH 99/01 (v/v)) to afford 23 g of a 1/1 diastereoisomeric mixture of (2S)-2-(2-oxo-4-(2,2-difluorovinyl)-1-pyrrolidinyl)butanoic acid 2.2-(dimethyl)ethyl ester which is purified by column chromatography on chiral phase (hexane/EtOH) to afford the two diastereoisomers 213 (10.1 g, recrystallised from i-$Pr_2O$) and 222 (11.2 g, recrystallised in i-$Pr_2O$).

6.3.2. Alternatively, the Deprotection can be Performed with Bromocatechol Borane.

4 diastereoisomers of 2-(2-oxo-4-(2,2-dimethylvinyl)-1-pyrrolidinyl)butanamide 163 are obtained by reacting the 1/1/1/1 diastereoisomeric mixture of 2-(2-oxo-4-(2,2-dimethylvinyl)-1-pyrrolidinyl)butanoic acid 2,2-(dimethyl)ethyl ester with bromocatechol borane to afford the acid followed by amination in the conditions described in §6.3.1 (step 2).

60

6.4. Synthesis of Acetylenic Derivatives

6.4.1. Synthesis of 2-(4-ethynyl-2-oxo-1-pyrrlidinyl)butanamide 206/207

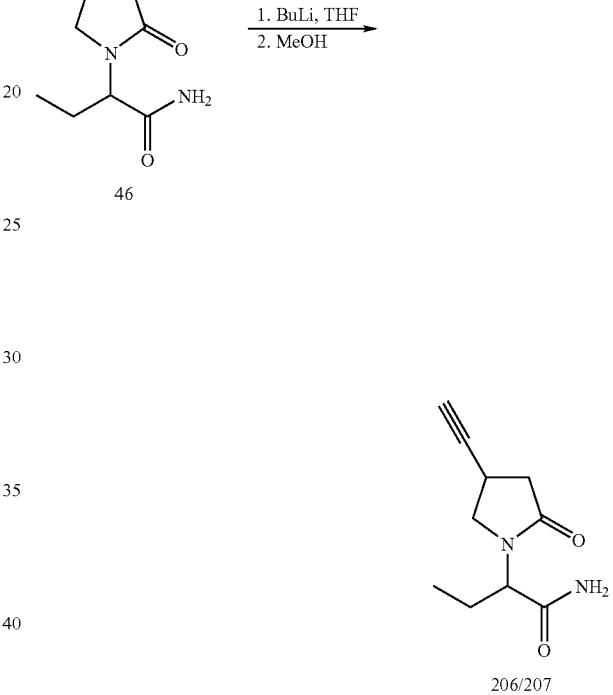

In a three necked flask, under argon, n-butyllithium (1.6 M in hexanes, 116 ml) is added to a solution of a 1/1 mixture of two diastereoisomers of 2-[4-(2,2-dibromovinyl)-2-oxo-1-pyrrolidinyl]butanamide (undetermined stereochemistry, 10.95 g, 0.031 mol.) in THF cooled at −78° C. The white suspension is stirred for 1.5 h at this temperature, quenched with MeOH (120 ml), warmed to room temperature and concentrated in vacuo. The crude alkyne is dissolved in EtOH/$CH_2Cl_2$ (10/90 v/v)), filtered through celite, concentrated in vacuo and the resulting solid is purified successively by chromatography on silicagel (EtOH/$CH_2Cl_2$: 10/90 (v/v)) and by chromatography on chiral phase (EtOH/hexane) to afford the two diastereoisomers of 2-(4-ethynyl-2-oxo-1-pyrrolidinyl)butanamide 206 (0.84 g, recrystallised in PhMe) and 207 (0.44 g, recrystallised in PhMe).

Alternatively, 2-(4-bromo-ethynyl-2-oxo-1-pyrrolidinyl)butanamide 267 is obtained by reacting 2-[4-(2,2-dibromovinyl)-2-oxo-1-pyrrolidinyl]butanamide 47 with two equivalent of potassium tertbutoxide in THF at low temperature (−50° C. to 0° C.).

6.4.2. Synthesis of 2-(4-propyn-1-yl-2-oxo-1-pyrrolidinyl)butanamide 280

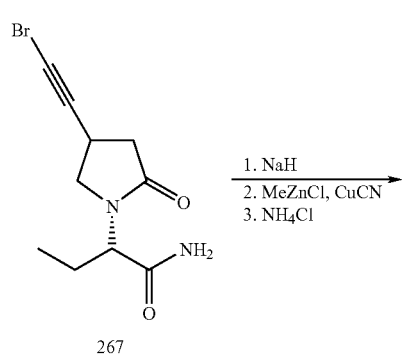

267

1. NaH
2. MeZnCl, CuCN
3. NH$_4$Cl

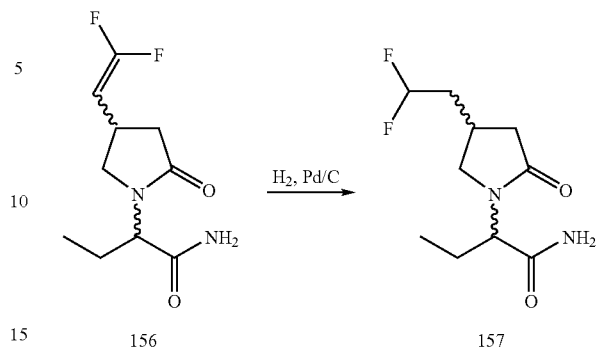

156    157

In a 0.25 L pressure jar, under inert atmosphere, 1 g (0.0043 mmol.) of 156 and Pd on charcoal (10% w/w, 0.2 g) are dissolved in EtOH (50 ml) and the mixture hydrogenated on a Parr hydrogenator. After 20 h, the mixture is degassed, filtered on a Celite/Norite pad, and the filtrate concentrated in vacuo, to give the crude fluoro alkane which is recrystallised from PhMe to afford a 1/1/1/1 mixture of the 4 diastereoisomers of 2-[4-(2,2-difluoroethyl)-2-oxo-1-pyrrolidinyl]butanamide 157 as a white solid (0.75 g).

6.6. Synthesis of 2-[4-(5-methyl-1,3-oxazol-2-yl)-2-oxo-1-pyrrolidinyl]butanamide 62 and 63

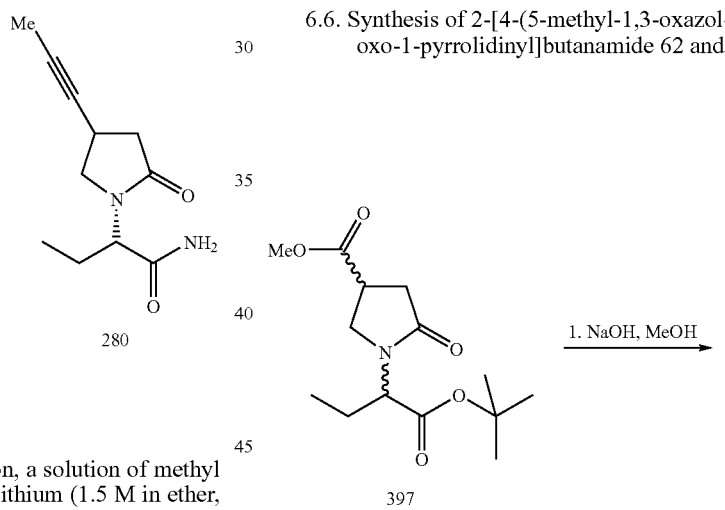

280

397

1. NaOH, MeOH

In a three necked flask, under argon, a solution of methyl zinc chloride (prepared from methyllithium (1.5 M in ether, 6.14 ml) and ZnCl$_2$ (1.25 g) in THF (15 ml)) is added to a solution of CuCN (0.82 g) and LiCl (0.78 g) in THF (10 ml) at −10° C. In another three necked flask, under argon, NaH (80% in oil, 0.097 g) is added to a solution 2-(4-bromoethynyl-2-oxo-1-pyrrolidinyl)butanamide (1 g, 0.0036 mol.) in THF (20 ml) at −10° C. followed by ZnCl$_2$ (0.50 g). This amide solution is then added dropwise onto the organocuprate cooled at −78° C. The reaction mixture is stirred for 3 h at this temperature and allowed to warm to room temperature overnight. After hydrolysis with saturated aqueous NH$_4$Cl, the aqueous layer is extracted with CH$_2$Cl$_2$, dried over MgSO$_4$, filtered and concentrated in vacuo to afford the crude alkyne which is purified by chromatography on chiral phase (EtOH/hexane) to afford the 2-(4-propyn-1-yl-2-oxo-1-pyrrolidinyl)butanamide 280.

6.5. Hydrogenation of Olefinic Pyrrolidones

The synthesis of the 1/1/1/1 mixture of the 4 diastereoisomers of 2-[4-(2,2-difluoroethyl)-2-oxo-1-pyrrolidinyl]butanamide 157 is representative:

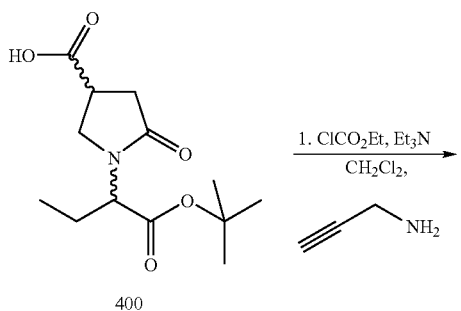

400

1. ClCO$_2$Et, Et$_3$N
CH$_2$Cl$_2$,

-continued

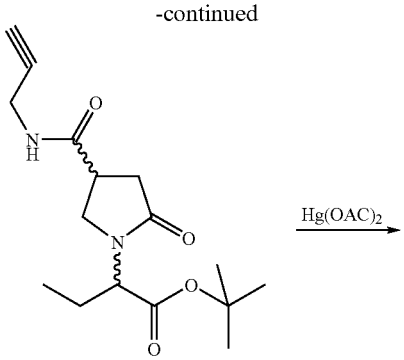

401

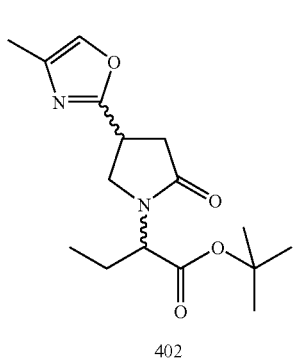

402

Step 1: Hydrolysis of the Ester

In a three necked flask, under argon, NaOH 1N (39 ml) is added to a solution of methyl 1-[1-(tert-butoxycarbonyl)propyl]-5-oxo-3-pyrrolidinecarboxylate 397 as a 1/1/1/1 mixture of 4 stereoisomers (10 g, 0.035 mol.) in MeOH (100 ml) at 20° C. The solution is stirred for 0.5 h, evaporated to dryness and acidified to pH=1 with HCl 1N. The aqueous layer is extracted with AcOEt, dried over MgSO$_4$, filtered and concentrated in vacuo to afford the crude acid 400 (8.45 g) as a white solid which is used without any further purification in the next step. $^1$H NMR (250 MHz, (CD$_3$)$_2$SO): 0.80 (t, 3H), 1.44 (s, 9H), 1.55-1.60 (m, 1H), 1.70-1.95 (m, 1H), 2.40-2.55 (m, 2H partially overlapped with solvent), 3.10-3.55 (m, 1H partially overlapped with solvent), 4.45 (dd, 1H).

Step 2: Synthesis of the Amide 401

In a three necked flask under argon, ClCOOEt (0.50 ml, 0.005 mol.) is added to a solution of the acid 400 (0.678 g, 0.0025 mol.) in CH$_2$Cl$_2$ (10 ml) and triethylamine (0.77 ml) cooled at −20° C. The reaction mixture is stirred for 1.5 h at −10° C. then propargyl amine (0.36 ml) is added to the solution while maintaining the temperature below 0° C. The suspension is stirred for 1 h at 0° C., warmed to room temperature, filtered and the filtrate is evaporated under vacuo. The crude amide is purified by column chromatography on silicagel (CH$_2$Cl$_2$/MeOH 98/02 (v/v)) to afford 0.8 g of the propargyl amide 401 as a 1/1/1/1 mixture of four diastereoisomers. $^1$H NMR (250 MHz, (CD$_3$)$_2$SO): 0.80 (t, 3H), 1.44 (s, 9H), 1.55-1.65 (m, 1H), 1.70-1.95 (m, 1H), 2.40-2.55 (m, 4H partially overlapped with solvent), 3.0-3.70 (m, 3H partially overlapped with solvent), 3.70-3.90 (m, 2H), 4.45 (m, 1H), 8.45 (m, 1H).

Step 3: Synthesis of the Oxazole 402

In a three necked flask under argon, a solution of the amide 402 (0.77 g, 0.0025 mol.) in AcOH (40 ml) and Hg(OAc)$_2$ (0.048 g, 0.00015 mol.) are refluxed for 1 h, the reaction is cooled to room temperature, concentrated under vacuo and hydrolyzed with saturated Na$_2$CO$_3$. The aqueous layer is extracted with CH$_2$Cl$_2$ and the organic phase is washed with brine, dried over MgSO$_4$, filtered and concentrated in vacuo to afford the crude compound which is purified by chromatography on silicagel (Hexane/AcOEt: 50/50 (v/v)) to afford the pure oxazole 402 (0.15 g, 20%). GC/MS: 308 (M+) which may be converted into 62 and 63 by ammonolysis analogously to 6.3.1.

6.7. Synthesis of Tetrazoles

6.7.1. Synthesis of the Unsubstituted Tetrazoles

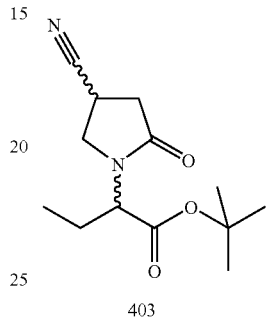

403

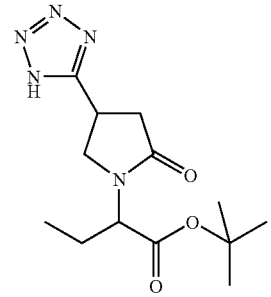

404

In a three necked flask, under argon, a solution of the racemic nitrile 403 (2.66 g, 0.011 mol.), NaN$_3$ (4.8 g, 0.073 mol.) and Et$_3$N-hydrochloride (10.12 g) is heated at 110° C. in DMF (60 ml) for 2 h, cooled down to room temperature and evaporated under vacuo. The crude is purified by chromatography on silicagel (CH$_2$Cl$_2$/MeOH/AcOH: 90/08/02 (v/v)) to afford the racemic tetrazol ester 404 (3.42 g, 0.010 mol.) as a 1/1/1/1 mixture of diastereoisomers. LC/MS: 295 (MH+).

6.7.2. Alkylation of Tetrazoles

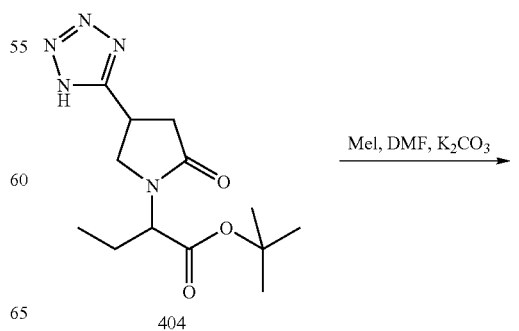

404

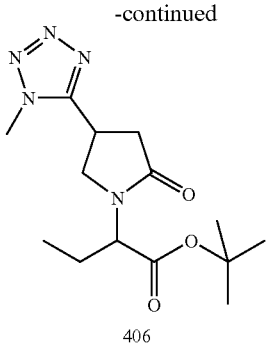

406

+

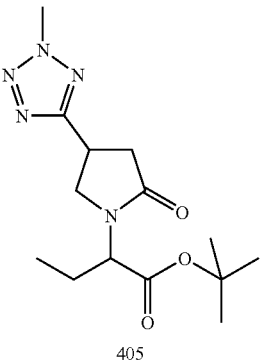

405

In a three necked flask, under argon, a suspension of the racemic tetrazole 404 (5.6 g, 0.019 mol.), K₂CO₃ (2.88 g) and MeI (1.3 ml) in DMF (60 ml) is stirred at room temperature for 29 h and evaporated under vacuo. The crude mixture is purified by chromatography on silicagel (MTBE/Hexane: 50/50 (v/v)) to afford the two regioisomeric tetrazole 405 (1.98 g, 34%) and 406 (1.03 g, 17%) as oils. LC/MS: 309 (MH+).

6.8. Synthesis of Thiazoles

6.8.1. Synthesis of Thioamides.

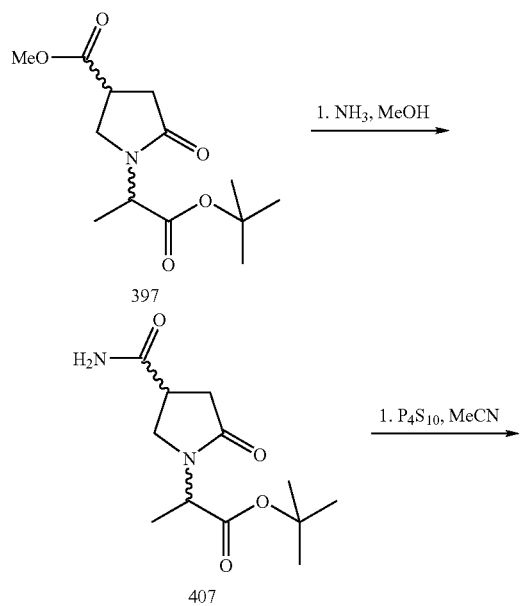

6.8.1.1. Ammonolysis of 397

In a 0.5 l three necked flask fitted with reflux condenser, magnetic stirrer and an addition gas tube dipping in the solution, 10 g (0.035 mmoles) of 397 are dissolved in 100 ml methanol. Gaseous ammonia is then bubbled through the solution, and the saturated solution kept at room temperature for 1 day, while occasionally resaturating with ammonia. After completion of the reaction, the solution is concentrated in vacuo to afford the crude amide 407 (9.6 g, 100%). $^{1}$H NMR (250 MHz, (CD₃)₂SO): 0.85 (t, 3H), 1.44 (s, 9H), 1.55-1.60 (m, 1H), 1.70-1.95 (m, 1H), 2.40-2.60 (m, 2H partially overlapped with solvent), 3.00-3.70 (m, 1H partially overlapped with solvent), 4.35-4.45 (m, 1H), 6.95 (s (broad), 1H), 7.40 (s(broad), 1H).

6.8.1.2. Synthesis of Thioamide 408

In a three necked flask, under argon, a solution of the crude amide 407 (6 g, 0.022 mol.), P₄S₁₀ (4.93 g, 0.011 mol.) and NaHCO₃ (3.73 g) in MeCN (100 ml) is stirred at 5° C. for 6 h. The reaction mixture is filtered, concentrated in vacuo and the crude thioamide is purified by chromatography on silicagel (AcOEt/hexane: 50/50 (v/v)) to give after recrystallisation from AcOEt the thioamide 408 (3.7 g, 60%). GC/MS: 286 (M+).

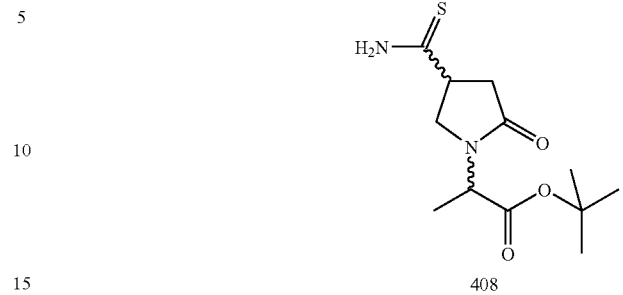

408

6.8.2. Synthesis of Substituted Thiazoles

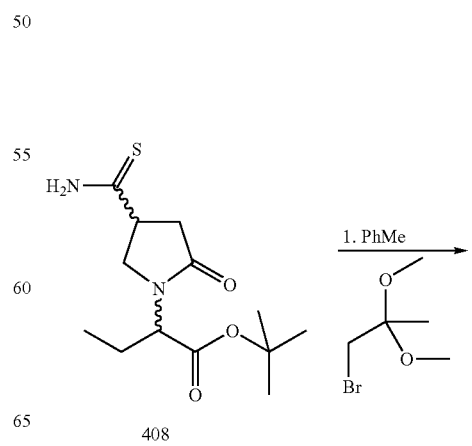

408

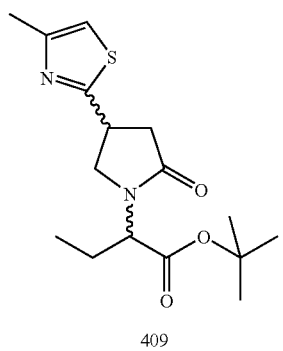

409

In a three necked flask, under argon, a solution of the thioamide 408 as a 1/1/1/1 mixture of 4 diastereoisomers (this patent, 1.5 g, 0.005 mol.), Al$_2$O$_3$ (12 g) and 1-bromo-2-dimethoxy prop-2-ene (0.85 ml) in PhMe (100 ml) is refluxed for 3 h. The reaction mixture is cooled down to room temperature, filtered and concentrated in vacuo to afford the crude thiazole 409 (0.5 g, 30%) which is used in the next steps without any further purification. GC/MS: 324 (M+).

6.8.3. Synthesis of Unsubstituted Thiazoles

Alternatively unsubstituted thiazoles can be obtained by reacting thioamides 408 with Al$_2$O$_3$ and bromo-acetaldehyde (generated in situ from bromo-2,2-dimethoxy ethane in acidic conditions).

6.8.4. Synthesis of 1,2,4-thiadiazol-5-yl-Derivatives

Alternatively, 1,2,4-thiadiazol-5-yl-derivatives can be obtained by reacting thioamide 408 successively with N,N-dimethyl-acetamide dimethylacetal followed by cyclization in the presence of pyridine.

6.9. Synthesis of 2-[2-oxo-4-(3-pyridinylcarbonyl)-1-pyrrolidinyl]butanoic acid 2,2-dimethyl ethyl ester 410

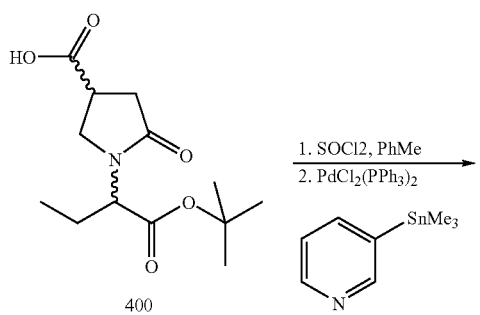

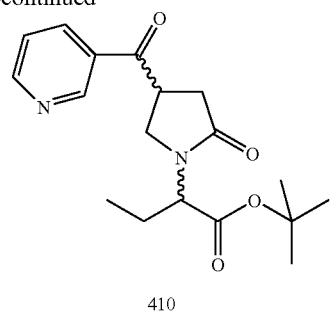

410

In a three necked flask under argon, SOCl$_2$ (0.56 ml) is added to a solution of the acid 400 (1.90 g, 0.007 mol.) in PhMe (20 ml) at room temperature. The reaction mixture is refluxed for 1.5 h and becomes yellow. After cooling down to room temperature, PdCl$_2$(PPh$_3$)$_2$ (0.25 g, 0.00035 mol.) and 3-trimethylstannyl-pyridine (1.7 g, 0.007 mol.) are added in one portion, the reaction mixture is refluxed for 0.5 h, cooled down to room temperature, quenched with water. The aqueous layer is extracted with dichloromethane and the combined organic phases are washed with brine, dried over magnesium sulfate, filtered and concentrated in vacuo (3.2 g). The crude ketone is purified by column chromatography on silicagel (CH$_2$Cl$_2$/MeOH 97/03 (v/v)) to afford 1.3 g of the ketone 410 as a 1/1/1/1 mixture of four diastereoisomers. LC/MS: 333 (MH+).

EXAMPLE 7

Synthesis of 2-(4-substituted-2-oxo-pyrrolidinyl)-butanamides by Substitution of an Activated 2-(4-hydroxymethyl-2-oxo-pyrrolidinyl)-butanamide

7.0. Synthesis of the Starting Alcohols

7.0.1. Synthesis of the Ester-Amide 7.0.1.a. Synthesis of methyl 1-[(1S)-1-(aminocarbonyl)propyl]-5-oxo-3-pyrrolidinecarboxylate 11/12

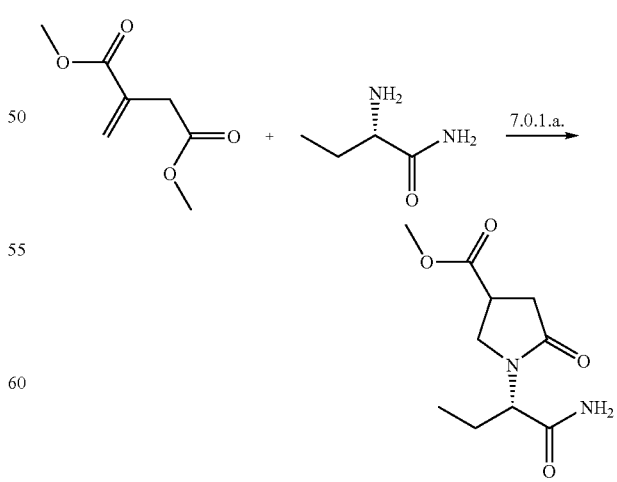

12/11

In a 10 l three necked flask fitted with mechanical stirrer and reflux condenser, under inert atmosphere, 1226 g (12 moles, 1 eq) of (2S)-2-aminobutanamide and 1912 ml (2150 g, 13.2 moles, 1.1 eq) of dimethyl itaconate are dissolved in 6.13 l of MeOH. The mixture is brought to reflux for 10 hours, and cooled down slowly to 20° C. over 4 hours. It is filtered, the precipitate washed with MeOH, and the combined organic phases concentrated to dryness to give 3.283 g of crude intermediate, 74%.

In a 20 l three necked flask fitted with mechanical stirrer and Rashig column and distillation arm, under inert atmosphere, the crude intermediate and 84.7 g (891 mmoles, 0.1 equiv.) of 2-hydroxypyridine are dissolved in 11.6 l of toluene. The mixture is brought to reflux and the methanol formed distilled off for 8 hours, until 480 ml had been collected. Temperature in the pot reached 112° C. The mixture is cooled down and concentrated to dryness to give 2,187 g of crude amide ester as a mixture of diastereomers in a ratio 57.5/42.5.

The 2 diastereomers are separated by Preparative Liquid Chromatography on Chiral Phase (Chiralpak AD 100*500 mm, EtOH/H$_2$O 99.9:0.1), the eluates concentrated to dryness to give 968 g of crude 12 (first eluted) and 1,052 g of crude 11 (second eluted). Crude 12 did not crystallise, it is dissolved in 1.5 l of EtOH and kept as such, for further use. Crude 11 is recrystallised from 2 l of EtOAc to give 676 gr of pure 11.

Alternatively, methyl 1-[(1S)-2-amino-1-methyl-2-oxoethyl]-5-oxo-3-pyrrolidinecarboxylate, methyl 1-[(1S)-1-(aminocarbonyl)butyl]-5-oxo-3-pyrrolidinecarboxylate, methyl 1-{(1S)-1-[(methylamino)carbonyl]propyl}-5-oxo-3-pyrrolidinecarboxylate, are prepared in similar ways.

7.0.2. Synthesis of the Alcohol-Amide

7.0.2.a. Synthesis of (2S)-2-[4-(hydroxymethyl)-2-oxo-1-pyrrolidinyl]butanamide 6.

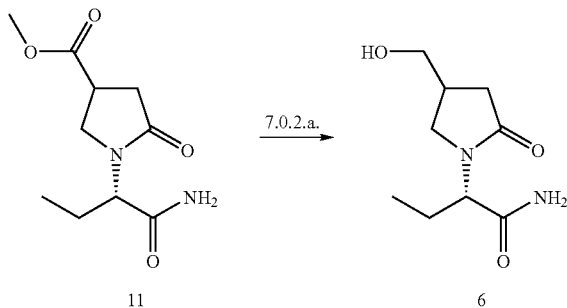

In a 2 l three necked flask fitted with mechanical stirrer and reflux condenser, under inert atmosphere, a solution of 133 g (583 mmoles, 1 eq) of (2S)-2-(4-methoxycarbonyl-2-oxo-1-pyrrolidinyl)butanamide 11 in 200 ml of EtOH is added to 300 ml of EtOH, and the mixture cooled down to 0° C. 66.2 g (1.74 mole, 12 eq) of solid NaBH$_4$ are then added by portions over 1.5 hour, all the while maintaining the temperature between 2 and 4° C. After 2 hours, the temperature is raised to 12° C. for 1 hour, and lowered again to 2-4° C. 240 ml of a saturated solution of NH$_4$Cl are added dropwise over 1 hour, followed by 120 ml of acetone, and the mixture is left overnight at room temperature. The mixture is filtered, the precipitate washed with 3×70 ml of EtOH and the combined organic fractions concentrated to dryness to give 148 g of crude 6. It is suspended in 300 ml of CH$_2$Cl$_2$ and stirred for 30 min, filtered, washed with 2×100 ml of CH$_2$Cl$_2$ and dried to give 114 g of pure 6, 98%.

Alternatively, (2S)-2-[4-(hydroxymethyl)-2-oxo-1-pyrrolidinyl]propanamide, (2S)-2-[4-(hydroxymethyl)-2-oxo-1-pyrrolidinyl]pentanamide, (2S)-2-[4-(hydroxymethyl)-2-oxo-1-pyrrolidinyl]-N-methylbutanamide are prepared in similar ways.

7.1. Synthesis by Direct Transformation of the Alcohol Using PPh$_3$

7.1.1. Synthesis of (2S)-2-[4-(iodomethyl)-2-oxo-1-pyrrolidinyl]butanamide 10

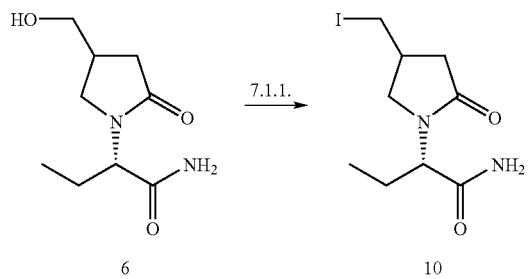

In a 10 l 3 necked vessel, fitted with mechanical stirrer and reflux condenser under inert atmosphere, 400 g (2 mole, 1 eq) of (2S)-2-[4-(hydroxymethyl)-2-oxo-1-pyrrolidinyl]butanamide 6 are dissolved in 3 l of acetonitrile. 629 g (2.4 moles, 1.2 eq) of triphenylphosphine are added, followed by 608 g (2.4 moles, 1.2 eq) of iodine in three portions over 5 min. The mixture is heated up to 60° C. in 30 min, and stirred at that temperature for 5 hours. After cooling down, the mixture is concentrated to dryness, the residue suspended in a solution of 750 g of Na$_2$S$_2$O$_3$ in 10 l of water and stirred at 50° C. for 4 hours. The precipitate is filtered off and washed with 3×1 l of water. The combined aqueous phases are treated with 1 kg of NaCl, and extracted with 6×1 l of CH$_2$Cl$_2$. The combined organic phases are dried over MgSO$_4$, filtered and concentrated to dryness to give 482 g of crude 10. It is crystallised from toluene. Several crops are recrystallised together from ethyl acetate to give 425 g of pure 10, 68%.

Alternatively, (2S)-2-[4-(iodomethyl)-2-oxo-1-pyrrolidinyl]-N-methylbutanamide 146, (2S)-2-[4-(iodomethyl)-2-oxo-1-pyrrolidinyl]propanamide 110, (2S)-2-[4-(iodomethyl)-2-oxo-pyrrolidin-1-yl]pentanamide 105, (2S)-2-[4-(bromomethyl)-2-oxo-1-pyrrolidinyl]butanamide 8, (2S)-2-[4-(chloromethyl)-2-oxo-1-pyrrolidinyl]butanamide 30 are prepared in similar ways

7.1.2. Synthesis of (2S)-2-[2-oxo-4-(phenoxymethyl)-1-pyrrolidinyl]butanamide 18

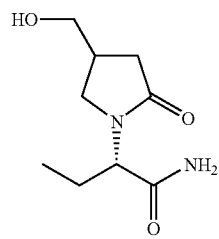

6

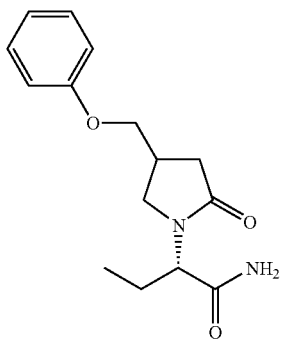

18

In a 50 ml three necked flask fitted with magnetic stirrer and dropping funnel under inert atmosphere, 1 g (5 mmoles, 1 eq) of (2S)-2-[4-(hydroxymethyl)-2-oxo-1-pyrrolidinyl]butanamide 6 is dissolved in 20 ml of THF and cooled down to 0° C. 517 mg of phenol, 0.87 ml (960 mg) of diethyl azodicarboxylate and 1.44 g of triphenylphosphine (5.5 mmoles, 1.1 eq each) are successively added and the mixture stirred for 2 hours. The mixture is concentrated to dryness and purified by Prep LC (500 kg $SiO_2$, $CH_2Cl_2$/EtOH, 97.5:2.5) to give 1.1 g of pure 18, 80%, crystallised from ethyl acetate.

7.2. Synthesis by Substitution of a Mesylate

7.2.1. Synthesis of {1-[(1S)-1-(aminocarbonyl)propyl]-5-oxo-3-pyrrolidinyl}methyl methanesulfonate 37

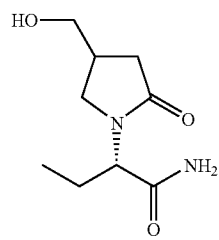

6

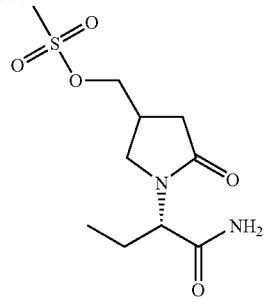

37

In a 4 l three necked flask fitted with mechanical stirrer, dropping funnel and reflux condenser under inert atmosphere, 114 g (569 mmoles, 1 eq) of (2S)-2-[4-(hydroxymethyl)-2-oxo-1-pyrrolidinyl]butanamide 6 are dissolved in 2 l of $CH_2Cl_2$ and cooled down to 0° C. 158.5 ml (115 g, 2 eq) of dry triethylamine are added in one portion, followed by dropwise addition of a solution of 66.3 ml (96.2 g, 1.5 eq) of methanesulfonyl chloride in 190 ml of $CH_2Cl_2$ over 1 hour, all the while maintaining the temperature below 4° C. After 4 hours, 7.5 ml of methanesulfonyl chloride and 15 ml of triethylamine are added and the mixture is kept overnight in the refrigerator. The mixture is filtered, the residue washed with $CH_2Cl_2$ and the combined organic phases concentrated to dryness to give 216 g of crude 37. It is purified by Prep LC in several batches (1 kg $SiO_2$, $CH_2Cl_2$/EtOH, 100:0->96:4) to give 109 g of pure 37, 69%.

Alternatively, {1-[(1S)-1-(aminocarbonyl)propyl]-5-oxo-3-pyrrolidinyl}methyl 4-methylbenzenesulfonate 31 is prepared in an analogous way.

7.2.2. Synthesis of (2S)-2-[4-(azidomethyl)-2-oxo-1-pyrrolidinyl]butanamide 32

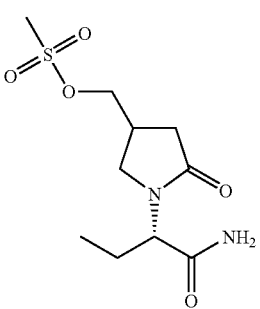

37

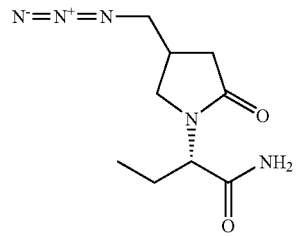

32

In a 3 l three necked flask fitted with mechanical stirrer and reflux condenser, under inert atmosphere, 89.7 g (322 mmoles, 1 eq) of {1-[(1S)-1-(aminocarbonyl)propyl]-5-oxo-3-pyrrolidinyl}methyl methanesulfonate 37 are dissolved in 300 ml of acetonitrile. 27.3 g (419 mmoles, 1.3 eq) of sodium azide are added in one portion, with 150 ml of acetonitrile. The mixture is brought to reflux in 20 min, and stirred overnight. 3.1 g (48 mmoles, 0.2 eq) of sodium azide are added and reflux continued for a total of 44 hours. After cooling down to 10° C., the mixture is filtered, the precipitate washed with 3×50 ml of acetonitrile and the combined organic fractions concentrated to dryness to give 77.3 g of crude 32. It is crystallised from 150 ml of ethyl acetate at 10° C. to give 60 g of pure 32, 82%.

Alternatively, (2S)-2-[4-(fluoromethyl)-2-oxo-1-pyrrolidinyl]butanamide 44, (2S)-2-[2-oxo-4-(1H-tetrazol-1-ylmethyl)-1-pyrrolidinyl]butanamide 39, (2S)-2-[2-oxo-4-(1H-tetrazol-1-ylmethyl)-1-pyrrolidinyl]butanamide 40, (2S)-2-[2-oxo-4-(1H-1,2,4-triazol-1-ylmethyl)-1-pyrrolidinyl]butanamide 55, 2-[2-oxo-4-(1H-1,2,3-triazol-1-ylmethyl)-1-pyrrolidinyl]butanamide 56, (2S)-2-{4-[(isopropylsulfanyl)methyl]-2-oxo-1-pyrrolidinyl}butanamide 24, (2S)-2-[2-oxo-4-(1-pyrrolidinylmethyl)-1-pyrrolidinyl]butanamide 15, (2S)-2-[2-oxo-4-(4-thiomorpholinylmethyl)-1-pyrrolidinyl]butanamide 17, are prepared in similar ways, from activated alcohol derivatives, such as mesylates, tosylates or halides.

7.3. Other Synthesis

7.3.1. Synthesis of {1-[(1S)-1-(aminocarbonyl)propyl]-5-oxo-3-pyrrolidinyl}methyl nitrate 38

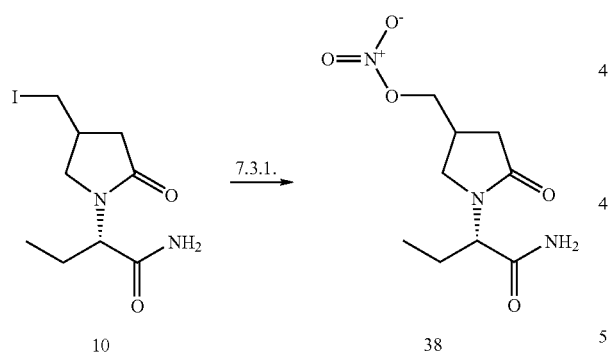

In a 500 ml 3 necked flask, fitted with mechanical stirrer and reflux condenser under inert atmosphere, 8.10 g (26 mmoles, 1 eq) of (2S)-2-[4-(iodomethyl)-2-oxo-1-pyrrolidinyl]butanamide 10 are dissolved in 250 ml of acetonitrile. 4.86 g (28.6 mmoles, 1.1 eq) of silver nitrate are added and the mixture is brought to reflux. After two hours, 440 mg (2.8 mmoles, 0.1 eq) of silver nitrate are added, and reflux continued for a total of 4 hours. After cooling down the mixture is concentrated to dryness and purified by PrepLC (200 g SiO$_2$, CH$_2$Cl$_2$/MeOH/NH$_4$OH, 96:5.4:0.6) to give 5.7 g of crude 38. It is crystallised from 50 ml of ethyl acetate to give 4.13 g of pure 38, 65%.

7.3.2. Synthesis 2-{4-[(benzyloxy)methyl]-2-oxo-1-pyrrolidinyl}butanamide 153/154

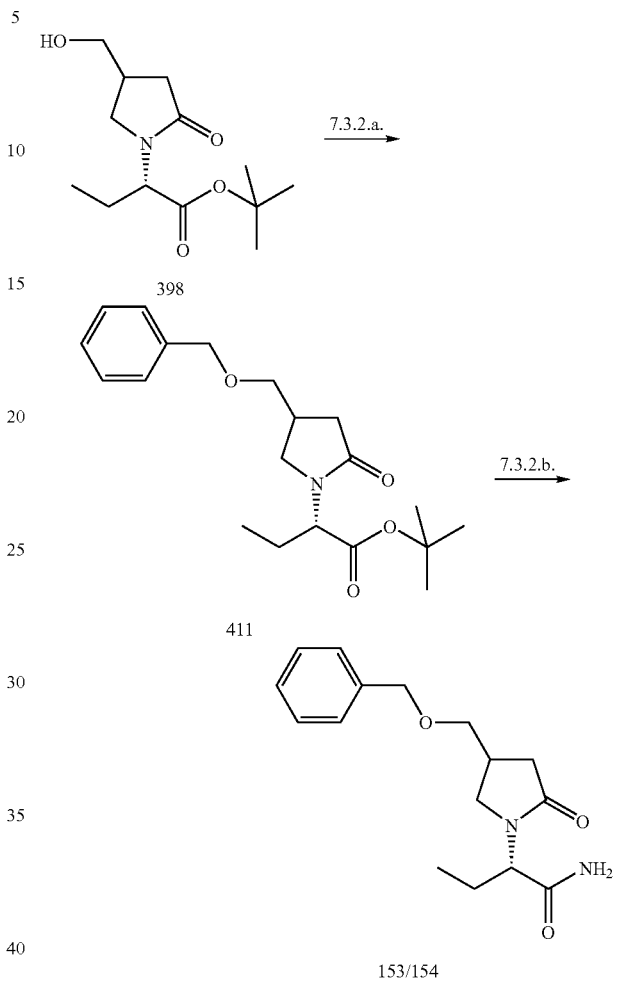

7.3.2.a. Synthesis of tert-butyl (2S)-2-{4-[(benzyloxy)methyl]-2-oxo-1-pyrrolidinyl}butanoate In a 100 ml 3 necked flask, fitted with magnetic stirrer and reflux condenser under inert atmosphere, 1.1 g (60%, 27.5 mmoles, 1.1 eq) of sodium hydride are suspended in 60 ml of DMF and the mixture cooled down to 0° C. 6.37 g (24.8 mmoles, 1 eq) of tert-butyl (2S)-2-[4-(hydroxymethyl)-2-oxo-1-pyrrolidinyl]butanoate 398 in 10 ml of DMF are added cautiously. After 10 min, 3.3 ml (4.75 g, 27.8 mmoles, 1 eq) of benzyl bromide in 10 ml of DMF are added, and stirring continued for 30 min at 0° C., followed by 3 hours at room temperature. The mixture is concentrated to dryness, the residue is suspended in brine/CH$_2$Cl$_2$, decanted and extracted with CH$_2$Cl$_2$. The combined organic phases are dried over MgSO$_4$, concentrated to dryness and the residue is purified by Prep LC (1 kg SiO$_2$, hexane/MTBE, 40:60->0:100) to give 3.2 g of a mixture of t-Bu and Benzyl esters in two fractions, 37% total yields. It is used as such for the next step 7.3.1.b. $^1$H NMR (250 MHz, (CDCl$_3$): 0.85 (t, 3H), 1.44 (s, 9H), 1.55-1.95 (m, 2H), 2.10 (dd, 1H), 2.45 (dd, 1H), 2.55-2.70 (m, 1H), 3.45-3.55 (m, 1H), 4.40 (dd, 1H), 4.55 (s, 2H), 7.20-7.40 (m, 5H).

7.3.2.b. Synthesis of 2-{4-[(benzyloxy)methyl]-2-oxo-1-pyrrolidinyl}butanamide 153

In a 50 ml 3 necked flask, fitted with magnetic stirrer and reflux condenser under inert atmosphere, 1.75 g of benzyl ester enriched fraction are dissolved in 20 ml of MeOH. Gaseous ammonia is then bubbled through the solution and the saturated solution kept at room temperature for 24 hours, while occasionally resaturating with ammonia. After completion of the reaction, the solution is concentrated to dryness and purified by Prep LC (1 kg $SiO_2$, $CH_2Cl_2$/MeOH, 98:2-> 90:10) to give the two diastereomers.

In a 25 ml 3 necked flask, fitted with magnetic stirrer and reflux condenser under inert atmosphere, 1.24 g of t-Bu ester enriched fraction are dissolved in 16 ml of a 1:1 mixture of $CH_2Cl_2$/TFA, and kept at 0-5° C. for 24 hours. The solution is concentrated to dryness and the residue dissolved in 10 ml of $CH_2Cl_2$. 1.2 ml (2.2 th. eq) of triethylamine are added, and the mixture cooled down to −20° C. 780 μl of ethyl chloroformate are added dropwise, and the mixture left slowly warm up to −10° C. over 1.5 hour. Gaseous ammonia is then bubbled through the solution for 0.5 hour, and the mixture kept overnight at room temperature. It is filtered, the precipitate washed with $CH_2Cl_2$, the combined organic fractions concentrated to dryness and purified by Prep LC (1 kg $SiO_2$, $CH_2Cl_2$/MeOH, 98:2->90:10) to give the two diastereomers. The first and second eluted diastereomers from the two runs are combined and crystallised from toluene to give respectively 305 mg of pure 153 and 480 mg of pure 154, 11% overall.

7.3.3. Synthesis (2S)-2-{4-[(5-methyl-1H-1,2,3-triazol-1-yl)methyl]-2-oxo-1-pyrrolidinyl}butanamide 52

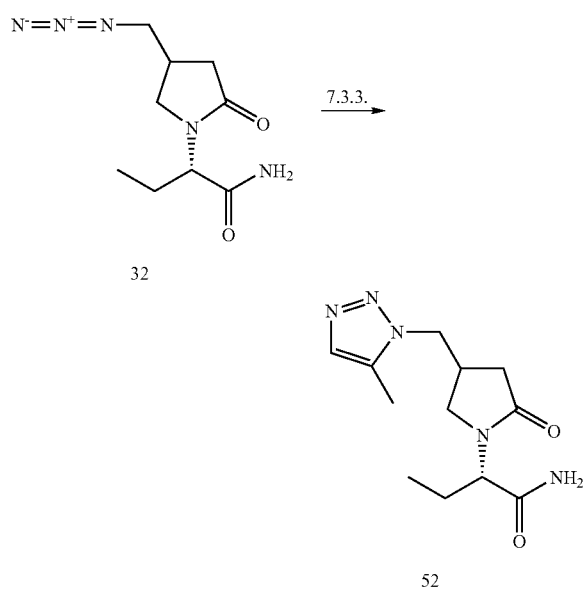

In a 50 ml 3 necked flask, fitted with magnetic stirrer and reflux condenser under inert atmosphere, 1 g (4.44 mmoles, 1 eq) of (2S)-2-[4-(azidomethyl)-2-oxo-1-pyrrolidinyl]butanamide 32 is suspended in 20 ml of toluene. 1.55 g (4.88 mmoles, 1.1 eq) of 1-(triphenylphosphoranylidene)acetone are added, and the mixture is heated up to 80° C. for 24 hours. After cooling down, the mixture is concentrated to dryness and purified by Prep LC (1 kg $SiO_2$, $CH_2Cl_2$/MeOH/$NH_4OH$, 94.5:5:0.5). It is suspended in 15 ml of water and lyophilised to give 240 mg of pure 52 as a clear oil, 42%.

7.3.4. Synthesis of (2S)-2-[4-(isothiocyanatomethyl)-2-oxo-1-pyrrolidinyl]butanamide 49

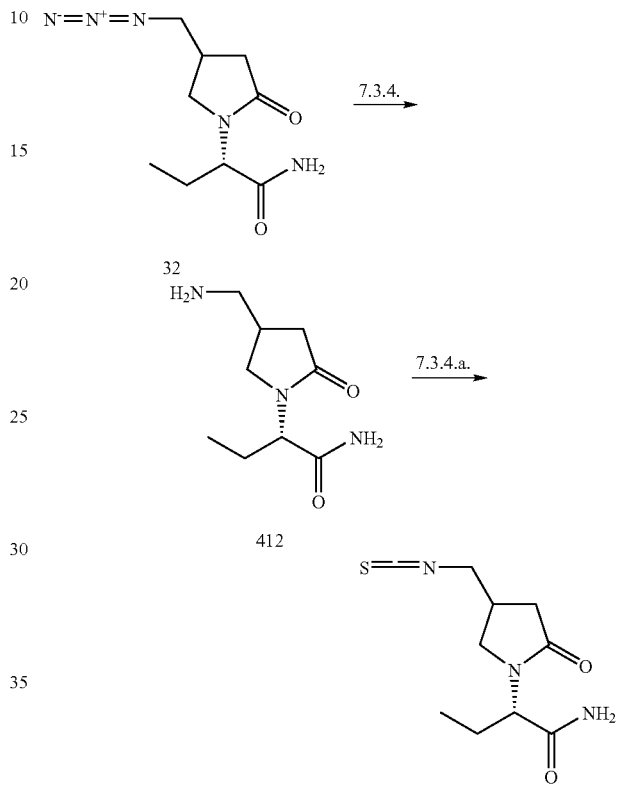

In a 500 ml pressure jar, under inert atmosphere, 900 mg of 10% Pd adsorbed on charcoal are suspended in 100 ml of ethanol. A solution of 8.7 g (38 mmoles) of (2S)-2-[4-(azidomethyl)-2-oxo-1-pyrrolidinyl]butanamide 32 in 150 ml of ethanol is added and the mixture is hydrogenated on a Parr hydrogenator at a maximum of 30 psi $H_2$ pressure for 2 hours. The mixture is degassed, filtered on a Celite/Norite pad, the residue washed with 2×100 ml EtOH and the combined filtrates concentrated to dryness, to give 7.93 g of crude 412, 100% yield, used as such in the next step. GC/MS: 199 (M+).

7.3.4.a. Synthesis of (2S)-2-[4-(isothiocyanatomethyl)-2-oxo-1-pyrrolidinyl]butanamide 49

In a 100 ml 3 necked flask, fitted with magnetic stirrer and reflux condenser under inert atmosphere, 4.5 g (22.7 mmoles, 1 eq) of thiocarbonylimidazole are dissolved in 25 ml of DMF and the mixture cooled down to 0° C. 4.53 g (22.7 mmoles, 1 eq) of (2S)-2-[4-(aminomethyl)-2-oxo-1-pyrrolidinyl]butanamide 412 in 25 ml of DMF are added dropwise over 30 min, the mixture is stirred 3 hours at room temperature and left overnight. The mixture is concentrated to dryness, the residue is dissolved in 20 ml of toluene, concentrated again to dryness, and the residue is purified by Prep LC (350 g $SiO_2$$CH_2Cl_2$/MeOH/$NH_4OH$, 93.4:6:0.6) to give 3.1 g of crude 49. It is triturated in 20 ml of ether, filtered and the residue (1.9 g) crystallised from 15 ml of acetonitrile to give 1.2 g of pure 49 (22%).

The compounds of formula I shown in the following Table may be prepared analogously or as otherwise described herein.

In the table, the stereochemical information is contained in the two columns headed 'configuration data'. The second column indicates whether a compound has no stereogenic center (ACHIRAL), is a pure enantiomer (PURE), a racemate (RAC) or is a mixture of two or more stereoisomers, possibly in unequal proportions (MIXT). The first column contains the stereochemical assignment for each recognised center, following the IUPAC numbering used in the preceding column. A number alone indicates the existence of both configurations at that center. A number followed by 'R' or 'S' indicates the known absolute configuration at that center. A number followed by '§' indicates the existence of only one but unknown absolute configuration at that center. The letter (A, B, C, D) in front is a way of distinguishing the various enantiomers or racemates of the same structure.

In the table, the melting points are in most cases determined by the onset of the DSC curve. When a visual (fusionometer) melting point is given, the value is in parenthesis.

In the table, the numbers in the column 'synthesis' refer to the synthesis actually used for the most important compounds. Slight variations might be needed to obtain analoguous compounds. Such modifications are within the competence of any person well skilled in the art of organic synthesis.

| Cmpd. number | IUPAC chemical name | Configuration data | |
|---|---|---|---|
| 1 | 2-(4-ethyl-2-oxo-4-phenyl-1-pyrrolidinyl)acetamide | 4 | RAC |
| 2 | 2-(2-oxo-4-phenyl-1-pyrrolidinyl)acetamide | 4 | RAC |
| 3 | 2-(4-methyl-2-oxo-1-pyrrolidinyl)acetamide | 4 | RAC |
| 4 | 2-(4-methyl-2-oxo-1-pyrrolidinyl)propanamide | 2,4 | MIXT |
| 5 | 2-(4,4-dimethyl-2-oxo-1-pyrrolidinyl)propanamide | | ACHIRAL |
| 6 | (2S)-2-[4-(hydroxymethyl)-2-oxo-1-pyrrolidinyl]butanamide | A - 2S,4§ | PURE |
| 7 | (2S)-2-[4-(hydroxymethyl)-2-oxo-1-pyrrolidinyl]butanamide | B - 2S,4§ | PURE |
| 8 | (2S)-2-[4-(bromomethyl)-2-oxo-1-pyrrolidinyl]butanamide | A - 2S,4§ | PURE |
| 9 | (2S)-2-[4-(bromomethyl)-2-oxo-1-pyrrolidinyl]butanamide | B - 2S,4§ | PURE |
| 10 | (2S)-2-[(4R)-4-(iodomethyl)-2-oxopyrrolidinyl]butanamide | 2S,4R | PURE |
| 11 | methyl 1-[(1S)-1-(aminocarbonyl)propyl]-5-oxo-3-pyrrolidinecarboxylate | A - 1S,3§ | PURE |
| 12 | methyl 1-[(1S)-1-(aminocarbonyl)propyl]-5-oxo-3-pyrrolidinecarboxylate | B - 1S,3§ | PURE |
| 13 | (2S)-2-{2-oxo-4-[(4-phenyl-1-piperazinyl)methyl]-1-pyrrolidinyl}butanamide | A - 2S,3§ | PURE |
| 14 | (2S)-2-{2-oxo-4-[(4-phenyl-1-piperazinyl)methyl]-1-pyrrolidinyl}butanamide | B - 2S,4§ | PURE |
| 15 | (2S)-2-[2-oxo-4-(1-pyrrolidinylmethyl)-1-pyrrolidinyl]butanamide | A - 2S,4§ | PURE |
| 16 | (2S)-2-[2-oxo-4-(1-pyrrolidinylmethyl)-1-pyrrolidinyl]butanamide | B - 2S,4§ | PURE |
| 17 | (2S)-2-[2-oxo-4-(4-thiomorpholinylmethyl)-1-pyrrolidinyl]butanamide | A - 2S,4§ | PURE |
| 18 | (2S)-2-[2-oxo-4-(phenoxymethyl)-1-pyrrolidinyl]butanamide | A - 2S,4§ | PURE |
| 19 | (2S)-2-{4-[(isopropylsulfanyl)methyl]-2-oxo-1-pyrrolidinyl}butanamide | B - 2S,4§ | PURE |
| 20 | (2S)-2-(4-benzyl-2-oxo-1-pyrrolidinyl)butanamide | A - 2S,4§ | PURE |
| 21 | (2S)-2-(4-benzyl-2-oxo-1-pyrrolidinyl)butanamide | B - 2S,4§ | PURE |
| 22 | (2S)-2-(2-oxo-4-phenyl-1-pyrrolidinyl)butanamide | A - 2S,4§ | PURE |
| 23 | (2S)-2-(2-oxo-4-phenyl-1-pyrrolidinyl)butanamide | B - 2S,4§ | PURE |
| 24 | (2S)-2-{4-[(isopropylsulfanyl)methyl]-2-oxo-1-pyrrolidinyl}butanamide | A - 2S,4§ | PURE |
| 25 | (2S)-2-(4-isopropyl-2-oxo-1-pyrrolidinyl)butanamide | A - 2S,4§ | PURE |
| 26 | (2S)-2-(4-isopropyl-2-oxo-1-pyrrolidinyl)butanamide | B - 2S,4§ | PURE |
| 27 | (2S)-2-[4-(iodomethyl)-2-oxo-1-pyrrolidinyl]butanamide | B - 2S,4§ | PURE |
| 28 | 2-(4-cyano-2-oxo-1-pyrrolidinyl)butanamide | A - 2,4 | RAC |
| 29 | 2-(4-cyano-2-oxo-1-pyrrolidinyl)butanamide | B - 2,4 | RAC |
| 30 | (2S)-2-[4-(chloromethyl)-2-oxo-1-pyrrolidinyl]butanamide | A - 2S,4§ | PURE |
| 31 | {1-[(1S)-1-(aminocarbonyl)propyl]-5-oxo-3-pyrrolidinyl}methyl 4-methylbenzenesulfonate | A - 1S,3§ | PURE |
| 32 | (2S)-2-[(4R)-4-(azidomethyl)-2-oxopyrrolidinyl]butanamide | 2S,4R | PURE |
| 33 | 2-[4-(2,2-dibromovinyl)-2-oxo-1-pyrrolidinyl]butanamide | 2,4 | MIXT |
| 34 | 1-[(1S)-1-(aminocarbonyl)propyl]-5-oxo-3-pyrrolidinecarboxamide | A - 1S,3§ | PURE |
| 35 | (2S)-2-(4-methyl-2-oxo-1-pyrrolidinyl)butanamide | A - 2S,4§ | PURE |
| 36 | (2S)-2-(4-methyl-2-oxo-1-pyrrolidinyl)butanamide | B - 2S,4§ | PURE |
| 37 | {1-[(1S)-1-(aminocarbonyl)propyl]-5-oxo-3-pyrrolidinyl}methyl methanesulfonate | A - 1S,3§ | PURE |
| 38 | {1-[(1S)-1-(aminocarbonyl)propyl]-5-oxo-3-pyrrolidinyl}methyl nitrate | A - 1S,3§ | PURE |
| 39 | (2S)-2-[2-oxo-4-(1H-tetraazol-1-ylmethyl)-1-pyrrolidinyl]butanamide | A - 2S,4§ | PURE |
| 40 | (2S)-2-[2-oxo-4-(1H-tetraazol-1-ylmethyl)-1-pyrrolidinyl]butanamide | A - 2S,4§ | PURE |
| 41 | 2-(2-oxo-4-vinyl-1-pyrrolidinyl)butanamide | 2,4 | MIXT |
| 42 | (2S)-2-[4-(cyanomethyl)-2-oxo-1-pyrrolidinyl]butanamide | A - 2S,4§ | PURE |
| 43 | 2-{2-oxo-4-[(phenylsulfonyl)methyl]-1-pyrrolidinyl}butanamide | A - 2S,4§ | PURE |
| 44 | (2S)-2-[4-(fluoromethyl)-2-oxo-1-pyrrolidinyl]butanamide | A - 2S,4§ | PURE |
| 45 | {1-[(1S)-1-(aminocarbonyl)propyl]-5-oxo-3-pyrrolidinyl}methyl benzoate | A - 1S,3§ | PURE |
| 46 | (2S)-2-[(4R)-4-(2,2-dibromovinyl)-2-oxopyrrolidinyl]butanamide | 2S,4R | PURE |
| 47 | (2S)-2-[(4S)-4-(2,2-dibromovinyl)-2-oxopyrrolidinyl]butanamide | 2S,4S | PURE |
| 48 | 1-[(1S)-1-(aminocarbonyl)propyl]-5-oxo-3-pyrrolidinecarboxylic acid | A - 1S,3§ | PURE |
| 49 | (2S)-2-[4-(isothiocyanatomethyl)-2-oxo-1-pyrrolidinyl]butanamide | A - 2S,4§ | PURE |
| 50 | (2S)-2-[4-(1,3,4-oxadiazol-2-yl)-2-oxo-1-pyrrolidinyl]butanamide | A - 2S,4§ | PURE |
| 51 | 2-[2-oxo-4-(5-sulfanyl-1,3,4-oxadiazol-2-yl)-1-pyrrolidinyl]butanamide | 2,4 | MIXT |
| 52 | (2S)-2-{4-[(5-methyl-1H-1,2,3-triazol-1-yl)methyl]-2-oxo-1-pyrrolidinyl}butanamide | A - 2S,4§ | PURE |
| 53 | 2-[4-(3-methyl-1,2,4-thiadiazol-5-yl)-2-oxo-1-pyrrolidinyl]butanamide | 2,4 | MIXT |

-continued

| | | | |
|---|---|---|---|
| 54 | 2-[4-(4-methyl-1,3-thiazol-2-yl)-2-oxo-1-pyrrolidinyl]butanamide | 2,4 | MIXT |
| 55 | (2S)-2-[2-oxo-4-(1H-1,2,4-triazol-1-ylmethyl)-1-pyrrolidinyl]butanamide | A - 2S,4§ | PURE |
| 56 | 2-[2-oxo-4-(1H-1,2,3-triazol-1-ylmethyl)-1-pyrrolidinyl]butanamide | A - 2,4§ | MIXT |
| 57 | 2-[2-oxo-4-(1H-tetraazol-1-yl)-1-pyrrolidinyl]butanamide | A - 2,4 | RAC |
| 58 | 2-[4-(2-methyl-2H-tetraazol-5-yl)-2-oxo-1-pyrrolidinyl]butanamide | A - 2,4 | RAC |
| 59 | 2-[4-(1-methyl-1H-tetraazol-5-yl)-2-oxo-1-pyrrolidinyl]butanamide | A - 2,4 | RAC |
| 60 | 2-[4-(2-methyl-2H-tetraazol-5-yl)-2-oxo-1-pyrrolidinyl]butanamide | B - 2,4 | RAC |
| 61 | 2-[4-(1-methyl-1H-tetraazol-5-yl)-2-oxo-1-pyrrolidinyl]butanamide | B - 2,4 | RAC |
| 62 | 2-[4-(5-methyl-1,3-oxazol-2-yl)-2-oxo-1-pyrrolidinyl]butanamide | A - 2,4 | RAC |
| 63 | 2-[4-(5-methyl-1,3-oxazol-2-yl)-2-oxo-1-pyrrolidinyl]butanamide | B - 2,4 | RAC |
| 64 | 2-[2-oxo-4-(1,3-thiazol-2-yl)-1-pyrrolidinyl]butanamide | 2,4 | MIXT |
| 65 | 2-[2-oxo-4-(4H-1,2,4-triazol-4-yl)-1-pyrrolidinyl]butanamide | A - 2,4 | RAC |
| 66 | 2-[2-oxo-4-(4H-1,2,4-triazol-4-yl)-1-pyrrolidinyl]butanamide | B - 2,4 | RAC |
| 67 | 2-[2-oxo-4-(1H-tetraazol-1-yl)-1-pyrrolidinyl]butanamide | B - 2,4 | RAC |
| 68 | (2S)-2-[4-(4-methoxyphenyl)-2-oxo-1-pyrrolidinyl]butanamide | A - 2S,4§ | PURE |
| 69 | (2S)-2-[4-(4-methoxyphenyl)-2-oxo-1-pyrrolidinyl]butanamide | B - 2S,4§ | PURE |
| 70 | 2-[2-oxo-4-(3-pyridinylcarbonyl)-1-pyrrolidinyl]butanamide | 2,4 | MIXT |
| 71 | (2S)-2-[2-oxo-4-(2-thienyl)-1-pyrrolidinyl]butanamide | A - 2S,4§ | PURE |
| 72 | (2S)-2-[2-oxo-4-(2-thienyl)-1-pyrrolidinyl]butanamide | B - 2S,4§ | PURE |
| 73 | (2S)-2-[4-(2-methoxyphenyl)-2-oxo-1-pyrrolidinyl]butanamide | A - 2S,4§ | PURE |
| 74 | (2S)-2-[4-(4-nitrophenyl)-2-oxo-1-pyrrolidinyl]butanamide | A - 2S,4§ | PURE |
| 75 | (2S)-2-[4-(3-methoxyphenyl)-2-oxo-1-pyrrolidinyl]butanamide | B - 2S,4§ | PURE |
| 76 | (2S)-2-[4-(4-nitrophenyl)-2-oxo-1-pyrrolidinyl]butanamide | B - 2S,4§ | PURE |
| 77 | (2S)-2-[4-(3-methoxyphenyl)-2-oxo-1-pyrrolidinyl]butanamide | A - 2S,4§ | PURE |
| 78 | (2S)-2-[4-(2-methoxyphenyl)-2-oxo-1-pyrrolidinyl]butanamide | B - 2S,4§ | PURE |
| 79 | (2S)-2-[4-(4-aminophenyl)-2-oxo-1-pyrrolidinyl]butanamide | A - 2S,4§ | PURE |
| 80 | 2-{2-oxo-4-[(E)-2-phenylethenyl]-1-pyrrolidinyl}butanamide | 2,4 | MIXT |
| 81 | (2S)-2-[4-(4-azidophenyl)-2-oxo-1-pyrrolidinyl]butanamide | A - 2S,4§ | PURE |
| 82 | (2S)-2-[4-(4-azidophenyl)-2-oxo-1-pyrrolidinyl]butanamide | B - 2S,4§ | PURE |
| 83 | (2S)-2-[2-oxo-4-(3-thienyl)-1-pyrrolidinyl]butanamide | A - 2S,4§ | PURE |
| 84 | (2R)-2-[2-oxo-4-(2-thienyl)-1-pyrrolidinyl]butanamide | B - 2R,4§ | PURE |
| 85 | (2R)-2-[2-oxo-4-(2-thienyl)-1-pyrrolidinyl]butanamide | A - 2R,4§ | PURE |
| 86 | (2S)-2-[4-(3-azidophenyl)-2-oxo-1-pyrrolidinyl]butanamide | A - 2S,4§ | PURE |
| 87 | (2S)-2-[4-(3-azidophenyl)-2-oxo-1-pyrrolidinyl]butanamide | B - 2S,4§ | PURE |
| 88 | (2S)-2-[2-oxo-4-(3-thienyl)-1-pyrrolidinyl]butanamide | B - 2S,4§ | PURE |
| 89 | (2S)-2-[4-(4-aminophenyl)-2-oxo-1-pyrrolidinyl]butanamide | B - 2S,4§ | PURE |
| 90 | (2S)-2-[4-(3-aminophenyl)-2-oxo-1-pyrrolidinyl]butanamide | A - 2S,4§ | PURE |
| 91 | (2S)-2-[4-(3-aminophenyl)-2-oxo-1-pyrrolidinyl]butanamide | B - 2S,4§ (1 HCl) | PURE |
| 92 | (2S)-2-[(4S)-2-oxo-4-vinylpyrrolidinyl]butanamide | 2S,4S | PURE |
| 93 | (2S)-2-[(4R)-2-oxo-4-vinylpyrrolidinyl]butanamide | 2S,4R | PURE |
| 94 | 2-[4-(2-bromophenyl)-2-oxo-1-pyrrolidinyl]butanamide | A - 2S,4§ | PURE |
| 95 | 2-[4-(2-bromophenyl)-2-oxo-1-pyrrolidinyl]butanamide | B - 2S,4§ | PURE |
| 96 | 2-[2-oxo-4-(3-pyridinyl)-1-pyrrolidinyl]butanamide | 2,4 | MIXT |
| 97 | 2-[4-(1-oxido-3-pyridinyl)-2-oxo-1-pyrrolidinyl]butanamide | 2,4 | MIXT |
| 98 | (2S)-2-(4-[1,1'-biphenyl]-4-yl-2-oxo-1-pyrrolidinyl)butanamide | A - 2S,4§ | PURE |
| 99 | (2S)-2-(4-[1,1'-biphenyl]-4-yl-2-oxo-1-pyrrolidinyl)butanamide | B - 2S,4§ | PURE |
| 100 | (2S)-2-{4-[(methylsulfanyl)methyl]-2-oxo-1-pyrrolidinyl}butanamide | A - 2S,4§ | PURE |
| 101 | (2S)-2-[4-(1-naphthyl)-2-oxo-1-pyrrolidinyl]butanamide | A - 2S,4§ | PURE |
| 102 | (2S)-2-[4-(1-naphthyl)-2-oxo-1-pyrrolidinyl]butanamide | B - 2S,4§ | PURE |
| 103 | 2-[4-(iodomethyl)-2-oxo-1-pyrrolidinyl]butanamide | 2,4 | MIXT |
| 104 | 2-[4-(chloromethyl)-2-oxo-1-pyrrolidinyl]butanamide | 2,4 | MIXT |
| 105 | (2S)-2-[(4R)-4-(iodomethyl)-2-oxo-1-pyrrolidinyl]pentanamide | A - 2S,4R | PURE |
| 106 | (2S)-2-[(4S)-4-(iodomethyl)-2-oxo-1-pyrrolidinyl]pentanamide | B - 2S,4S | PURE |
| 107 | (2S)-2-[4-(3-amino-2,4,6-tribromophenyl)-2-oxo-1-pyrrolidinyl]butanamide | A - 2S,4§ | PURE |
| 108 | (2S)-2-(4-hexyl-2-oxo-1-pyrrolidinyl)butanamide | A - 2,4 | RAC |
| 109 | (2S)-2-(4-hexyl-2-oxo-1-pyrrolidinyl)butanamide | B - 2,4 | RAC |
| 110 | (2S)-2-[(4R)-4-(iodomethyl)-2-oxopyrrolidinyl]propanamide | 2S,4R | PURE |
| 111 | (2S)-2-[(4S)-4-(iodomethyl)-2-oxopyrrolidinyl]propanamide | 2S,4S | PURE |
| 112 | 2-(4-hexyl-2-oxo-1-pyrrolidinyl)propanamide | A - 2,4 | RAC |
| 113 | 2-(4-hexyl-2-oxo-1-pyrrolidinyl)propanamide | B - 2,4 | RAC |
| 114 | 2-(4-hexyl-2-oxo-1-pyrrolidinyl)tetradecanamide | A - 2,4 | RAC |
| 115 | 2-(4-hexyl-2-oxo-1-pyrrolidinyl)tetradecanamide | B - 2,4 | RAC |
| 116 | 2-(4-hexyl-2-oxo-1-pyrrolidinyl)hexanamide | A - 2,4 | RAC |
| 117 | 2-(4-hexyl-2-oxo-1-pyrrolidinyl)pentanamide | B - 2,4 | RAC |
| 118 | 2-(4-hexyl-2-oxo-1-pyrrolidinyl)heptanamide | 2,4 | MIXT |
| 119 | 2-(2-oxo-4-propyl-1-pyrrolidinyl)propanamide | 2,4 | MIXT |
| 120 | 2-(2-oxo-4-propyl-1-pyrrolidinyl)octanamide | 2,4 | MIXT |
| 121 | 2-(2-oxo-4-propyl-1-pyrrolidinyl)hexanamide | 2,4 | MIXT |
| 122 | 2-(2-oxo-4-propyl-1-pyrrolidinyl)hexanamide | 2,4 | MIXT |
| 123 | 2-(2-oxo-4-propyl-1-pyrrolidinyl)hexanamide | 2,4 | MIXT |
| 124 | 2-(2-oxo-4-propyl-1-pyrrolidinyl)pentanamide | 2,4 | MIXT |
| 125 | 2-(2-oxo-4-propyl-1-pyrrolidinyl)heptanamide | 2,4 | MIXT |
| 126 | 2-(2-oxo-4-propyl-1-pyrrolidinyl)heptanamide | 2,4 | MIXT |
| 127 | 2-(2-oxo-4-propyl-1-pyrrolidinyl)butanamide | A - 2,4 | RAC |
| 128 | 2-(2-oxo-4-propyl-1-pyrrolidinyl)acetamide | 4 | RAC |
| 129 | (2S)-2-{4-[(methylsulfonyl)methyl]-2-oxo-1-pyrrolidinyl}butanamide | A - 2S,4§ | PURE |
| 130 | 2-(2-oxo-4-propyl-1-pyrrolidinyl)-2-phenylacetamide | A - 2,4 | RAC |
| 131 | 2-(2-oxo-4-propyl-1-pyrrolidinyl)-2-phenylacetamide | B - 2,4 | RAC |
| 132 | 2-(2-oxo-4-pentyl-1-pyrrolidinyl)tetradecanamide | 2,4 | MIXT |

-continued

| | | | |
|---|---|---|---|
| 133 | 2-(2-oxo-4-pentyl-1-pyrrolidinyl)octanamide | A - 2,4 | RAC |
| 134 | 2-(2-oxo-4-pentyl-1-pyrrolidinyl)octanamide | B - 2,4 | RAC |
| 135 | 2-(2-oxo-4-pentyl-1-pyrrolidinyl)hexanamide | A - 2,4 | RAC |
| 136 | 2-(2-oxo-4-pentyl-1-pyrrolidinyl)hexanamide | B - 2,4 | RAC |
| 137 | 2-(2-oxo-4-pentyl-1-pyrrolidinyl)pentanamide | A - 2,4 | RAC |
| 138 | 2-(2-oxo-4-pentyl-1-pyrrolidinyl)pentanamide | B - 2,4 | RAC |
| 139 | 2-(2-oxo-4-pentyl-1-pyrrolidinyl)heptanamide | 2,4 | MIXT |
| 140 | 2-(2-oxo-4-pentyl-1-pyrrolidinyl)-2-phenylacetamide | 2,4 | MIXT |
| 141 | 2-(2-oxo-4-pentyl-1-pyrrolidinyl)butanamide | A - 2,4 | RAC |
| 142 | 2-(2-oxo-4-pentyl-1-pyrrolidinyl)butanamide | B - 2,4 | RAC |
| 143 | 2-(2-oxo-4-pentyl-1-pyrrolidinyl)acetamide | 4 | RAC |
| 144 | (2S)-2-[(4R)-4-(iodomethyl)-2-oxopyrrolidinyl]-N,N-dimethylbutanamide | 2S,4R | PURE |
| 145 | (2S)-2-[(4S)-4-(iodomethyl)-2-oxopyrrolidinyl]-N,N-dimethylbutanamide | 2S,4S | PURE |
| 146 | (2S)-2-[(4R)-4-(iodomethyl)-2-oxopyrrolidinyl]-N-methylbutanamide | 2S,4R | PURE |
| 147 | 2-[4-(1,3-benzodioxol-5-yl)-2-oxo-1-pyrrolidinyl]butanamide | 2,4 | MIXT |
| 148 | (2S)-2-(4-neopentyl-2-oxo-1-pyrrolidinyl)butanamide | A - 2S,4§ | PURE |
| 149 | (2S)-2-(4-neopentyl-2-oxo-1-pyrrolidinyl)butanamide | B - 2S,4§ | PURE |
| 150 | (2S)-2-{4-[(methylsulfinyl)methyl]-2-oxo-1-pyrrolidinyl}butanamide | A - 2S,4§ | PURE |
| 151 | (2S)-2-(4-ethyl-2-oxo-1-pyrrolidinyl)butanamide | A - 2S,4§ | PURE |
| 152 | (2S)-2-(4-ethyl-2-oxo-1-pyrrolidinyl)butanamide | B - 2S,4§ | PURE |
| 153 | 2-{4-[(benzyloxy)methyl]-2-oxo-1-pyrrolidinyl}butanamide | A - 2,4 | RAC |
| 154 | 2-{4-[(benzyloxy)methyl]-2-oxo-1-pyrrolidinyl}butanamide | B - 2,4 | RAC |
| 155 | (2S)-2-[(4S)-4-(iodomethyl)-2-oxopyrrolidinyl]-N-methylbutanamide | 2S,4S | PURE |
| 156 | 2-[4-(2,2-difluorovinyl)-2-oxo-1-pyrrolidinyl]butanamide | 2,4 | MIXT |
| 157 | 2-[4-(2,2-difluoroethyl)-2-oxo-1-pyrrolidinyl]butanamide | 2,4 | MIXT |
| 158 | (2S)-2-[(4S)-2-oxo-4-propylpyrrolidinyl]butanamide | 2S,4S | PURE |
| 159 | (2S)-2-[(4R)-2-oxo-4-propylpyrrolidinyl]butanamide | 2S,4R | PURE |
| 160 | 2-[2-oxo-4-(trifluoromethyl)-1-pyrrolidinyl]butanamide | A - 2,4 | RAC |
| 161 | 2-[2-oxo-4-(trifluoromethyl)-1-pyrrolidinyl]butanamide | B - 2,4 | RAC |
| 162 | 2-{4-[(Z)-2-fluoroethenyl]-2-oxo-1-pyrrolidinyl}butanamide | 2,4 | MIXT |
| 163 | 2-[4-(2-methyl-1-propenyl)-2-oxo-1-pyrrolidinyl]butanamide | 2,4 | MIXT |
| 164 | 2-(4-butyl-2-oxo-1-pyrrolidinyl)butanamide | 2,4 | MIXT |
| 165 | 2-[4-(cyclopropylmethyl)-2-oxo-1-pyrrolidinyl]butanamide | 2,4 | MIXT |
| 166 | 2-(4-isobutyl-2-oxo-1-pyrrolidinyl)butanamide | 2,4 | MIXT |
| 167 | 2-[4-(2-chloro-6-fluorophenyl)-2-oxo-1-pyrrolidinyl]butanamide | 2,4 | MIXT |
| 168 | 2-[4-(2-naphthyl)-2-oxo-1-pyrrolidinyl]butanamide | 2,4 | MIXT |
| 169 | 2-[4-(4-chlorophenyl)-2-oxo-1-pyrrolidinyl]butanamide | 2,4 | MIXT |
| 170 | 2-[4-(3-chlorophenyl)-2-oxo-1-pyrrolidinyl]butanamide | 2,4 | MIXT |
| 171 | 2-{2-oxo-4-[2-(trifluoromethyl)phenyl]-1-pyrrolidinyl}butanamide | 2,4 | MIXT |
| 172 | 2-[4-(4-methylphenyl)-2-oxo-1-pyrrolidinyl]butanamide | 2,4 | MIXT |
| 173 | 2-[4-(2-fluorophenyl)-2-oxo-1-pyrrolidinyl]butanamide | 2,4 | MIXT |
| 174 | 2-[4-(3-methylphenyl)-2-oxo-1-pyrrolidinyl]butanamide | 2,4 | MIXT |
| 175 | (2S)-2-[2-oxo-4-(2-phenylethyl)-1-pyrrolidinyl]butanamide | B - 2S,4§ | PURE |
| 176 | (2S)-2-[2-oxo-4-(2-phenylethyl)-1-pyrrolidinyl]butanamide | A - 2S,4§ | PURE |
| 177 | 2-(4-hexyl-2-oxo-1-pyrrolidinyl)octanamide | 2,4 | MIXT |
| 178 | 2-(4-hexyl-2-oxo-1-pyrrolidinyl)hexanamide | B - 2,4 | RAC |
| 179 | 2-(4-hexyl-2-oxo-1-pyrrolidinyl)pentanamide | A - 2,4 | RAC |
| 180 | (2S)-2-[4-(3-bromophenyl)-2-oxo-1-pyrrolidinyl]butanamide | A - 2S,4§ | PURE |
| 181 | (2S)-2-[4-(3-bromophenyl)-2-oxo-1-pyrrolidinyl]butanamide | B - 2S,4§ | PURE |
| 182 | 2-{4-[3,5-bis(trifluoromethyl)phenyl]-2-oxo-1-pyrrolidinyl}butanamide | A - 2§,4§ | PURE |
| 183 | 2-{4-[3,5-bis(trifluoromethyl)phenyl]-2-oxo-1-pyrrolidinyl}butanamide | B - 2§,4§ | PURE |
| 184 | 2-{4-[3,5-bis(trifluoromethyl)phenyl]-2-oxo-1-pyrrolidinyl}butanamide | C - 2§,4§ | PURE |
| 185 | 2-{4-[3,5-bis(trifluoromethyl)phenyl]-2-oxo-1-pyrrolidinyl}butanamide | D - 2§,4§ | PURE |
| 186 | 2-[4-(3,4-dichlorophenyl)-2-oxo-1-pyrrolidinyl]butanamide | A - 2§,4§ | PURE |
| 187 | 2-[4-(3,4-dichlorophenyl)-2-oxo-1-pyrrolidinyl]butanamide | B - 2§,4§ | PURE |
| 188 | 2-[4-(2,4-dichlorophenyl)-2-oxo-1-pyrrolidinyl]butanamide | A - 2,4 | RAC |
| 189 | 2-[4-(2,4-dichlorophenyl)-2-oxo-1-pyrrolidinyl]butanamide | B - 2,4 | RAC |
| 190 | (2S)-2-[4-(3,5-dibromophenyl)-2-oxo-1-pyrrolidinyl]butanamide | B - 2S,4§ | PURE |
| 191 | 2-(2-oxo-4-{3-[(trifluoromethyl)sulfanyl]phenyl}-1-pyrrolidinyl)butanamide | A - 2§,4§ | PURE |
| 192 | 2-(2-oxo-4-{3-[(trifluoromethyl)sulfanyl]phenyl}-1-pyrrolidinyl)butanamide | B - 2§,4§ | PURE |
| 193 | 2-(2-oxo-4-{3-[(trifluoromethyl)sulfanyl]phenyl}-1-pyrrolidinyl)butanamide | C - 2§,4§ | PURE |
| 194 | 2-(2-oxo-4-{3-[(trifluoromethyl)sulfanyl]phenyl}-1-pyrrolidinyl)butanamide | D - 2§,4§ | PURE |
| 195 | 2-[4-(2-furyl)-2-oxo-1-pyrrolidinyl]butanamide | A - 2,4 | RAC |
| 196 | 2-[4-(2-furyl)-2-oxo-1-pyrrolidinyl]butanamide | B - 2,4 | RAC |
| 197 | (2S)-2-[2-oxo-4-(3-phenylpropyl)-1-pyrrolidinyl]butanamide | 2S,4 | MIXT |
| 198 | (2S)-2-[4-(3,5-dibromophenyl)-2-oxo-1-pyrrolidinyl]butanamide | A - 2S,4§ | PURE |
| 199 | 2-[4-(3,4-dichlorophenyl)-2-oxo-1-pyrrolidinyl]butanamide | C - 2§,4§ | PURE |
| 200 | 2-[4-(3,4-dichlorophenyl)-2-oxo-1-pyrrolidinyl]butanamide | D - 2§,4§ | PURE |
| 201 | 2-(2-oxo-4-propyl-1-pyrrolidinyl)butanamide | 2,4 | MIXT |
| 202 | 2-[4-(3-chlorophenyl)-2-oxo-1-pyrrolidinyl]butanamide | C - 2§,4§ | PURE |
| 203 | 2-[4-(3-chlorophenyl)-2-oxo-1-pyrrolidinyl]butanamide | B - 2§,4§ | PURE |
| 204 | 2-[4-(3-chlorophenyl)-2-oxo-1-pyrrolidinyl]butanamide | A - 2§,4§ | PURE |
| 205 | 2-[4-(3-chlorophenyl)-2-oxo-1-pyrrolidinyl]butanamide | D - 2§,4§ | PURE |
| 206 | 2-(4-ethynyl-2-oxo-1-pyrrolidinyl)butanamide | A - 2S,4§ | PURE |
| 207 | 2-(4-ethynyl-2-oxo-1-pyrrolidinyl)butanamide | B - 2S,4§ | PURE |
| 208 | 2-[4-(2-fluorophenyl)-2-oxo-1-pyrrolidinyl]butanamide | A - 2§,4§ | PURE |
| 209 | 2-[4-(2-fluorophenyl)-2-oxo-1-pyrrolidinyl]butanamide | C - 2§,4§ | PURE |
| 210 | 2-[4-(2-fluorophenyl)-2-oxo-1-pyrrolidinyl]butanamide | B - 2§,4§ | PURE |
| 211 | 2-[4-(2-fluorophenyl)-2-oxo-1-pyrrolidinyl]butanamide | D - 2§,4§ | PURE |
| 212 | (2S)-2-[4-(cyclopropylmethyl)-2-oxo-1-pyrrolidinyl]butanamide | A - 2S,4§ | PURE |

| | | | |
|---|---|---|---|
| 213 | (2S)-2-[(4S)-4-(2,2-difluorovinyl)-2-oxopyrrolidinyl]butanamide | 2S,4S | PURE |
| 214 | (2S)-2-[2-oxo-4-(3,3,3-trifluoropropyl)-1-pyrrolidinyl]butanamide | A - 2S,4§ | PURE |
| 215 | (2S)-2-[2-oxo-4-(3,3,3-trifluoropropyl)-1-pyrrolidinyl]butanamide | B - 2S,4§ | PURE |
| 216 | 2-[4-(3-methylphenyl)-2-oxo-1-pyrrolidinyl]butanamide | A - 2§,4§ | PURE |
| 217 | 2-[4-(3-methylphenyl)-2-oxo-1-pyrrolidinyl]butanamide | C - 2§,4§ | PURE |
| 218 | 2-[4-(3-methylphenyl)-2-oxo-1-pyrrolidinyl]butanamide | B - 2§,4§ | PURE |
| 219 | 2-[4-(3-methylphenyl)-2-oxo-1-pyrrolidinyl]butanamide | D - 2§,4§ | PURE |
| 220 | 2-[2-oxo-4-(5-pyrimidinyl)-1-pyrrolidinyl]butanamide | 2,4 | MIXT |
| 221 | (2S)-2-[4-(cyclopropylmethyl)-2-oxo-1-pyrrolidinyl]butanamide | B - 2S,4§ | PURE |
| 222 | (2S)-2-[(4R)-4-(2,2-difluorovinyl)-2-oxopyrrolidinyl]butanamide | 2S,4R | PURE |
| 223 | (2S)-2-[2-oxo-4-(1H-pyrrol-1-yl)-1-pyrrolidinyl]butanamide | B - 2S,4§ | PURE |
| 224 | (2S)-2-(4-allyl-2-oxo-1-pyrrolidinyl)butanamide | B - 2S,4§ | PURE |
| 225 | (2S)-2-[4-(2-iodopropyl)-2-oxo-1-pyrrolidinyl]butanamide | A - 2S,4§ | PURE |
| 226 | (2S)-2-[4-(2-iodopropyl)-2-oxo-1-pyrrolidinyl]butanamide | B - 2S,4§ | PURE |
| 227 | (2S)-2-[4-(methoxymethyl)-2-oxo-1-pyrrolidinyl]butanamide | B - 2S,4§ | PURE |
| 228 | (2S)-2-(4-allyl-2-oxo-1-pyrrolidinyl)butanamide | A - 2S,4§ | PURE |
| 229 | (2S)-2-[2-oxo-4-(2-oxopropyl)-1-pyrrolidinyl]butanamide | A - 2S,4§ | PURE |
| 230 | (2S)-2-[2-oxo-4-(2-oxopropyl)-1-pyrrolidinyl]butanamide | B - 2S,4§ | PURE |
| 231 | (2S)-2-[(4S)-4-(2-hydroxypropyl)-2-oxopyrrolidinyl]butanamide | A - 2S,4S,2§ | PURE |
| 232 | (2S)-2-[(4S)-4-(2-hydroxypropyl)-2-oxopyrrolidinyl]butanamide | B - 2S,4S,2§ | PURE |
| 233 | (2S)-2-[(4R)-4-(2-hydroxypropyl)-2-oxopyrrolidinyl]butanamide | B - 2S,4R,2§ | PURE |
| 234 | (2S)-2-[4-(2-bromo-1H-pyrrol-1-yl)-2-oxo-1-pyrrolidinyl]butanamide | B - 2S,4§ | PURE |
| 235 | 2-[4-(3-azido-2,4,6-trifluorophenyl)-2-oxo-1-pyrrolidinyl]butanamide | A - 2,4 | RAC |
| 236 | 2-[4-(3-azido-2,4,6-trifluorophenyl)-2-oxo-1-pyrrolidinyl]butanamide | B - 2,4 | RAC |
| 237 | (2S)-2-[4-(2,5-dibromo-1H-pyrrol-1-yl)-2-oxo-1-pyrrolidinyl]butanamide | B - 2S,4§ | PURE |
| 238 | (2R)-2-[(4S)-2-oxo-4-propylpyrrolidinyl]butanamide | 2R,4S | PURE |
| 239 | (2R)-2-[(4R)-2-oxo-4-propylpyrrolidinyl]butanamide | 2R,4R | PURE |
| 240 | 2-(4-ethyl-2-oxo-4-phenyl-1-pyrrolidinyl)butanamide | A - 2§,4§ | PURE |
| 241 | 2-(4-ethyl-2-oxo-4-phenyl-1-pyrrolidinyl)butanamide | B - 2§,4§ | PURE |
| 242 | 2-(4-ethyl-2-oxo-4-phenyl-1-pyrrolidinyl)butanamide | C - 2§,4§ | PURE |
| 243 | 2-(4-ethyl-2-oxo-4-phenyl-1-pyrrolidinyl)butanamide | D - 2§,4§ | PURE |
| 244 | (2R)-2-[4-(methoxymethyl)-2-oxo-1-pyrrolidinyl]butanamide | A - 2R,4§ | PURE |
| 245 | 2-[4-(methoxymethyl)-2-oxo-1-pyrrolidinyl]butanamide | A - 2§,4§ | PURE |
| 246 | 2-[4-(methoxymethyl)-2-oxo-1-pyrrolidinyl]butanamide | B - 2§,4§ | PURE |
| 247 | 2-{4-[3-(cyclopentyloxy)-4-methoxyphenyl]-2-oxo-1-pyrrolidinyl}butanamide | 2,4 | MIXT |
| 248 | 2-{4-[3-(cyclopentyloxy)-4-methoxyphenyl]-2-oxo-1-pyrrolidinyl}butanamide | 2,4 | MIXT |
| 249 | (2S)-2-[(4R)-4-(2-hydroxypropyl)-2-oxopyrrolidinyl]butanamide | A - 2S,4R,2§ | PURE |
| 250 | (2S)-2-(4-methyl-2-oxo-4-propyl-1-pyrrolidinyl)butanamide | A - 2S,4§ | PURE |
| 251 | (2R)-2-[4-(2,2-dichlorovinyl)-2-oxo-1-pyrrolidinyl]butanamide | A - 2S,4§ | PURE |
| 252 | (2R)-2-[4-(2,2-dichlorovinyl)-2-oxo-1-pyrrolidinyl]butanamide | B - 2S,4§ | PURE |
| 253 | 2-(4-ethyl-4-methyl-2-oxo-1-pyrrolidinyl)butanamide | A - 2S,4§ | PURE |
| 255 | 2-(4-ethyl-4-methyl-2-oxo-1-pyrrolidinyl)butanamide | B - 2S,4§ | PURE |
| 256 | (2S)-2-(2-oxo-4,4-dipropyl-1-pyrrolidinyl)butanamide | 2S | PURE |
| 257 | 2-(3,3-dimethyl-2-oxo-4-phenyl-1-pyrrolidinyl)butanamide | A - 2§,4§ | PURE |
| 258 | 2-(3,3-dimethyl-2-oxo-4-phenyl-1-pyrrolidinyl)butanamide | B - 2§,4§ | PURE |
| 259 | 2-(3,3-dimethyl-2-oxo-4-phenyl-1-pyrrolidinyl)butanamide | C - 2§,4§ | PURE |
| 260 | 2-(3,3-dimethyl-2-oxo-4-phenyl-1-pyrrolidinyl)butanamide | D - 2§,4§ | PURE |
| 261 | (2S)-2-(4-methyl-2-oxo-4-propyl-1-pyrrolidinyl)butanamide | B - 2S,4§ | PURE |
| 262 | (2S)-2-(3-benzyl-2-oxo-1-pyrrolidinyl)butanamide | A - 2S,3§ | PURE |
| 263 | (2R)-2-(3-benzyl-2-oxo-1-pyrrolidinyl)butanamide | B - 2S,3§ | PURE |
| 264 | 2-[4-(bromoethynyl)-2-oxo-1-pyrrolidinyl]butanamide | 2,4§ | MIXT |
| 265 | 2-[(4S)-4-(2,2-difluoropropyl)-2-oxopyrrolidinyl]butanamide | 2,4S | MIXT |
| 266 | (2S)-2-[4-(5-amino-2,4-dibromophenyl)-2-oxo-1-pyrrolidinyl]butanamide | A - 2S,4§ | PURE |
| 267 | (2S)-2-[4-(bromoethynyl)-2-oxo-1-pyrrolidinyl]butanamide | A - 2S,4§ | PURE |
| 268 | (2S)-2-[4-(2,2-difluorovinyl)-2-oxopyrrolidin-1-yl]butanoic acid | B - 2S,4§ | PURE |
| 269 | (2S)-2-(4-ethynyl-2-oxo-1-pyrrolidinyl)butanamide | A - 2S,4§ | PURE |
| 270 | (2S)-2-(3,3-diethyl-2-oxo-1-pyrrolidinyl)butanamide | 2S | PURE |
| 271 | 2-(3-benzyl-3-methyl-2-oxo-1-pyrrolidinyl)butanamide | A - 2,3§ | MIXT |
| 272 | 2-(3-benzyl-3-methyl-2-oxo-1-pyrrolidinyl)butanamide | B - 2,3§ | MIXT |
| 273 | (2S)-2-(3-benzyl-3-methyl-2-oxo-1-pyrrolidinyl)butanamide | A - 2S,3§ | PURE |
| 274 | 2-[4-(5-methyl-2-thienyl)-2-oxo-1-pyrrolidinyl]butanamide | | |
| 275 | 2-[4-(5-acetyl-2-thienyl)-2-oxo-1-pyrrolidinyl]butanamide | | |
| 276 | 2-[4-(5-cyano-2-thienyl)-2-oxo-1-pyrrolidinyl]butanamide | | |
| 277 | 2-[4-(3-bromo-2-thienyl)-2-oxo-1-pyrrolidinyl]butanamide | | |
| 278 | 2-[4-(4-methyl-2-thienyl)-2-oxo-1-pyrrolidinyl]butanamide | | |
| 305 | 2-cyclohexyl-2-(2-oxo-4-propyl-1-pyrrolidinyl)acetamide | 2,4 | MIXT |
| 306 | 3-cyclopropyl-2-(2-oxo-4-propyl-1-pyrrolidinyl)propanamide | 2,4 | MIXT |
| 307 | 4-methyl-2-(2-oxo-4-propyl-1-pyrrolidinyl)-4-pentenamide | 2,4 | MIXT |
| 308 | 5-methyl-2-(2-oxo-4-propyl-1-pyrrolidinyl)hexanamide | 2,4 | MIXT |
| 309 | 2-(2-oxo-4-propyl-1-pyrrolidinyl)hexanamide | 2,4 | MIXT |
| 310 | 3-(4-azidophenyl)-2-(2-oxo-4-propyl-1-pyrrolidinyl)propanamide | 2,4 | MIXT |
| 311 | 3-[4-(allyloxy)phenyl]-2-(2-oxo-4-propyl-1-pyrrolidinyl)propanamide | 2,4 | MIXT |
| 312 | 3-(4-nitrophenyl)-2-(2-oxo-4-propyl-1-pyrrolidinyl)propanamide | 2,4 | MIXT |
| 313 | 2-(2-oxo-4-propyl-1-pyrrolidinyl)-4-phenylbutanamide | 2,4 | MIXT |

-continued

| | | | |
|---|---|---|---|
| 314 | 3-(4-benzoylphenyl)-2-(2-oxo-4-propyl-1-pyrrolidinyl)propanamide | 2,4 | MIXT |
| 315 | 3-(4-hydroxyphenyl)-2-(2-oxo-4-propyl-1-pyrrolidinyl)propanamide | 2,4 | MIXT |
| 316 | 3-(4-methoxyphenyl)-2-(2-oxo-4-propyl-1-pyrrolidinyl)propanamide | 2,4 | MIXT |
| 317 | 3-[1,1'-biphenyl]-4-yl-2-(2-oxo-4-propyl-1-pyrrolidinyl)propanamide | 2,4 | MIXT |
| 318 | 3-(1-naphthyl)-2-(2-oxo-4-propyl-1-pyrrolidinyl)propanamide | 2,4 | MIXT |
| 319 | 3-(4-methylphenyl)-2-(2-oxo-4-propyl-1-pyrrolidinyl)propanamide | 2,4 | MIXT |
| 320 | 3-(4-fluorophenyl)-2-(2-oxo-4-propyl-1-pyrrolidinyl)propanamide | 2,4 | MIXT |
| 321 | 3-(3-fluorophenyl)-2-(2-oxo-4-propyl-1-pyrrolidinyl)propanamide | 2,4 | MIXT |
| 322 | 3-(2-fluorophenyl)-2-(2-oxo-4-propyl-1-pyrrolidinyl)propanamide | 2,4 | MIXT |
| 323 | 3-(3,4-difluorophenyl)-2-(2-oxo-4-propyl-1-pyrrolidinyl)propanamide | 2,4 | MIXT |
| 324 | 3-(4-bromophenyl)-2-(2-oxo-4-propyl-1-pyrrolidinyl)propanamide | 2,4 | MIXT |
| 325 | 3-(4-iodophenyl)-2-(2-oxo-4-propyl-1-pyrrolidinyl)propanamide | 2,4 | MIXT |
| 326 | 3-(4-chlorophenyl)-2-(2-oxo-4-propyl-1-pyrrolidinyl)propanamide | 2,4 | MIXT |
| 327 | 3-(2-chlorophenyl)-2-(2-oxo-4-propyl-1-pyrrolidinyl)propanamide | 2,4 | MIXT |
| 328 | 3-(3-chlorophenyl)-2-(2-oxo-4-propyl-1-pyrrolidinyl)propanamide | 2,4 | MIXT |
| 329 | 3-(4-aminophenyl)-2-(2-oxo-4-propyl-1-pyrrolidinyl)propanamide | 2,4 | MIXT |
| 330 | 4-amino-2-(2-oxo-4-propyl-1-pyrrolidinyl)butanamide | 2,4 | MIXT |
| 331 | 6-({[5-(dimethylamino)-1-naphthyl]sulfonyl}amino)-2-(2-oxo-4-propyl-1-pyrrolidinyl)hexanamide | 2,4 | MIXT |
| 332 | 5-[(aminocarbonyl)amino]-2-(2-oxo-4-propyl-1-pyrrolidinyl)pentanamide | 2,4 | MIXT |
| 333 | 6-[(aminocarbonyl)amino]-2-(2-oxo-4-propyl-1-pyrrolidinyl)hexanamide | 2,4 | MIXT |
| 334 | 2,5-bis(2-oxo-4-propyl-1-pyrrolidinyl)pentanamide | 2,4,4 | MIXT |
| 335 | 2,4-bis(2-oxo-4-propyl-1-pyrrolidinyl)butanamide | 2,4,4 | MIXT |
| 336 | N-[5-amino-5-oxo-4-(2-oxo-4-propyl-1-pyrrolidinyl)pentyl]-2-pyrazinecarboxamide | 4,4 | MIXT |
| 337 | 6-[(6-{[5-(2-oxohexahydro-1H-thieno[3,4-d]imidazol-4-yl)pentanoyl]amino}hexanoyl)amino]-2-(2-oxo-4-propyl-1-pyrrolidinyl)hexanamide | 3a,4,6a,2,4 | MIXT |
| 338 | 5-amino-2-(2-oxo-4-propyl-1-pyrrolidinyl)pentanamide | 2,4 | MIXT |
| 339 | benzyl 3-amino-3-oxo-2-(2-oxo-4-propyl-1-pyrrolidinyl)propylcarbamate | 2,4 | MIXT |
| 340 | allyl 5-amino-5-oxo-4-(2-oxo-4-propyl-1-pyrrolidinyl)pentylcarbamate | 4,4 | MIXT |
| 341 | 5-{[imino(2-oxido-2-oxohydrazino)methyl]amino}-2-(2-oxo-4-propyl-1-pyrrolidinyl)pentanamide | 2,4 | MIXT |
| 342 | 2-chlorobenzyl 6-amino-6-oxo-5-(2-oxo-4-propyl-1-pyrrolidinyl)hexylcarbamate | 5,4 | MIXT |
| 343 | 6-(acetylamino)-2-(2-oxo-4-propyl-1-pyrrolidinyl)hexanamide | 2,4 | MIXT |
| 344 | 2-(2-oxo-4-propyl-1-pyrrolidinyl)-6-[(trifluoroacetyl)amino]hexanamide | 2,4 | MIXT |
| 345 | 6-{[5-(2-oxohexahydro-1H-thieno[3,4-d]imidazol-4-yl)pentanoyl]amino}-2-(2-oxo-4-propyl-1-pyrrolidinyl)hexanamide | 2,4 | MIXT |
| 346 | 4-amino-4-oxo-3-(2-oxo-4-propyl-1-pyrrolidinyl)butanoic acid | 3,4 | MIXT |
| 347 | cyclohexyl 4-amino-4-oxo-3-(2-oxo-4-propyl-1-pyrrolidinyl)butanoate | 3,4 | MIXT |
| 348 | cyclohexyl 5-amino-5-oxo-4-(2-oxo-4-propyl-1-pyrrolidinyl)pentanoate | 4,4 | MIXT |
| 349 | allyl 5-amino-5-oxo-4-(2-oxo-4-propyl-1-pyrrolidinyl)pentanoate | 4,4 | MIXT |
| 350 | 2-(2-oxo-4-propyl-1-pyrrolidinyl)-3-(1,3-thiazol-4-yl)propanamide | 2,4 | MIXT |
| 351 | 2-(2-oxo-4-propyl-1-pyrrolidinyl)-4-pentenamide | 2,4 | MIXT |
| 352 | 3-(1H-indol-3-yl)-2-(2-oxo-4-propyl-1-pyrrolidinyl)propanamide | 2,4 | MIXT |
| 353 | (3R)-3-hydroxy-2-(2-oxo-4-propyl-1-pyrrolidinyl)butanamide | 3R,2,4 | MIXT |
| 354 | 4-(methylsulfanyl)-2-(2-oxo-4-propyl-1-pyrrolidinyl)butanamide | 2,4 | MIXT |
| 355 | 2-(2-oxo-4-propyl-1-pyrrolidinyl)-3-phenylpropanamide | 2,4 | MIXT |
| 356 | 3-[4-(benzyloxy)phenyl]-2-(2-oxo-4-propyl-1-pyrrolidinyl)propanamide | 2,4 | MIXT |
| 357 | 6-amino-2-(2-oxo-4-propyl-1-pyrrolidinyl)hexanamide | 2,4 | MIXT |
| 358 | (2S)-2-[4-(2,2,2-trifluoroethyl)-2-oxo-1-pyrrolidinyl]butanamide | | |
| 359 | (2S)-2-[4-(2-chloro-2,2-difluoroethyl)-2-oxo-1-pyrrolidinyl]butanamide | | |
| 360 | (2S)-2-[4-(2-bromo-2,2-difluoroethyl)-2-oxo-1-pyrrolidinyl]butanamide | | |

| Cmpd. number | Synthesis | Mp (° C.) | LC/MS MH+ | RMN $^1$H |
|---|---|---|---|---|
| 1 | | (127-128) | | |
| 2 | | 143.0 | | |
| 3 | | (116-120) | | |
| 4 | | (106-107) | | |
| 5 | | (146-150) | | |
| 6 | | 144.3 | | |
| 7 | | 116.0 | | |
| 8 | 7.1.1. | 181.3 | | |
| 9 | 7.1.1. | | | [1] |
| 10 | 7.1.1. | 91.4 | | |
| 11 | | | | [2] |
| 12 | | 104.0 | | |
| 13 | | 189.0 | | |
| 14 | | 202.0 | | |
| 15 | | (99.3-100.4) | | |
| 16 | | | | [3] |
| 17 | | 120.0 | | |
| 18 | | 124.4 | | |
| 19 | | | | [4] |
| 20 | | 93.2 | | |
| 21 | | 144.9 | | |

-continued

| | | | |
|---|---|---|---|
| 22 | 1.1.1. then 1.2.1. then 1.2.2. | 89 | |
| 23 | 1.1.1. then 1.2.1. then 1.2.2. | 92.4 | |
| 24 | | | [5] |
| 25 | | 103.8 | |
| 26 | | 98.1 | |
| 27 | 7.1.1. | 107.7 | |
| 28 | | 211.4 | |
| 29 | | 142.8 | |
| 30 | 7.1.1. | 120.3 | |
| 31 | 7.2.1. | 111.7 | |
| 32 | 7.2.2 | 84.8 | |
| 33 | 6.2.2. then 6.3.1. | 134.8 | |
| 34 | | 202.8 | |
| 35 | 4.4 | 73.9 | |
| 36 | 4.4 | 56.9 | |
| 37 | | | [6] |
| 38 | 7.3.1. | 135.0 | |
| 39 | | 181.9 | |
| 40 | 7.2.1. | 82.3 | |
| 41 | 6.2.1 then 6.3.1 | 120.5 | |
| 42 | | 138.1 | |
| 43 | 7.2.2. | | [7] |
| 44 | | 87.1 | |
| 45 | | 109.8 | |
| 46 | 6.2.2 then 6.3.1 | 111.3 | |
| 47 | 6.2.2 then 6.3.1 | 119.0 | |
| 48 | | 152.4 | |
| 49 | 7.3.4.a. | 139.6 | |
| 50 | | | [8] |
| 51 | | 172.8 | |
| 52 | | | [9] |
| 53 | | 128.2 | |
| 54 | | 117.3 | |
| 55 | | | [30] |
| 56 | | 142.6 | |
| 57 | | 228.2 | |
| 58 | | 160.3 | |
| 59 | | 169.2 | |
| 60 | | 147.1 | |
| 61 | | 192.8 | |
| 62 | | 108.7 | |
| 63 | | 167.8 | |
| 64 | 6.8.3. then 6.3.1. | 94.3 | |
| 65 | | 170.9 | |
| 66 | | 186.1 | |
| 67 | | 185.1 | |
| 68 | | 143.0 | |
| 69 | | 147.3 | |
| 70 | | | [10] |
| 71 | 4.1.1. then 4.1.2 | 69.3 | |
| 72 | 4.1.1. then 4.1.2 | 120.5 | |
| 73 | 4.1.1 then 4.1.2.1. then 4.1.2.2. | 112.0 | |
| 74 | 4.1.1. then 4.1.2.1. then 4.1.2.2. | 150.2 | |
| 75 | 4.1.1. then 4.2.1.1. then 4.2.1.2. | 91.3 | |
| 76 | | 146.5 | |
| 77 | | 73.7 | |
| 78 | | 115.0 | |
| 79 | | 129.0 | |
| 80 | | 100.2 | |
| 81 | 4.2.2. | 91.4 | |
| 82 | | 96.6 | |
| 83 | 4.1.1. then 4.1.2. | (93-95) | |
| 84 | | 84.0 | |
| 85 | | 120.4 | |
| 86 | 4.2.2. | 94.5 | |
| 87 | 4.2.2. | 98.0 | |
| 88 | 4.1.1. then 4.1.2 | | [11] |
| 89 | 4.1.1. then 4.2.1.1. then 4.2.1.2. | | [12] |
| 90 | | | [13] |
| 91 | | 226.4 | |

-continued

| | | | | |
|---|---|---|---|---|
| 92 | 6.2.1 then 6.3.1. | 79.0 | | |
| 93 | 6.2.1 then 6.3.1. | 68.3 | | |
| 94 | | 129.4 | | |
| 95 | 1.1.1. then 1.2.1. then 1.2.2. | 165.4 | | |
| 96 | 3.1.1.a. to 3.1.1.g. | 104.3 | | |
| 97 | | 217.4 | | |
| 98 | 4.1.1 then 4.1.2.1. then 4.1.2.2. | | | [14] |
| 99 | | | | [15] |
| 100 | 7.2.2. | | | [16] |
| 101 | | 172.7 | | |
| 102 | | 135.7 | | |
| 103 | 7.1.1. | 171.7 | | |
| 104 | | 166.6 | | |
| 105 | 7.1.1. | 161.7 | | |
| 106 | | 119.4 | | |
| 107 | | | | [17] |
| 108 | | | 255 | |
| 109 | | | 255 | |
| 110 | 7.1.1. | 147 | | |
| 111 | 7.1.1. | 116.3 | | |
| 112 | | | 241 | |
| 113 | | | 241 | |
| 114 | | | 395 | |
| 115 | | | 395 | |
| 116 | | | 283 | |
| 117 | | | 269 | |
| 118 | | | 297 | |
| 119 | 3.1.1.a. to 3.1.1.g. | | 199 | |
| 120 | | | 269 | |
| 121 | | | 241 | |
| 122 | | | 241 | |
| 123 | | | 227 | |
| 124 | | | 227 | |
| 125 | | | 255 | |
| 126 | | | 255 | |
| 127 | 3.1.1.a. to 3.1.1.g. | | 213 | |
| 128 | | | 185 | |
| 129 | | 134.5 | | |
| 130 | | | 261 | |
| 131 | | | 261 | |
| 132 | | | 381 | |
| 133 | | | 297 | |
| 134 | | | 297 | |
| 135 | | | 269 | |
| 136 | | | 269 | |
| 137 | | | 255 | |
| 138 | | | 255 | |
| 139 | | | 284 | |
| 140 | | | 289 | |
| 141 | | | 241 | |
| 142 | 3.1.1a. to 3.1.1.g. | | 241 | |
| 143 | | | 213 | |
| 144 | | 53.8 | | |
| 145 | | 94.8 | | |
| 146 | 7.1.1. | 66.6 | | |
| 147 | | | 291 | |
| 148 | | 187.0 | | |
| 149 | 1.1.1. then 1.2.1. then 1.2.2. | 155.7 | | |
| 150 | | | | [18] |
| 151 | 1.1.1. then 1.2.1. then 1.2.2. | | | [19] |
| 152 | 1.1.1. then 1.2.1. then 1.2.2. | | | [20] |
| 153 | | 101.8 | | |
| 154 | | 119.1 | | |
| 155 | | | | [21] |
| 156 | 6.2.3. then 6.3.1. | 127.2 | | |
| 157 | | 136.8 | | |
| 158 | 2.5. | 82.1 | | |
| 159 | 2.5. | 74.3 | | |
| 160 | | 121.3 | | |
| 161 | | 180.3 | | |

-continued

| | | | | |
|---|---|---|---|---|
| 162 | 6.2.4. then 6.3.1. | 105.0 | | |
| 163 | 6.2.1. then 6.3.2. | 118.1 | | |
| 164 | 2.1.1. then 2.2. | 108.8 | | |
| 165 | 2.1.2. then 2.2. | | | [22] |
| 166 | 6.2.1. then 6.5. then 6.3.1. | 120.2 | | |
| 167 | | | 299/301 | |
| 168 | | | 297 | |
| 169 | 3.1.1.a. to 3.1.1.g. | | 281 | |
| 170 | 3.1.1.a. to 3.1.1.g. | | | |
| 171 | 3.1.1.a. to 3.1.1.g. | | 315 | |
| 172 | | | 261 | |
| 173 | 3.1.1.a. to 3.1.1.g. | | | |
| 174 | 3.1.1.a. to 3.1.1.g. | | | |
| 175 | 1.1.2. then 1.2.1 then 1.2.3. | 89.5 | | |
| 176 | 1.1.2. then 1.2.1 then 1.2.3. | 100.2 | | |
| 177 | | | 311 | |
| 178 | | | 283 | |
| 179 | | | 269 | |
| 180 | 1.1.2.ii then 1.2.1. then 1.2.2. | 99.6 | | |
| 181 | 1.1.2.ii then 1.2.1. then 1.2.2. | 116.9 | | |
| 182 | 3.1.1.a. to 3.1.1.g. | 97.2 | | |
| 183 | | 97.2 | | |
| 184 | | 148.6 | | |
| 185 | 3.1.1.a. to 3.1.1.g. | 148.6 | | |
| 186 | | 177.9 | | |
| 187 | 3.1.1.a. to 3.1.1.g. | 177.9 | | |
| 188 | 3.1.1.a. to 3.1.1.g. | 154.7 | | |
| 189 | | 178.7 | | |
| 190 | 3.1.1.a. to 3.1.1.g. | 201.4 | | |
| 191 | | 138.0 | | |
| 192 | | 137.4 | | |
| 193 | | 84.4 | | |
| 194 | | 83.8 | | |
| 195 | 3.1.1.a. to 3.1.1.g. | | | [23] |
| 196 | 3.1.1.a. to 3.1.1.g. | | | [24] |
| 197 | 1.1.2. then 1.2.1. then 1.2.3. | 92.5 | | |
| 198 | 1.1.2.ii then 1.2.1. then 1.2.2. | 118.6 | | |
| 199 | | 153.8 | | |
| 200 | 3.1.1.a. to 3.1.1.g. | 154.4 | | |
| 201 | 3.1.1.a. to 3.1.1.g. | 99.8 | | |
| 202 | | 111.8 | | |
| 203 | | 113.2 | | |
| 204 | 3.1.1.a. to 3.1.1.g. | 113.4 | | |
| 205 | 3.1.1.a. to 3.1.1.g. | 113.4 | | |
| 206 | | 147 | | |
| 207 | 6.4 | 115.2 | | |
| 208 | | 120.7 | | |
| 209 | 3.1.1.a. to 3.1.1.g. | 123.7 | | |
| 210 | | 154.26 | | |
| 211 | 3.1.1.a. to 3.1.1.g. | 150.9 | | |
| 212 | 2.1.2. then 2.2. | 104.4 | | |
| 213 | 6.2.3. then 6.3.1. | 76.1 | | |
| 214 | 2.1.1. then 2.2. | 120.9 | | |
| 215 | 2.1.1. then 2.2. | 115.9 | | |
| 216 | | | | [25] |

-continued

| | | | |
|---|---|---|---|
| 217 | | | [26] |
| 218 | | 84.26 | |
| 219 | 3.1.1.a. to 3.1.1.g. | 79.4 | |
| 220 | | | [27] |
| 221 | 2.1.2. then 2.2. | 93.9 | |
| 222 | 6.2.3. then 6.3.1. | 104 | |
| 223 | 5.8. | | [28] |
| 224 | 2.1.2.ii then 2.2. | 69.2 | |
| 225 | 2.1.2.ii then 2.2 | 165.4 | |
| 226 | 2.1.2.ii then 2.2 | 171.1 | |
| 227 | | | [29] |
| 228 | 2.1.2.ii then 2.2. | 58.3 | |
| 229 | 2.3. | 90.6 | |
| 230 | | 129.5 | |
| 231 | | 139.4 | |
| 232 | | 106.2 | |
| 233 | | 133.0 | |
| 234 | 5.7 | | [31] |
| 235 | | | [32] |
| 236 | | | [33] |
| 237 | | | [34] |
| 238 | | 74.9 | |
| 239 | | 84.8 | |
| 240 | | 137.2 | |
| 241 | | 137.3 | |
| 242 | | 112 | |
| 243 | | 112.2 | |
| 244 | | 73.5 | |
| 245 | | 58.6 | |
| 246 | | 59.7 | |
| 247 | | | 361 |
| 248 | | | 361 |
| 249 | | | 229 |
| 250 | 2.1.2. then 2.2. | 133.3 | |
| 251 | 6.2.2. then 6.3.1. | 68.2 | |
| 252 | 6.2.2. then 6.3.1. | 96.4 | |
| 253 | | 66.4 | |
| 255 | | 127.6 | |
| 256 | | 116.6 | |
| 257 | | 100 | |
| 258 | | 100.8 | |
| 259 | | 84.2 | |
| 260 | | 87.8 | |
| 261 | | 65.1 | |
| 262 | | | 261 |
| 263 | | 53.5 | |
| 264 | 6.4.1. | 173.2 | |
| 265 | 2.4.2. | 110.9 | |
| 266 | | | 418/420/ 422 |
| 267 | 6.4.1. | 103.9 | |
| 268 | | 87.4 | |
| 269 | 6.4.1. | 146.6 | |
| 270 | | | 227 |
| 271 | | 118 | |
| 272 | | | 275 |
| 273 | | 56.8 | |
| 274 | | | |
| 275 | | | |
| 276 | | | |
| 277 | | | |
| 278 | | | |
| 305 | 1.3.1. then 1.3.2. | | 267 |
| 306 | 1.3.1. then 1.3.2. | | 239 |
| 307 | 1.3.1. then 1.3.2. | | 239 |
| 308 | 1.3.1. then 1.3.2. | | 255 |
| 309 | 1.3.1. then 1.3.2. | | 241 |
| 310 | 1.3.1. then 1.3.2. | | 316 |
| 311 | 1.3.1. then 1.3.2. | | 331 |
| 312 | 1.3.1. then 1.3.2. | | 320 |
| 313 | 1.3.1. then 1.3.2. | | 289 |
| 314 | 1.3.1. then 1.3.2. | | 379 |
| 315 | 1.3.1. then 1.3.2. | | 291 |
| 316 | 1.3.1. then 1.3.2. | | 305 |
| 317 | 1.3.1. then 1.3.2. | | 351 |
| 318 | 1.3.1. then 1.3.2. | | 325 |
| 319 | 1.3.1. then 1.3.2. | | 289 |
| 320 | 1.3.1. then 1.3.2. | | 293 |
| 321 | 1.3.1. then 1.3.2. | | 293 |

| | | |
|---|---|---|
| 322 | 1.3.1. then 1.3.2. | 293 |
| 323 | 1.3.1. then 1.3.2. | 311 |
| 324 | 1.3.1. then 1.3.2. | 354 |
| 325 | 1.3.1. then 1.3.2. | 401 |
| 326 | 1.3.1. then 1.3.2. | 309 |
| 327 | 1.3.1. then 1.3.2. | 309 |
| 328 | 1.3.1. then 1.3.2. | 309 |
| 329 | 1.3.1. then 1.3.2. | 290 |
| 330 | 1.3.1. then 1.3.2. | 228 |
| 331 | 1.3.1. then 1.3.2. | 489 |
| 332 | 1.3.1. then 1.3.2. | 285 |
| 333 | 1.3.1. then 1.3.2. | 299 |
| 334 | 1.3.1. then 1.3.2. | 352 |
| 335 | 1.3.1. then 1.3.2. | 338 |
| 336 | 1.3.1. then 1.3.2. | 348 |
| 337 | 1.3.1. then 1.3.2. | 595 |
| 338 | 1.3.1. then 1.3.2. | 242 |
| 339 | 1.3.1. then 1.3.2. | 348 |
| 340 | 1.3.1. then 1.3.2. | 326 |
| 341 | 1.3.1. then 1.3.2. | 329 |
| 342 | 1.3.1. then 1.3.2. | 424 |
| 343 | 1.3.1. then 1.3.2. | 298 |
| 344 | 1.3.1. then 1.3.2. | 352 |
| 345 | 1.3.1. then 1.3.2. | 482 |
| 346 | 1.3.1. then 1.3.2. | 243 |
| 347 | 1.3.1. then 1.3.2. | 325 |
| 348 | 1.3.1. then 1.3.2. | 339 |
| 349 | 1.3.1. then 1.3.2. | 297 |
| 350 | 1.3.1. then 1.3.2. | 282 |
| 351 | 1.3.1. then 1.3.2. | 225 |
| 352 | 1.3.1. then 1.3.2. | 314 |
| 353 | 1.3.1. then 1.3.2. | 229 |
| 354 | 1.3.1. then 1.3.2. | 259 |
| 355 | 1.3.1. then 1.3.2. | 275 |
| 356 | 1.3.1. then 1.3.2. | 381 |
| 357 | 1.3.1. then 1.3.2. | 256 |
| 358 | | |
| 359 | | |
| 360 | | |

| $^1$H NMR Number | $^1$H NMR Description | Solvent |
|---|---|---|
| [1] | 0.80 (t, 3H); 1.40-1.60 (m, 1H); 1.75-1.95 (m, 1H); 2.10 (dd, 1H); 2.45 (dd, 1H, partially overlapped with solvent); 2.8 (m, 1H); 3.05 (dd, 1H); 3.60 (m, 3H); 4.45 (dd, 1H); 6.90 (s (broad), 1H); 7.30 (s (broad), 1H). | DMSO |
| [2] | 0.80 (t, 3H); 1.45-1.70 (m, 1H); 1.75-1.95 (m, 1H); 2.50 (m, 2H, partially overlapped with solvent); 3.40 (m, 1H); 3.50-3.70 (m, 5H, partially overlapped with solvent); 4.45 (dd, 1H); 6.90 (s (broad), 1H); 7.30 (s (broad), 1H). | DMSO |
| [3] | 0.80 (t, 3H); 1.40-1.90 (m, 6H); 2.10 (dd, 1H); 2.30-2.60 (m, 6H); 3.05 (dd, 1H); 3.60 (dd, 1H); 3.60 (dd, 1H); 4.30 (dd, 1H); 6.90 (s (broad), 1H); 7.30 (s (broad), 1H). | DMSO |
| [4] | 0.80 (t, 3H); 1.20 (d, 6H); 1.40-1.60 (m, 1H); 1.70-1.85 (m, 1H); 2.45 (dd, 1H); 2.35-2.55 (m, 1H, overlaped with solvent); 2.55 (m, 2H); 2.90 (s, 1H); 3.00 (m, 1H); 3.60 (dd, 1H); 4.30 (dd, 1H); 6.90 (s (broad), 1H); 7.30 (s (broad), 1H). | DMSO |
| [5] | 0.80 (t, 3H); 1.20 (d, 6H); 1.40-1.65 (m, 1H); 1.75-1.90 (m, 1H); 2.15 (dd, 1H); 2.35-2.55 (m, 1H); 2.55 (d, 2H); 2.95 (s, 1H); 3.30 (m, 1H, overlaped with solvent); 3.45 (dd, 1H); 4.45 (dd, 1H); 6.90 (s (broad), 1H); 7.30 (s (broad), 1H). | DMSO |
| [6] | 0.80 (t, 3H); 1.40-1.65 (m, 1H); 1.75-1.95 (m, 1H); 2.10 (dd, 1H); 2.45 (dd, 1H, partially overlapped with solvent); 2.75 (m, 1H); 3.20-3.50 (m, 5H, partially overlapped with solvent); 4.30 (d, 2H); 4.45 (dd, 1H); 6.90 (s (broad), 1H); 7.35 (s (broad), 1H). | DMSO |
| [7] | 0.80 (t, 3H); 1.40-1.60 (m, 1H); 1.70-1.90 (m, 1H); 2.20 (dd, 1H); 2.45 (dd, 1H); 2.60 (m, 1H); 3.25 (m, 1H, overlaped with solvent); 3.45 (dd, 1H); 3.60 (d, 2H); 4.30 (dd, 1H); 6.90 (s (broad), 1H); 7.30 (s (broad), 1H); 7.60-8.00 (m, 5H). | DMSO |
| [8] | 0.85 (t, 3H); 1.55-1.70 (m, 1H); 1.80-1.95 (m, 1H); 2.65 (dd, 1H); 2.85 (dd, 1H); 3.45 (dd, 1H); 3.80 (m, 2H), 4.05 (m, 1H); 4.50 (dd, 1H); 6.80 (s (broad), 1H); 7.40 (s (broad), 1H); 9.20 (s, 1H). | DMSO |
| [9] | 0.65 (t, 3H); 1.40-1.60 (m, 1H); 1.75-1.90 (m, 1H); 2.15 (dd, 1H); 2.30 (s, 3H); 2.45 (dd, 1H); 2.80-2.95 (m, 1H); 3.25-3.40 (m, 2H); 4.30-4.45 (m, 3H); 7.10 (s (broad), 1H); 7.50 (s, 1H) | DMSO |
| [10] | 0.70-0.90 (m, 3H); 1.40-1.70 (m, 1H); 1.80-1.90 (m, 1H); 2.50-2.90 (m, 4H, partially overlapped with solvent); 3.50 (dd, 1H of one of the diastereoisomers, 3.70 (dd, 1H of two diastereoisomers); 3.80 (dd~t, 1H of one of the diastereoisomers) 4.30-4.50 (m, 2H); 6.90 (s (broad), 1H); 7.30 (s (broad), 1H); 7.60 (dd, 1H); 8.45 (d, 1H); 8.80 (d, 1H); 9.20 (s(broad), 1H). | DMSO |
| [11] | 0.75 (t, 3H); 1.55-1.70 (m, 1H); 1.80-1.95 (m, 1H); 2.50 (m, 1H, overlapped with solvent); 2.70 (m, 1H); 3.30 (m, 1H, overlapped with solvent); 3.70 (m, 1H); 3.90 (dd, 1H); 4.50 (dd, 1H); 6.90 (s (broad), 1H); 7.10 (d, 1H); 7.20-7.40 (m, 2H); 7.50 (d, 1H). | DMSO |
| [12] | 0.80 (t, 3H); 1.50-1.75 (m, 1H); 1.80-1.95 (m, 1H); 2.45 (dd, 1H, overlapped with solvent); 2.75 (dd, 1H); 3.40-3.80 (m, 3H); 4.45 (dd, 1H); 6.90 (s (broad), 1H); 7.20-7.25 (m, 5H). | DMSO |
| [13] | 0.80 (t, 3H); 1.50-1.75 (m, 1H); 1.80-1.95 (m, 1H); 2.45 (dd, 1H, overlapped with solvent); 2.75 (dd, 1H); 3.15 (dd, 1H); 3.65 (m, 1H); 3.95 (dd, 1H); 4.45 (dd, 1H); 6.90 (s (broad), 1H); 7.10-7.25 (m, 3H); 7.30-7.50 (m, 2H). | DMSO |
| [14] | 0.80 (t, 3H); 1.55-1.70 (m, 1H); 1.80-1.95 (m, 1H); 2.55 (dd, 1H, overlapped with solvent); 2.75 (dd, 1H); 3.30 (m, 1H, overlapped with solvent); 3.70 (dd, 1H); 4.50 (dd, 1H); 6.95 (s (broad), 1H); 7.30-7.70 (m, 10H). | DMSO |
| [15] | 0.85 (t, 3H); 1.60-1.75 (m, 1H); 1.75-1.95 (m, 1H); 2.55 (m, 1H, overlapped with solvent); 2.75 (dd, 1H); 3.30 (m, 1H, overlapped with solvent); 3.50-3.85 (m, 2H); 4.40 (dd, 1H); 6.95 (s (broad), 1H); 7.30-7.80 (m, 10H). | DMSO |

-continued

| ¹H NMR Number | ¹H NMR Description | Solvent |
|---|---|---|
| [16] | 0.90 (t, 3H); 1.20 (s, 3H); 1.60-1.80 (m, 1H); 1.80-2.10 (m, 1H); 2.40 (dd, 1H); 2.50-2.60 (m, 3H, overlaped with solvent); 3.20 (m, 1H); 3.50-3.70 (m, 3H); 4.45 (dd, 1H); 5.45 (s (broad), 1H); 6.30 (s (broad), 1H). | CDCl₃ |
| [17] | 1.05 (t, 3H); 1.60-1.75 (m, 1H); 1.90-2.20 (m, 1H); 2.70 (dd, 1H); 3.80 (m, 2H); 4.45-4.50 (m, 2H); 5.30 (s (broad), 1H); 6.30 (s (broad), 1H); 7.70 (s, 1H). | CDCl₃ |
| [18] | 0.80 (t, 3H); 1.50-1.65 (m, 1H); 1.75-1.90 (m, 1H); 2.25 (dd, 1H); 2.55 (s, 3H); 2.75 (m, 1H); 2.90 (m, 2H); 3.20 (d, 2H); 3.3 (m, 3H, overlapped with solvent); 3.5 (dd, 1H); 4.05 (dd, 1H of 1 of the diastereomeres); 4.35 (dd, 1H); 6.95 (s(broad), 1H); 7.35 (s(broad), 1H). | DMSO |
| [19] | 0.80 (t, 3H); 0.90 (t, 3H); 1.30-1.70 (m, 3H); 1.70-2.00 (m, 2H); 2.10-2.40 (m, 2H); 2.90 (dd, 1H); 3.60 (dd, 1H); 4.30 (dd, 1H); 6.90 (s (broad), 1H); 7.30 (s (broad), 1H). | DMSO |
| [20] | 0.80 (t, 3H); 0.85 (t, 3H); 1.30-1.70 (m, 3H); 1.70-1.90 (m, 1H); 2.00 (dd, 1H); 2.20 (m, 1H); 2.45 (dd, 1H); 3.15 (dd, 1H); 3.45 (dd, 1H); 4.30 (dd, 1H); 6.90 (s (broad), 1H); 7.30 (s (broad), 1H). | DMSO |
| [21] | 0.80 (t, 3H); 1.45-1.55 (m, 1H); 1.60-1.95 (m, 1H); 2.1 (dd, 1H); 2.45 (dd, 1H); 2.55 (d, 3H); 2.55 (m, 1H); 3.0 (dd, 1H); 3.4 (dd, 2H); 3.6 (dd, 1H); 4.30 (dd, 1H); 7.8 (s(broad), 1H). | DMSO |
| [22] | 0.00-0.005 (m, 2H, overlapped with TMS); 0.40-0.55 (m, 2H); 0.55-0.70 (m, 1H); 0.85-1.00 (t, 3H); 1.25-1.55 (m, 2H); 1.60-1.85 (m, 1H); 1.85-2.05 (m, 1H); 2.05-2.30 (m, 1H); 2.35-2.70 (m, 2H); 3.10 (m, 1H); 3.55 (m, 1H); 4.45 (dd, 1H); 5.45 (s (broad), 1H); 6.20 (s (broad), 1H) | DMSO |
| [23] | 0.95 (t, 3H); 1.60-1.80 (m, 1H); 1.90-2.10 (m, 1H); 2.60-2.70 (m, 2H); 3.45 (dd, 1H); 3.65 (m, 1H), 3.80 (dd, 1H); 4.50 (dd, 1H); 5.40 (s (broad), 1H); 6.00-6.20 (m, 2H); 6.30 (d, 1H); 7.45 (d, 1H). | DMSO |
| [24] | 0.95 (t, 3H); 1.60-1.70 (m, 1H); 2.00-2.10 (m, 1H); 2.60 (dd, 1H); 2.85 (dd, 1H); 3.40 (m, 1H); 3.40-3.80 (m, 3H); 4.50 (dd, 1H); 5.40 (s (broad), 1H); 6.10 (s (broad), 1H); 6.15 (d, 1H); 6.35 (d, 1H); 7.40 (d, 1H). | DMSO |
| [25] | 0.80 (t, 3H); 1.60-1.70 (m, 1H); 1.90-2.10 (m, 1H); 2.25 (s, 3H); 2.60 (dd, 1H); 2.80 (dd, 1H); 3.30-3.60 (m, 2H), 3.75 (dd, 1H); 3.95 (dd, 1H); 4.50 (dd, 1H); 5.50 (s (broad), 1H); 6.30 (s (broad), 1H); 6.90-7.10 (m, 3H), 7.20 (dd, 1H). | CDCl₃ |
| [26] | 0.90 (t, 3H); 1.60-1.70 (m, 1H); 1.85-2.10 (m, 1H); 2.25 (s, 3H); 2.55 (dd, 1H); 2.85 (dd, 1H); 3.30-3.60 (m, 2H), 3.75 (dd, 1H); 3.80 (dd, 1H); 4.50 (dd, 1H); 5.50 (s (broad), 1H); 6.30 (s (broad), 1H); 6.90-7.10 (m, 3H), 7.20 (dd, 1H). | CDCl₃ |
| [27] | 0.70-0.90 (m, 3H); 1.50-1.75 (m, 1H); 1.80-1.95 (m, 1H); 2.50-2.90 (m, 2H); 3.20-3.40 (m, 1H, overlapped with solvent); 3.50-3.80 (m, 3H); 3.95 (dd, 1H for one of the diastereoisomer); 4.45 (dd, 1H); 6.90 (s (broad); 7.30 (s (broad) 1H); 8.70 (d, 2H); 9.15 (d, 1H). | DMSO |
| [28] | 0.95 (t, 3H); 1.60-1.70 (m, 1H); 1.85-2.10 (m, 1H); 2.80 (dd, 1H); 3.05 (dd, 1H); 3.55 (dd, 1H); 4.00 (dd, 1H); 4.55 (dd, 1H); 4.8 (m, 1H); 5.60 (dd, 2H); 6.30 (s (broad), 1H); 6.75 (d, 2H). | CDCl₃ |
| [29] | 0.75 (t, 3H); 1.45-1.60 (m, 1H); 1.75-1.90 (m, 1H); 2.05 (dd, 1H); 2.40 (dd, 1H); 2.60 (m, 1H); 3.05 (dd, 1H); 3.25 (s, 3H); 3.30 (m, 2H, partially overlapped with solvent); 3.55 (dd, 1H); 4.30 (dd, 1H); 7.05 (s (broad), 1H); 7.40 (s (broad), 1H) | DMSO |
| [30] | 0.80 (t, 3H), 1.41-1.63 (m, 1H), 1.71-1.86 (m, 1H), 2.12 (dd, 1H), 2.43 (dd, 1H), 2.82 (m, 1H), 3.2-3.4 (m, 2H), 4.23 (d, 2H), 4.31 (dd, 1H), 6.97 (s (broad), 1H), 7.31 (s (broad), 1H), 7.94 (s, 1H), 8.5 (s, 1H). | DMSO |
| [31] | 0.84 (t, 3H), 1.60-1.72 (m, 1H), 1.86-1.98 (m, 1H), 2.78 (dd, 1H), 3.0 (dd, 1H), 3.42 (dd, 1H), 3.98 (dd, 1H), 4.53 (dd, 1H), 5.08 (m, 1H), 5.58 (s (broad), 1H), 6.21 (s, 2H), 6.25 (s (broad), 1H), 6.73 (s, 1H). | CDCl₃ |
| [32] | 0.83 (t, 3H), 1.52-1.70 (m, 1H), 1.70-1.84 (m, 1H), 2.5 (m, overlapped with DMSO), 2.72 (dd, 1H), 3.64 (m, 2H), 3.84 (m, 1H), 4.39 (dd, 1H), 7.05 (s (broad), 1H), 7.42 (m, 2H). | DMSO |
| [33] | 0.81 (t, 3H), 1.48-1.51 (m, 1H), 1.80-1.94 (m, 1H), 2.5 (m, overlapped with DMSO), 2.72 (dd, 1H), 3.78 (m, H), 3.95 (m, 1H), 4.38 (m, 1H), 7.05 (s (broad), 1H), 7.42 (m, 2H). | DMSO |
| [34] | 1.02 (t, 3H), 1.63-1.82 (m, 1H), 1.91-2.08 (m, 1H), 2.86 (dd, 1H), 3.22 (dd, 1H), 3.83 (dd, 1H), 3.98 (dd, 1H), 4.44 (dd, 1H), 5.3-5.5 (m, 2H), 6.13 (s (broad), 1H), 6.21 (s, 2H). | CDCl₃ |

| | Intermediates of Formula AA-II | | | |
|---|---|---|---|---|
| Cmpd. number | IUPAC chemical name | Configuration data | LC/MS MH⁺ | GC/MS M⁺· |
| AA 1 | ethyl 3-({[(1S)-1-(aminocarbonyl)propyl]amino}methyl)hexanoate hydrochloride | A - 3§,1S | PURE | 259 | |
| AA 2 | ethyl 3-({[(1S)-1-(aminocarbonyl)propyl]amino}methyl)hexanoate hydrochloride | B - 3§,1S | PURE | 259 | |
| AA 3 | 2-(1-adamantyl)ethyl 3-({[(1S)-1-(aminocarbonyl)propyl]amino}methyl)hexanoate hydrochloride | 3,1S | RAC | 393 | |
| AA 4 | butyl 3-({[(1S)-1-(aminocarbonyl)propyl]amino}methyl)hexanoate hydrochloride | 3,1S | RAC | | 286 |
| AA 5 | isopropyl 3-({[(1S)-1-(aminocarbonyl)propyl]amino}methyl)hexanoate hydrochloride | 3,1S | RAC | 273 | |

EXAMPLE 8

LBS Binding Assay

[LBS stands for Levetiracetam Binding Site cf. M. Noyer et al., Eur. J. Pharmacol., 286 (1995) 137-146.]

The inhibition constant ($K_i$) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the $IC_{50}$. The equilibrium dissociation constant Ki is proportional to the $IC_{50}$ and is calculated using the equation of Cheng and Prusoff (Cheng Y. et al., Biochem. Pharmacol. 1972, 22, 3099-3108).

The concentration range usually encompasses 6 log units with variable steps (0.3 to 0.5 log). Assays are performed in mono- or duplicate, each $K_i$ determination is performed on two different samples of test substance.

Cerebral cortex from 200-250 g male Sprague-Dawley rats are homogenised using a Potter S homogeniser (10 strokes at 1,000 rpm; Braun, Germany) in 20 mmol/l Tris-HCl (pH 7.4), 250 mmol/l sucrose (buffer A); all operations are performed at 4° C. The homogenate is centrifuged at 30,000 g for 15 min. The crude membrane pellet obtained is resuspended in 50 mmol/l Tris-HCl (pH 7.4), (buffer B) and incubated 15 min at 37° C., centrifuged at 30,000×g for 15 min and washed twice with the same buffer. The final pellet is resuspended in buffer A at a protein concentration ranging from 15 to 25 mg/ml and stored in liquid nitrogen.

Membranes (150-200 μg of protein/assay) are incubated at 4° C. for 120 min in 0.5 ml of a 50 mmol/l Tris-HCl buffer (pH 7.4) containing 2 mmol/l $MgCl_2$, 1 to 2 $10^{-9}$ mol/l of [$^3$H]-2-[4-(3-azidophenyl)-2-oxo-1-pyrrolidinyl]butanamide and increasing concentrations of the test substance. The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mmol/l levetiracetam to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a β-counter (Tri-Carb 1900 or TopCount 9206, Camberra Packard, Belgium, or any other equivalent counter). Data analysis is performed by a computerized non linear curve fitting method using a set of equations describing several binding models assuming populations of independent non-interacting receptors which obey to the law of mass.

Compounds according to the invention showed pKi values of 6.0 and greater. Particular affinity is shown by compound nos.: 8, 9, 10, 22, 23, 27, 30, 31, 32, 33, 38, 40, 41, 43, 46, 47, 49, 64, 71, 72, 73, 75, 81, 83, 86, 87, 88, 92, 93, 95, 96, 98, 100, 103, 105, 110, 119, 127, 142, 146, 149, 151, 152, 156, 157, 158, 159, 162, 163, 164, 165, 166, 169, 170, 171, 173, 174, 175, 176, 180, 181, 185, 187, 188, 195, 196, 197, 198, 200, 201, 204, 205, 207, 209, 211, 212, 213, 214, 215, 219, 221, 222, 223, 224, 225, 226, 228, 229, 234, 250, 251, 252, 264, 265, 267, 304, 306, 350 and 351.

EXAMPLE 9

Animal Model of Sound-Susceptible Mice

The objective of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41).

Male or female genetically sound-sensitive mice (14-28 g; N=10), derived from a DBA strain originally selected by Dr. Lehmann of the Laboratory of Acoustic Physiology (Paris) and bred in the UCB Pharma Sector husbandry unit since 1978, are used. The experimental design consisted of several groups, one group receiving the vehicle control and the other groups different doses of the test-compound. The compounds are administered intraperitoneally 60 minutes before the induction of audiogenic seizures. The range of the doses administered had a logarithmic progression, generally between $1.0 \times 10^{-5}$ mol/kg and $1.0 \times 10^{-3}$ mol/kg, but lower or higher doses are tested if necessary.

For testing, the animals are placed in small cages, one mouse per cage, in a sound-attenuated chamber. After a period of orientation of 30 seconds, the acoustic stimulus (90 dB, 10-20 kHz) is delivered for 30 seconds via loudspeakers positioned above each cage. During this interval, the mice are observed and the presence of the 3 phases of the seizure activity namely wild running, clonic and tonic convulsions, is recorded. The proportion of mice protected against wild running, clonic and tonic convulsions, respectively, is calculated.

For active compounds, an ED50 value, i.e. the dose producing 50% protection relative to the control group, together with 95% confidence limits, was calculated using a Probit Analysis (SAS/STAT® Software, version 6.09, PROBIT procedure) of the proportions of protected mice for each of the 3 phases of the seizure activity.

Compounds according to the invention showed ED50 values of 1.0E-04 or lower. Particularly promising activity was shown by compounds nos.: 8, 9, 10, 22, 23, 27, 30, 31, 32, 33, 38, 40, 41, 46, 47, 64, 71, 72, 81, 86, 87, 88, 92, 93, 95, 96, 100, 105, 110, 146, 151, 152, 156, 158, 159, 162, 163, 164, 165, 166, 180, 181, 187, 188, 195, 196, 197, 198, 200, 201, 204, 205, 207, 209, 211, 212, 213, 214, 215, 219, 221, 222, 223, 224, 226, 228, 229, 234, 250, 251, 252, 264, 265, 267 AA 1, AA 2, AA 3, AA 4 and AA 5.

We claim:

1. A method of preparation of compound of formula (I)

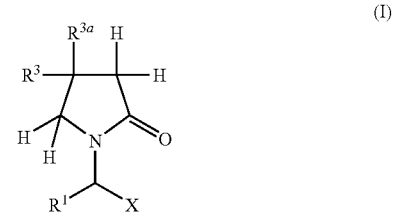

wherein

X is —$CA^1NR^5R^6$ or —$CA^1$-$R^8$;

$A^1$ is oxygen, sulfur or —$NR^9$;

$R^1$ is hydrogen, alkyl, aryl or —$CH_2$—$R^{1a}$ wherein $R^{1a}$ is aryl, halogen, hydroxy, amino, nitro or cyano;

$R^3$ is hydrogen, halogen, thiol, nitro, nitrooxy, cyano, azido, carboxy, amido, sulfonic acid, sulfonamide, alkyl, alkenyl, alkynyl, ester, ether, aryl, tetrazolyl, thiazolyl, thienyl, furyl, pyrrolyl, pyridinyl, alkynyloxy, acyloxy, oxyester, oxyamido, alkylsulfonyloxy, alkylsulfinyloxy, arylsulfonyloxy, arylsulfinyloxy, aryloxy, aralkoxy, alkylthio, alkenylthio, alkynylthio, arylthio, formyl, acetyl, propionyl, isobutyryl, valeryl, lauroyl, heptanedioyl, cyclohexanecarbonyl, crotonoyl, furmaroyl, acyloyl, benzoyl, naphtoyl, 4-carboxybutanoyl, oxalyl, ethoxalyl, cysteinyl, oxamoyl, alkylsulfonyl, alkenylsulfonyl, alkynylsulfonyl, arylsulfonyl, alkylsulfinyl, alkenylsulfinyl, alkynylsulfinyl or arylsulfinyl;

$R^{3a}$ is hydrogen, halogen, alkyl, alkenyl, alkynyl or aryl;

$R^5$, $R^6$ and $R^9$ are the same or different and each is independently hydrogen, hydroxy, alkyl, aryl, alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy or arylakoxy; and $R^8$ is hydrogen, hydroxy, thiol, halogen, alkyl, aryl, alkylthio, alkenylthio, alkynylthio;

with the provisos that at least one of $R^3$ and $R^{3a}$ is other than hydrogen; and that when the compound is a mixture of all possible isomers, X is —$CONR^5R^6$ and $R^1$ is hydrogen, methyl, ethyl or propyl then $R^3$ and $R^{3a}$ substitution is other than mono-, di-methyl or mono-ethyl;

and that when $R^1$ and $R^{3a}$ are both hydrogen and X is —$CONR^5R^6$ then $R^3$ is different from carboxy, ester, amido, substituted oxo-pyrrolidine, alkynyloxy, acyloxy, oxyester, oxyamido, alkylsulfonyloxy, alkylsulfinyloxy, arylsulfonyloxy, arylsulfinyloxy, aryloxy, aralkoxy, methyl, naphtyl, phenyl optionally substituted by oxy derivatives or in the para position by an halogen atom;

which comprises cyclisation of a compound of formula (AA-II)

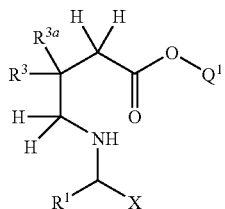

(AA-II)

wherein $R^1$, $R^3$, $R^{3a}$ and X are as defined above for compound of formula (I) and $Q^1$ together with the oxygen to which it is attached is a leaving group.

2. The method of preparation of compound of formula (I) according to claim 1 wherein $Q^1$ is a substituent group selected from, a) alkyl; or b) linear or branched $C_{1-4}$-alkyl.

3. The method of preparation of compound of formula (I) according to claim 1 wherein $R^1$ is alkyl;

X is —$CA^1NR^5R^6$;

$R^3$ is alkyl or alkenyl; and $R^{3a}$ is hydrogen.

4. A method of preparation of (2S)-2-[(4S)-2-oxo-4-propylpyrrolidinyl]butanamide 158 and (2S)-2-[(4R)-2-oxo-4-propylpyrrolidinyl]butanamide 159 which comprises reduction of compound 374:

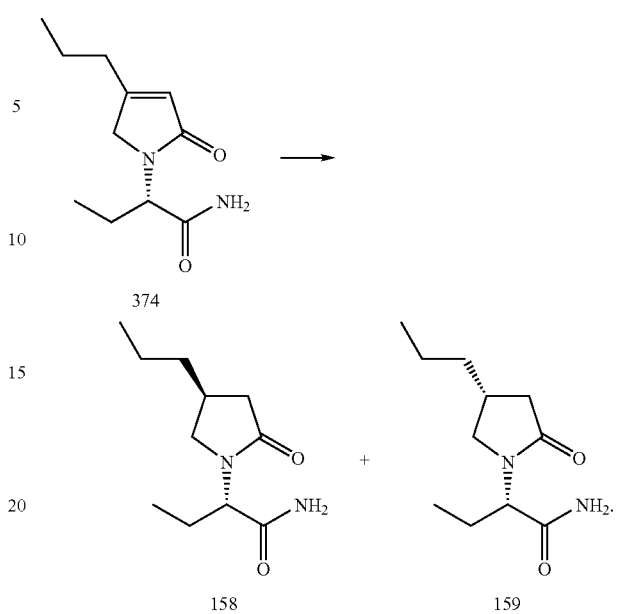

5. The method of preparation according to claim 4 which is performed in the presence of Pd/C in an aqueous solution of $NH_4COOH$.

6. The method of preparation according to claim 4 which comprises separation of (2S)-2-[(4S)-2-oxo-4-propylpyrrolidinyl]butanamide 158 and (2S)-2-[(4R)-2-oxo-4-propylpyrrolidinyl]butanamide 159.

7. The method of preparation according to claim 4 which affords (2S)-2-[(4R)-2-oxo-4-propylpyrrolidinyl]butanamide 159.

* * * * *